US012251445B2

(12) United States Patent
Bera et al.

(10) Patent No.: US 12,251,445 B2
(45) Date of Patent: Mar. 18, 2025

(54) GAMMA-HYDROXYBUTYRATE DELIVERING COMPOUNDS AND PROCESSES FOR MAKING AND USING THEM

(71) Applicant: Zevra Therapeutics, Inc., Celebration, FL (US)

(72) Inventors: Sanjib Bera, Blacksburg, VA (US); Sven Guenther, Coralville, IA (US); Adam Smith, Orlando, FL (US); Travis Mickle, Kissimmee, FL (US)

(73) Assignee: Zevra Therapeutics, Inc.

( * ) Notice: Subject to any disclaimer, the term of this patent is extended or adjusted under 35 U.S.C. 154(b) by 0 days.

(21) Appl. No.: 18/303,226

(22) Filed: Apr. 19, 2023

(65) Prior Publication Data

US 2023/0382880 A1 Nov. 30, 2023

Related U.S. Application Data

(60) Provisional application No. 63/333,391, filed on Apr. 21, 2022.

(51) Int. Cl.
| | |
|---|---|
| *A61K 47/54* | (2017.01) |
| *A61K 45/06* | (2006.01) |
| *A61P 25/20* | (2006.01) |
| *C07C 69/14* | (2006.01) |
| *C07C 69/88* | (2006.01) |
| *C07C 69/96* | (2006.01) |
| *C07C 233/47* | (2006.01) |
| *C07C 271/64* | (2006.01) |
| *C07C 271/66* | (2006.01) |
| *C07C 301/00* | (2006.01) |
| *C07C 307/02* | (2006.01) |
| *C07C 307/06* | (2006.01) |
| *C07C 333/10* | (2006.01) |
| *C07D 307/20* | (2006.01) |
| *C07D 407/12* | (2006.01) |
| *C07F 9/09* | (2006.01) |
| *C07F 9/24* | (2006.01) |
| *A61K 9/00* | (2006.01) |

(52) U.S. Cl.
CPC ............ *A61K 47/542* (2017.08); *A61K 45/06* (2013.01); *A61P 25/20* (2018.01); *C07C 69/14* (2013.01); *C07C 69/88* (2013.01); *C07C 69/96* (2013.01); *C07C 233/47* (2013.01); *C07C 271/64* (2013.01); *C07C 271/66* (2013.01); *C07C 301/00* (2013.01); *C07C 307/02* (2013.01); *C07C 307/06* (2013.01); *C07C 333/10* (2013.01); *C07D 307/20* (2013.01); *C07D 407/12* (2013.01); *C07F 9/09* (2013.01); *C07F 9/2404* (2013.01); *C07F 9/2458* (2013.01); *A61K 9/0048* (2013.01)

(58) Field of Classification Search
None
See application file for complete search history.

(56) References Cited

U.S. PATENT DOCUMENTS

| | | | |
|---|---|---|---|
| 2002/0009667 | A1 | 1/2002 | Nishimura et al. |
| 2002/0009668 | A1 | 1/2002 | Nishimura et al. |
| 2004/0214755 | A1 | 10/2004 | Albericio et al. |
| 2004/0241580 | A1 | 12/2004 | Nishimura et al. |
| 2019/0194120 | A1 | 6/2019 | Xiang et al. |

FOREIGN PATENT DOCUMENTS

| | | |
|---|---|---|
| CN | 103226290 | 7/2013 |
| EP | 0388868 | 9/1990 |
| EP | 1162506 | 12/2001 |
| EP | 1164434 | 12/2001 |
| JP | 0859596 | 3/1996 |
| JP | 4973304 | 11/2008 |
| WO | 2014093791 | 6/2014 |
| WO | 2015083129 | 6/2015 |
| WO | 2015083129 A1 | 6/2015 |
| WO | 2017050259 | 3/2017 |
| WO | 2018191221 | 10/2018 |
| WO | 2022214025 | 10/2022 |

OTHER PUBLICATIONS

Kumar et. al., 2009, Allyl tetrahydropyranyl ether: a versatile alcohol/thiol protecting reagent, Tetrahedron Letters, 50, 6236-6240 (Year: 2009).*
PCT, International Search Report regarding Application No. PCT/US2023/019097, 19 pages, dated Sep. 4, 2023.
Database Registry, accession No. 1502828-48-9.
Database Registry, accession No. 1508153-72-7.
Chee, Gaik-Lean, "Selective Deprotection of Isopropyl Esters, Carbamates and Carbonates with Aluminum Chloride," Synlett, 2001, (10), 3 pgs., received Aug. 9, 2001.
Martin, S.F., et al., "Tetrahedron Letters," 39 (12), Department of Chemistry and Biochemistry, The University of Texas at Austin, 4 pgs., received Nov. 26, 1997.
Strasdeit, H., et al., "Syntheses and Properties of Zinc and Calcium Complexes of Valinate and Isovalinate:- Metal a-Amino Acidates as Possible Constituents of the Early Earth's Chemical Inventory," A European Journal, 7(5), 10 pgs., received Aug. 15, 2000.

(Continued)

*Primary Examiner* — Juliet C Switzer
*Assistant Examiner* — Dawanna Shar-Day White
(74) *Attorney, Agent, or Firm* — MCANDREWS HELD & MALLOY, LTD

(57) ABSTRACT

Disclosed are one or more compounds comprising chemically modified gamma-hydroxybutyrate (GHB), 2-hydroxytetrahydrofuran, and/or 1,4-butanediol, and salts of such compounds (GHB delivering compounds and salts thereof). Also disclosed are compositions comprising at least one GHB delivering compound, or a salt thereof, methods of making such compounds, and methods of using such GHB delivering compounds and compositions. Methods of treatment using the compounds are also disclosed.

19 Claims, 9 Drawing Sheets

(56) References Cited

OTHER PUBLICATIONS

PCT, International Search Report regarding Application No. PCT/US2023/019107, 20 pages, dated Jun. 19, 2023.
Hall, C. Dennis, et al., "Kinetics and mechanism of the hydrolysis of tetrahydro-2-furyl and tetrahydropyran-2-yl alkanoates," J Chem. Soc., Perkin Trans. 2, 1998, 23 pages, dated Mar. 25, 1998.
Macías-Benítez, Pablo, et al, "Microwave-Enhanced Coupling of Carboxylic Acids with Liquid Ketones and Cyclic Ethers Using Tetrabutylammonium Iodide/t Butyl Hydroperoxide," J. Org. Chem. 2020, 85, 6027-6043, dated Apr. 9, 2020.
Lee, Sunggi, et al., "Asymmetric Catalysis via Cyclic, Aliphatic Oxocarbenium Ions," J. Amer. Chem. Society 2017, 4 pages, dated Feb. 7, 2017.
PCT, International Search Report regarding Application No. PCT/US2023/019101, 13 pages, dated Aug. 23, 2023.
Gromek, S.M., et al.: "Synthesis and biological evaluation of santacruzamate A analogues for anti-proliferative and immunomodulatory activity", Bioorganic & Medicinal Chemistry, vol. 24, No. 21, Aug. 24, 2016 (Aug. 24, 2016), pp. 5183-5196, XP029763046, Elsevier Science Publishers, Oxford, GB ISSN: 0968-0896, DOI: 10.1016/j.bmc.2016.08.040, paragraph 4.2.2.21, intermediate product of LiOH hydrolysis of compound 21c.
Van Vranken, D.L. , et al.: "Catalysis of carbamate hydrolysis by an antibody", Tetrahedron Letters, vol. 35, No. 23, Sep. 6, 1994 (Sep. 6, 1994), pp. 3873-3876, XP093068584, Elsevier Science Publishers, Oxford, GB ISSN: 0040-4039, DOI: 10.1016/S0040-4039(00)76689-5 compound 2,(Received in USA Feb. 7, 1994, revised Apr. 7, 1994; accepted Apr. 8, 1994).
Patent Cooperation Treaty, "International Preliminary Report on Patentability and Written Opinion", issued in connection with International Patent Application No. PCT/US2023/019097, dated Oct. 8, 2024, 7 pages.
Patent Cooperation Treaty, "International Preliminary Report on Patentability and Written Opinion", issued in connection with International Patent Application No. PCT/US2023/019101, dated Oct. 8, 2024, 8 pages.
Patent Cooperation Treaty, "International Preliminary Report on Patentability and Written Opinion", issued in connection with International Patent Application No. PCT/US2023/019107, dated Oct. 8, 2024, 11 pages.
Patent Cooperation Treaty, "International Preliminary Report on Patentability and Written Opinion", issued in connection with International Patent Application No. PCT/US2023/019112, dated Oct. 8, 2024, 10 pages.

* cited by examiner

GAMMA-HYDROXYBUTYRATE DELIVERING COMPOUNDS AND PROCESSES FOR MAKING AND USING THEM

CROSS-REFERENCE TO RELATED APPLICATIONS

This application claims the benefit of U.S. Provisional Patent Application No. 63/333,391 which was filed on Apr. 21, 2022, which is incorporated by reference herein in its entirety.

BACKGROUND

Gamma-hydroxybutyrate (or γ-hydroxybutyrate "GHB") is a rapid-acting CNS (central nervous system) depressant and naturally occurring neurotransmitter. Pharmaceutical salts of GHB, including sodium oxybate (XYREM®), and mixed calcium, magnesium, potassium, and sodium oxybates (XYWAV®) have been approved by the US FDA for the treatment of narcolepsy and idiopathic hypersomnia.

While not wanting to be bound by any particular theory, these pharmaceutical preparations are thought to work primarily by producing a sedative effect and improving sleep consolidation resulting in a better night's rest and less daytime sleepiness. However, high doses of the drug are required due, in part, to suboptimal pharmacokinetics and oral bioavailability. Therefore, currently approved drugs require patients to administer the drug divided into two doses. The first dose is taken at bedtime and the second dose is typically taken about 2.5 to about 4 hours later. As a result, there is a need for treatment options that have improved pharmacokinetics including, for example, a higher oral bioavailability and/or a longer duration of action.

BRIEF SUMMARY

The present technology provides one or more compounds that deliver GHB to a human or animal subject. In some aspects, these compounds have increased bioavailabilty or a longer duration of action, or both, when compared to sodium oxybate (NaGHB). In other aspects, based on their improved bioavailablity, the compounds of the present technology can be administered to a human or animal subject at a lower molar dose that is therapeutically equivalent as compared to NaGHB. These GHB delivering compounds are prodrugs or precursors of gamma-hydroxybutyrate, salts of such compounds, and combinations thereof. In some aspects, prodrugs of GHB, 2-hydroxytetrahydrofuran (2-OH-THF), and 1,4-butanediol (BD) of the current invention/presently described technology provide similar or improved oral bioavailability of GHB, similar or extended-release of GHB, and/or reduced or zero sodium content in comparison to NaGHB. When administered as intended, the compounds of the presently described and claimed technology provide therapeutic plasma concentrations of GHB in a human or animal subject.

In at least one aspect of the present technology, there is provided a compound having a structure as shown in Formula I:

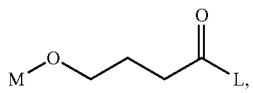

Formula I or a pharmaceutically acceptable salt thereof; where L is selected from the group consisting of hydroxyl, gamma-hydroxybutyrate, gamma-aminobutyric acid, 1,4-butanediol, 2-hydroxytetrahydrofuran, phosphate, sulfate, sulfamate, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amino acids, peptides, salts thereof, and combinations thereof; and where M is selected from the group consisting of hydrogen, gamma-hydroxybutyrate, gamma-aminobutyric acid, 1,4-butanediol, 2-hydroxytetrahydrofuran, sugar alcohol, ethylene glycol, glycerol, erythritol, threitol, arabitol, xylitol, ribitol, mannitol, sorbitol, galactitol, fucitol, iditol, inositol, volemitol, isomalt, lactitol, maltotriitol, maltotetraitol, polyglycitol, phosphate, sulfate, sulfamate, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, nitro, polycycloalkenyl, polycycloalkenylalkyl, polycycloalkyl, polycycloalkylalkyl, polyethylene glycol, thiol, amino acids, peptides, salts thereof, and combinations thereof.

Another aspect of the present technology includes a compound having a structure as shown in Formula II:

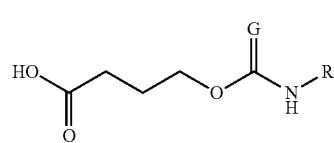

Formula II or a pharmaceutically acceptable salt thereof; wherein G is S or O, and R is selected from the group consisting of

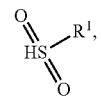

hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, polycycloalkenyl, polycycloalkenylalkyl, polycycloalkyl, polycycloalkylalkyl, polyethylene glycol, thiol, amino acids, peptides, salts thereof, and combinations thereof; and where $R^1$ is an amino acid or a peptide (e.g., a dipeptide or a tripeptide).

Another aspect of the present technology includes a compound having a structure of Formula III:

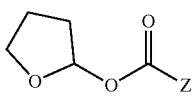

Formula III or a pharmaceutically acceptable salt thereof; wherein Z is selected from the group consisting of gamma-hydroxybutyrate, gamma-aminobutyric acid, 1,4-butanediol, 2-hydroxytetrahydrofuran, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, dicarboxylic acid, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, polycycloalkenyl, polycycloalkenylalkyl, polycycloalkyl, polycycloalkylalkyl, polyethylene glycol, thiol, amino acids, peptides, salts thereof, and combinations thereof.

Another aspect of the present technology includes a compound having a structure of Formula IV:

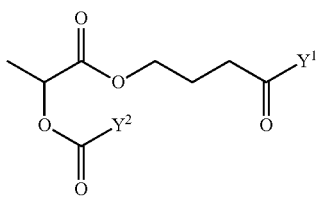

Formula IV wherein $Y^1$ and $Y^2$ are independently selected from the group consisting of hydroxyl, gamma-hydroxybutyrate, gamma-aminobutyric acid, 1,4-butanediol, 2-hydroxytetrahydrofuran, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, nitro, polycycloalkenyl, polycycloalkenylalkyl, polycycloalkyl, polycycloalkylalkyl, polyethylene glycol, thiol, amino acids, peptides, salts thereof, and combinations thereof.

Another aspect of the present technology includes a compound having a structure of Formula V:

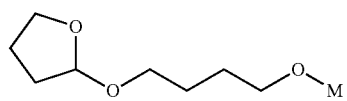

Formula V or a pharmaceutically acceptable salt thereof; where M is selected from the group consisting of hydrogen, 1,4-butanediol, 2-hydroxytetrahydrofuran, gamma-hydroxybutyrate, sugar alcohol, ethylene glycol, glycerol, erythritol, threitol, arabitol, xylitol, ribitol, mannitol, sorbitol, galactitol, fucitol, iditol, inositol, volemitol, isomalt, lactitol, maltotriitol, maltotetraitol, polyglycitol, gamma-aminobutyric acid, phosphate, sulfate, sulfamate, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, nitro, polycycloalkenyl, polycycloalkenylalkyl, polycycloalkyl, polycycloalkylalkyl, polyethylene glycol, thiol, amino acids, peptides, salts thereof, and combinations thereof.

In some aspects of the presently described technology, the amino acids in Formulas I-V are selected from the group containing alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and/or salts thereof. In some aspects, the peptide can be a dipeptide or a tripeptide.

In some aspects, at least one compound of the presently described technology having the structure of Formula I is selected from

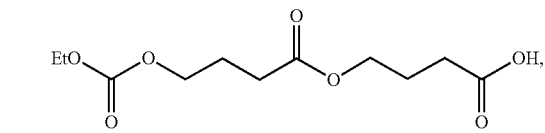

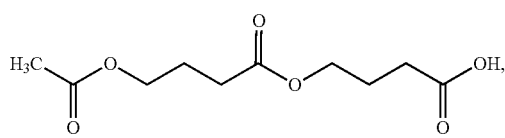

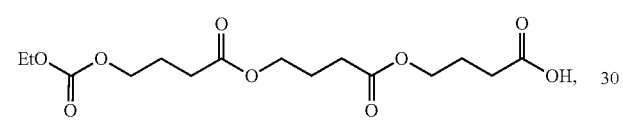

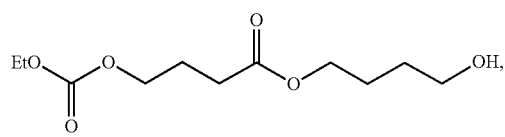

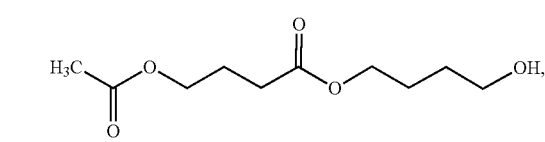

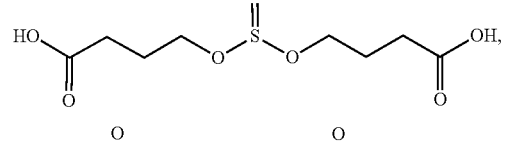

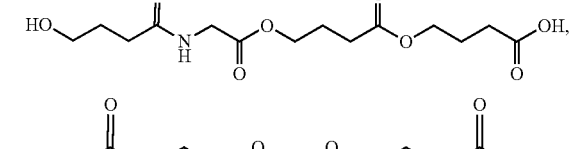

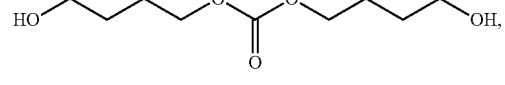

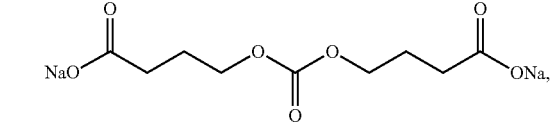

-continued

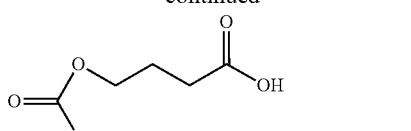

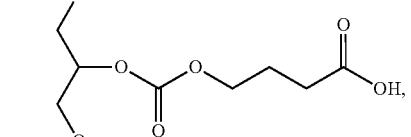

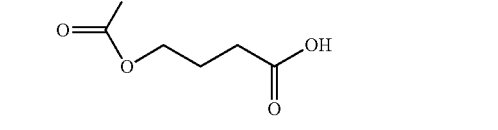

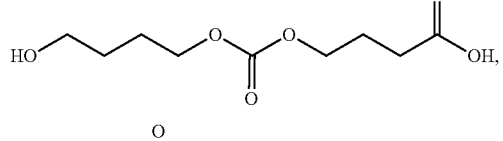

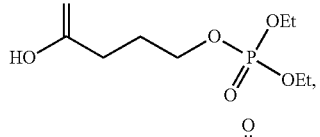

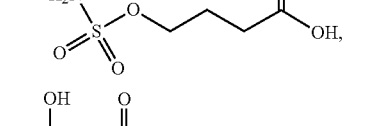

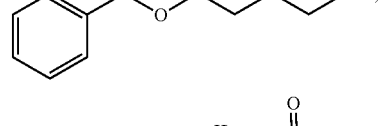

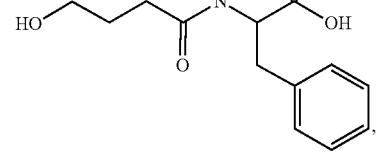

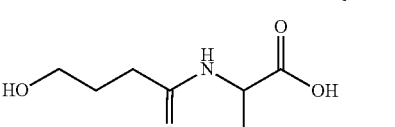

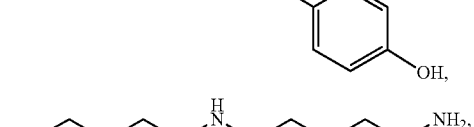

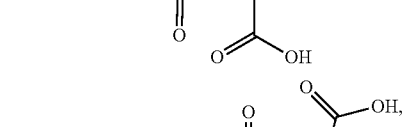

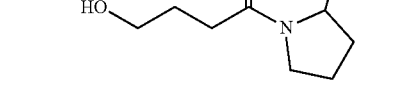

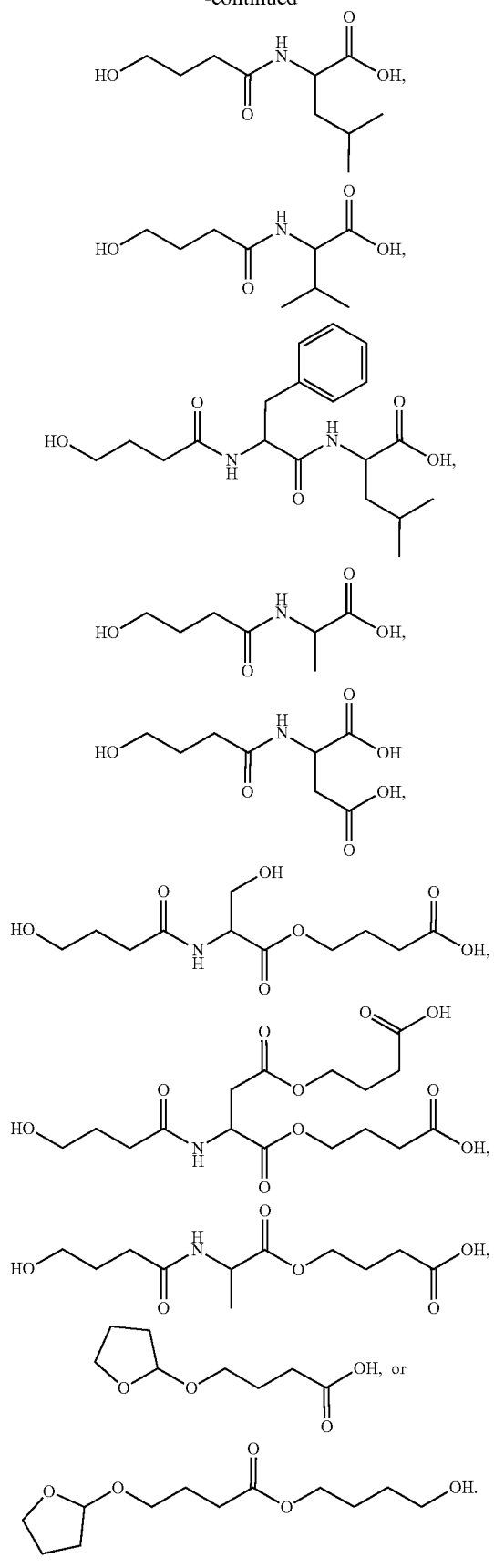
In some aspects, at least one compound of the presently described technology having the structure of Formula II is selected from
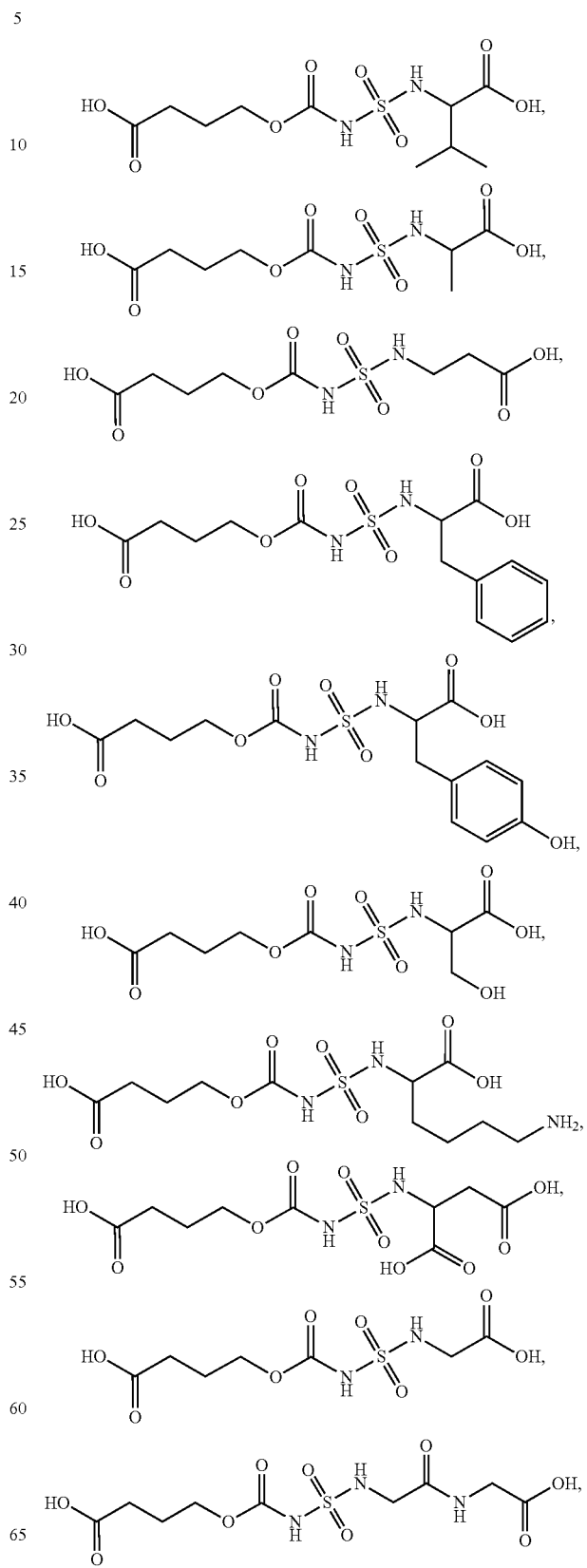

-continued
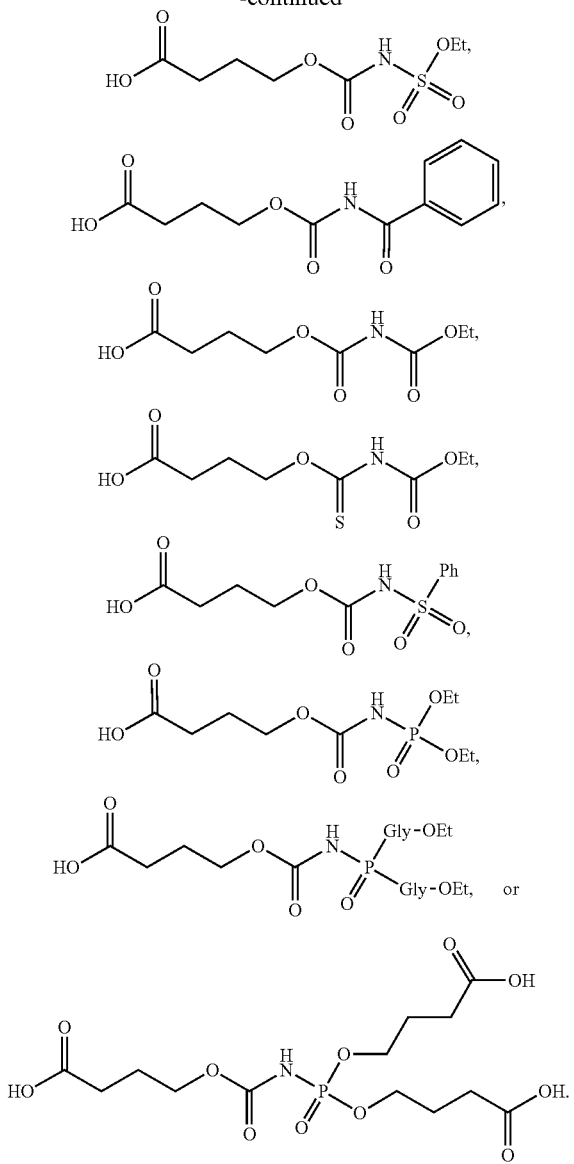
In some further aspects, one or more compounds of the presently described technology having the structure of Formula III are selected from
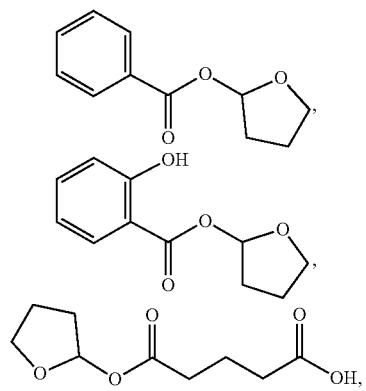
-continued
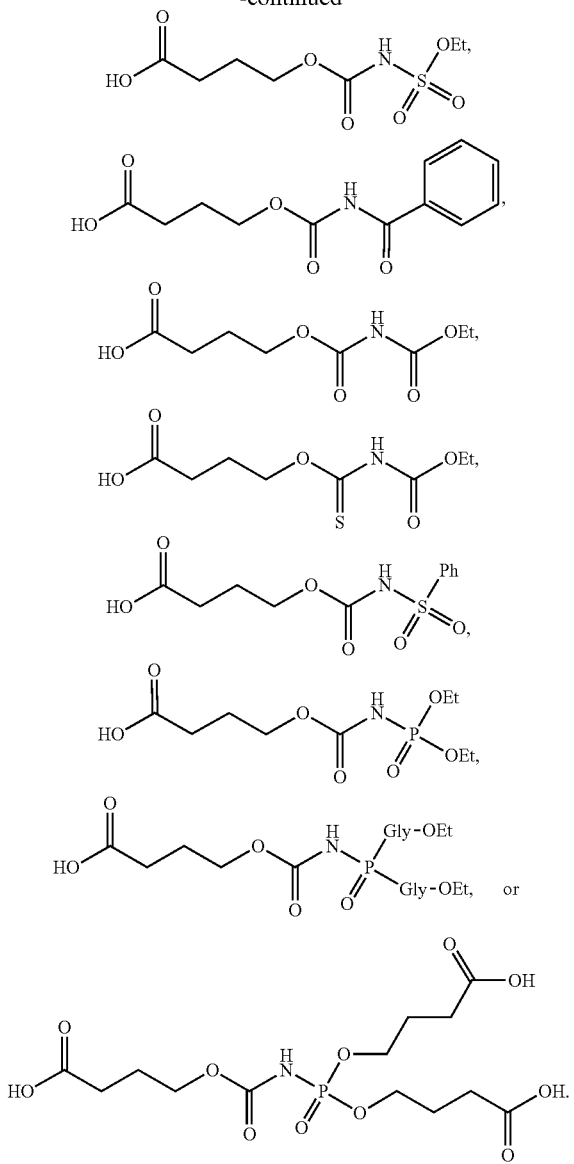
In some still further aspects, at least one compound of the presently described technology having the structure of Formula IV is selected from
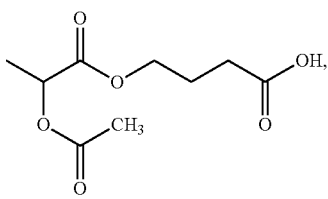

-continued

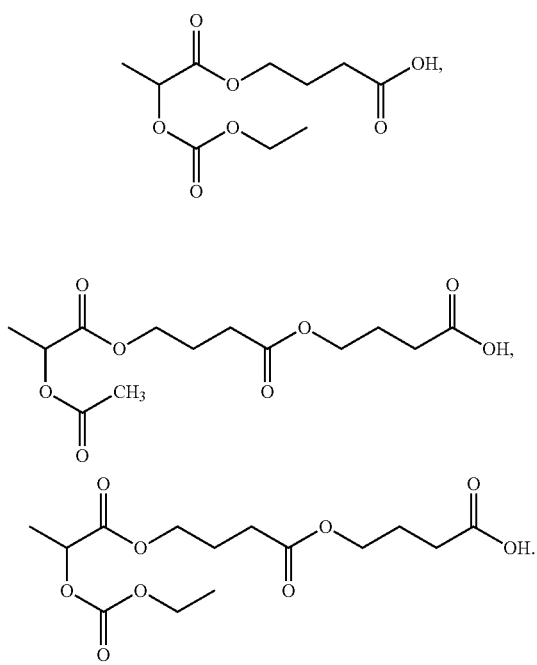

In some further aspects, one or more compounds of the presently described technology having the structure of Formula V are selected from

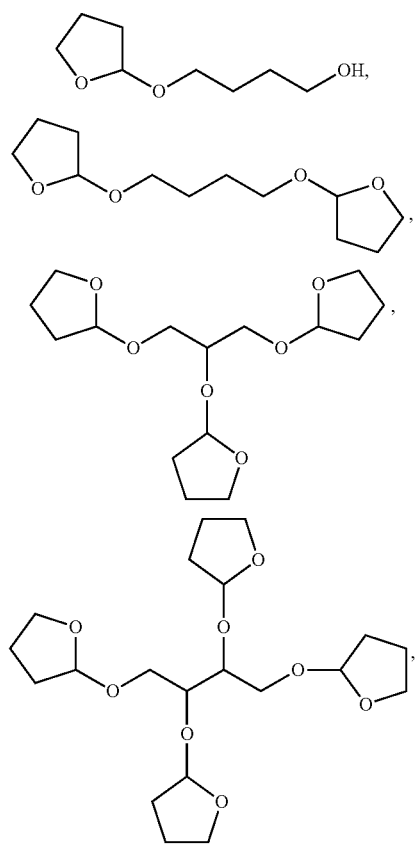

-continued

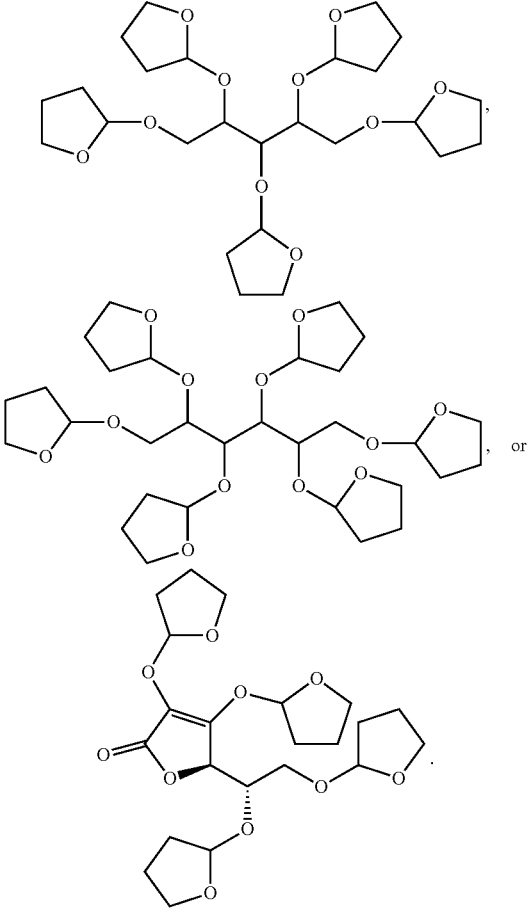

Another aspect of the present technology includes at least one composition comprising at least one of the disclosed GHB delivering compounds or compositions, or a pharmaceutically acceptable salt of the compound(s) or composition. It should be appreciated by those skilled in the art that in a further aspect of the present technology, compositions comprising unmodified GHB/NaGHB in combination with one or more of the presently described and claimed GHB delivering compounds are also envisaged.

In a further aspect of the present technology, there is provided at least one method of preventing or treating a sleep disorder in a subject in need thereof, comprising administering to the subject a composition comprising any one of the disclosed GHB delivering compounds or a pharmaceutically acceptable salt of the compound thereof. In some aspects, the sleep disorder is a symptom of a degenerative neurological disease or disorder and/or is a side effect of treating a degenerative neurological disease or disorder with medication or a therapeutic compound. In a further aspect, the degenerative neurological disease or disorder is selected from the group containing Parkinson's disease, primary parkinsonism, paralysis agitans, and/or idiopathic parkinsonism.

In some aspects of at least one method of the present technology, the composition further comprises amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, and solriamfetol, or combinations thereof.

In another aspect, the sleep disorder is excessive daytime sleepiness associated with central hypersomnolence disorders, obstructive sleep apnea, or shift work disorder. In a further aspect, the central hypersomnolence disorder is selected from the group containing narcolepsy type 1 (with cataplexy), narcolepsy type 2, idiopathic hypersomnia, Kleine-Levin syndrome, hypersomnia due to a medical condition, hypersomnia due to a medication or substance, hypersomnia associated with a psychiatric condition, and/or insufficient sleep syndrome.

In some aspects, the one or more compositions of the present technology further comprise one or more excipients, wherein the excipients are selected from the group containing anti-adherents, binders, coatings, disintegrants, fillers, flavors, dyes, colors, glidants, lubricants, preservatives, sorbents, sweeteners, derivatives thereof, and/or combinations thereof.

In some aspects, the compositions of the present technology have a dosing regimen that is one time a day. In other aspects, the compositions of the present technology have a dosing regimen that is about two times a day.

In some aspects, the compositions of the present technology are orally administered to a human or an animal subject.

Another aspect of the present technology is at least one kit comprising a therapeutically effective amount of any one of the disclosed GHB delivering compounds or a pharmaceutically acceptable salt thereof, wherein the compound is in a unit dosage form, and instructions for the use thereof.

In some aspects, the unit dosage form is selected from the group containing a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a slurry, a sachet, a buccal tablet, and/or a suppository. In further aspects, the unit dosage form is selected from the group of transdermal patch, nasal spray, intramascular injection, depot injection, subcutaneous injection, and/or intravenous injection. In one aspect, the unit dosage forms can be packaged as a blisterpack or simular unit dosage delivery packaging or system.

In another aspect, the one or more kits of the present technology further comprise an additional therapeutic compound. In some aspects, the additional therapeutic compound is selected from the group containing amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, and/or solriamfetol, and combinations thereof. In a further aspect, the additional therapeutic compound is in a unit dosage form. In yet a further aspect, the unit dosage form is a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a slurry, a sachet, a buccal tablet, and/or a suppository.

In some aspects, the GHB delivering compound(s) is in a liquid dosage form, and the additional therapeutic compound is in an oral powder form or sachet form. In other aspects, the GHB delivering compound(s) and the additional therapeutic compound(s) can be in different combinatorial dosage forms including but not limited to capsule and thin film, or liquid and tablet.

In further aspects, the additional therapeutic compound is added to the liquid dosage form of the GHB delivering compound prior to administration.

In some aspects, the kit comprises instructions for use. In further aspects, the instructions for use include instructions for administration of at least one of the GHB delivering compounds, administration of at least one of the additional therapeutic compounds, and/or salt thereof or combinations thereof.

Another aspect of the present technology is an oral formulation comprising a therapeutically effective dose (e.g., for the treatment of a sleep disorder) of any one of the disclosed GHB delivering compounds or a pharmaceutically acceptable salt thereof.

In some aspects, the oral formulation further comprises one or more excipients, wherein the excipients are anti-adherents, binders, coatings, disintegrants, fillers, flavors, dyes, colors, glidants, lubricants, preservatives, sorbents, sweeteners, derivatives thereof, and/or combinations thereof. In another aspect, the therapeutically effective dose is in a unit dosage form. In a further aspect, the unit dosage form is a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a slurry, and/or a buccal tablet.

In some aspects, the oral formulation(s) has a dosing regimen that is about two times per day. In some aspects, the oral formulation(s) has a dosing regimen that is about one time a day. In another aspect, the oral formulation(s) is orally administered to a human or an animal subject.

In some aspects, the pharmaceutically acceptable salt is an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and/or a mixture thereof.

In other embodiments and aspects of the present technology, the pharmaceutically acceptable salt may be amphetaminium or serdexmethylphenidate.

Another aspect of the present technology is at least one method of preventing or treating a sleep disorder in a subject in need thereof, comprising administering to the subject a composition comprising a GHB delivering compound or a pharmaceutically acceptable salt of the compound from:

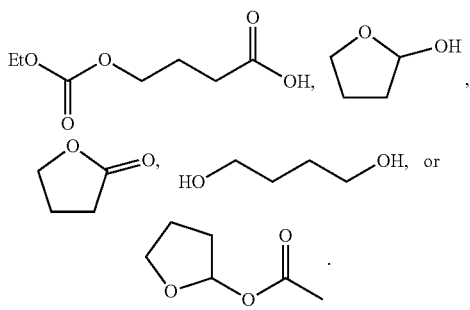

In some aspects of the method, the sleep disorder is a symptom of a degenerative neurological disease or disorder and/or is a side effect of treating a degenerative neurological disease or disorder with medication or a therapeutic compound. In another aspect, the degenerative neurological disease or disorder is Parkinson's disease, primary parkinsonism, paralysis agitans, and idiopathic parkinsonism.

In another aspect of the method, the composition further comprises amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, and solriamfetol, or combinations thereof.

In another aspect, the sleep disorder is excessive daytime sleepiness associated with central hypersomnolence disorders, obstructive sleep apnea, or shift work disorder. In another aspect, the central hypersomnolence disorder is narcolepsy type-1 (with cataplexy), narcolepsy type 2, idiopathic hypersomnia, Kleine-Levin syndrome, hypersomnia due to a medical condition, hypersomnia due to a medication or substance, hypersomnia associated with a psychiatric condition, insufficient sleep syndrome, and/or combinations thereof.

In some aspects of the method, the composition further comprises one or more excipients, wherein the excipients are anti-adherents, binders, coatings, disintegrants, fillers, flavors, dyes, colors, glidants, lubricants, preservatives, sorbents, sweeteners, derivatives thereof, and/or combinations thereof. In another aspect, the composition has a dosing regimen that is about two times a day. In another aspect, the composition has a dosing regimen that is one time a day. In some aspects, the composition is orally administered to a human or an animal subject.

Another aspect of the present technology is a kit comprising a therapeutically effective amount of any one of the disclosed compositions, wherein the composition is in a unit dosage form. In an aspect, the unit dosage form is a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a sachet, a slurry, a buccal tablet, and/or a suppository. In one aspect, the unit dosage forms can be packaged as a blisterpack or simular unit dosage delivery packaging or system.

In another aspect, the kit further comprises an additional therapeutic compound. In a further aspect, the additional therapeutic compound is amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, and/or solriamfetol, and combinations thereof. In yet a further aspect, the additional therapeutic compound is in a unit dosage form.

In another aspect, the unit dosage form is a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a sachet, a slurry, a buccal tablet, and/or a suppository.

In another aspect, the pharmaceutically acceptable salt is an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphorcarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and/or a mixture thereof.

In other embodiments, the pharmaceutically acceptable salt may be amphetaminium or serdexmethylphenidate.

BRIEF DESCRIPTION OF THE DRAWINGS

Various aspects of the present disclosure will now be described, by way of example only, with reference to the attached Figures, wherein.

DETAILED DESCRIPTION

Figure 1:
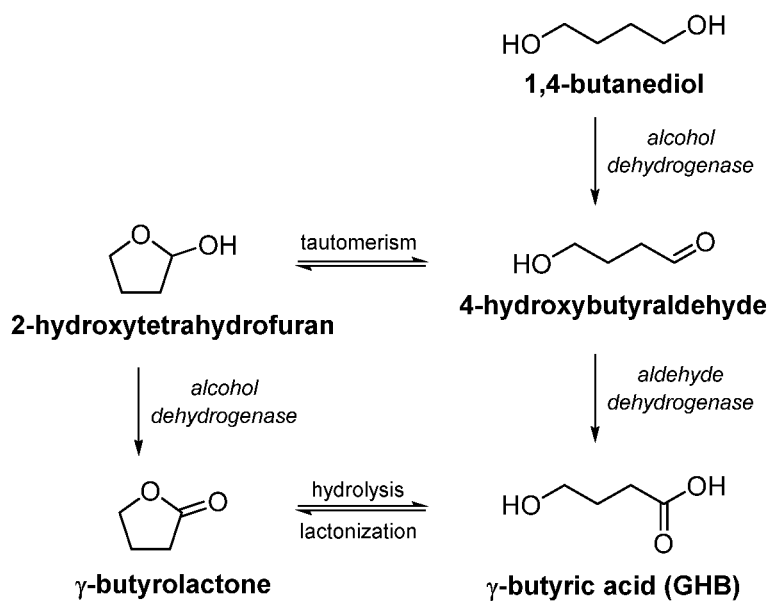
FIG. 1 depicts the metabolic pathways of 2-hydroxytetrahydrofuran and 1,4-butanediol to gamma-hydroxybutyrate.
Figure 2:
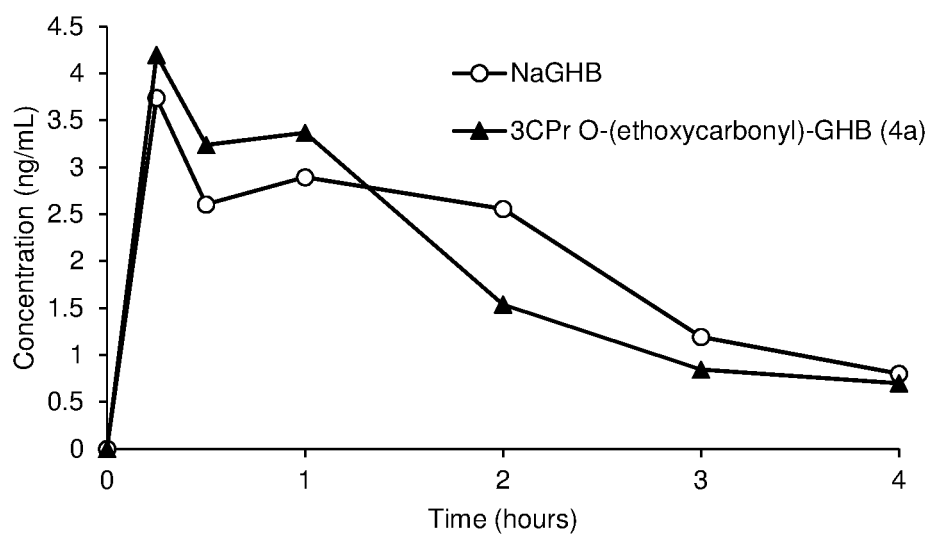
FIG. 2 shows the pharmacokinetic profile of NaGHB vs 3CPr O-(ethoxycarbonyl)-GHB (4a) after oral administration in rats (all doses were the molar equivalent of 70 mg/kg NaGHB).
Figure 3:
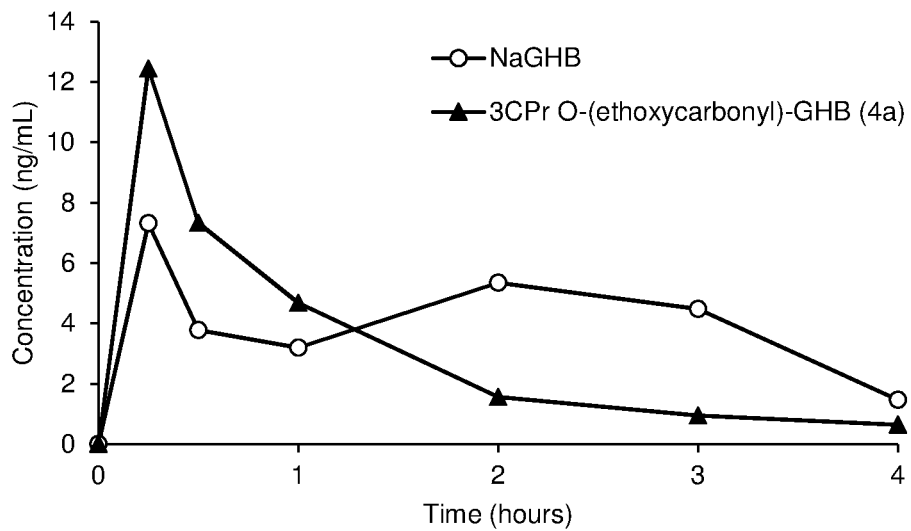
FIG. 3 shows the pharmacokinetic profile of NaGHB vs 3CPr O-(ethoxycarbonyl)-GHB (4a) after oral administration in rats (all doses were the molar equivalent of 100 mg/kg NaGHB).
Figure 4:
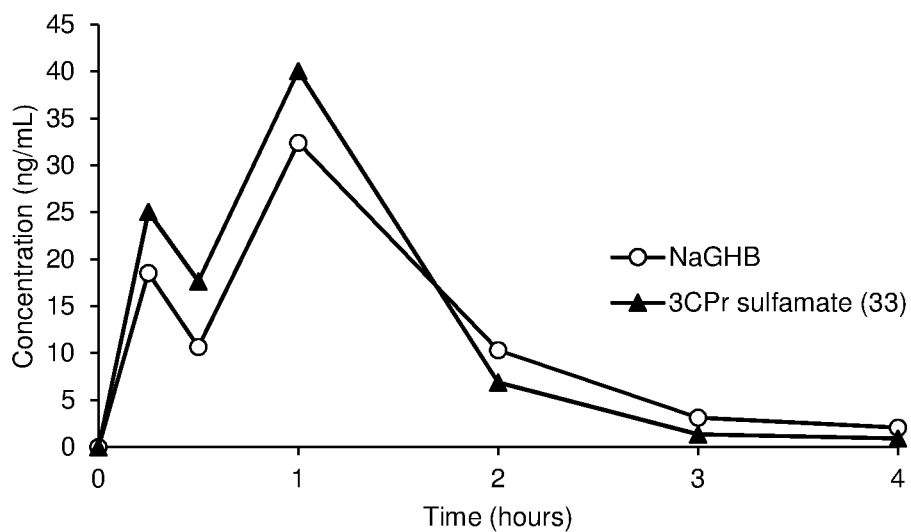
FIG. 4 shows the pharmacokinetic profile of NaGHB vs 3CPr sulfamate (33) after oral administration in rats (all doses were the molar equivalent of 100 mg/kg NaGHB).
Figure 5:
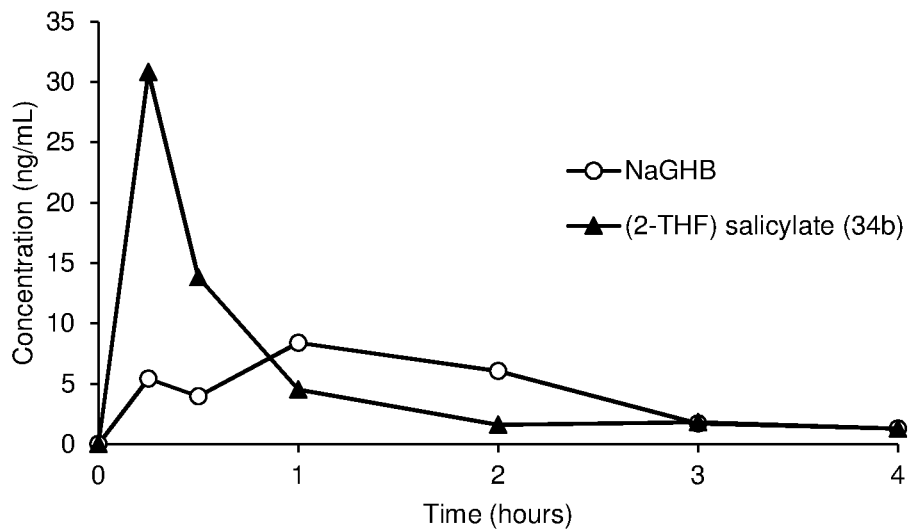
FIG. 5 shows the pharmacokinetic profile of NaGHB vs (2-THF) salicylate (34b) after oral administration in rats (all doses were the molar equivalent of 100 mg/kg NaGHB).
Figure 6:
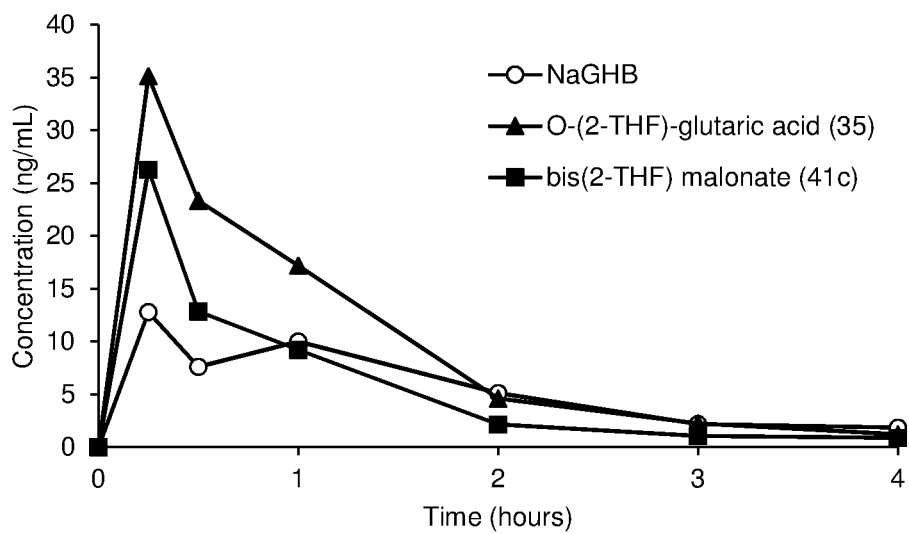
FIG. 6 shows the pharmacokinetic profile of NaGHB vs O-(2-THF)-glutaric acid (35) and bis(2-THF) malonate (41c) after oral administration in rats (all doses were the molar equivalent of 100 mg/kg NaGHB).
Figure 7:
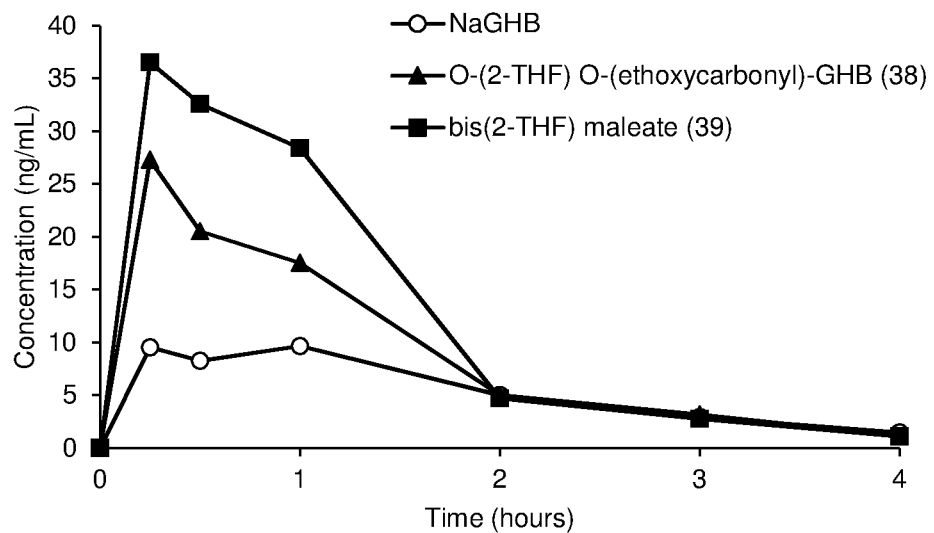
FIG. 7 shows the pharmacokinetic profile of NaGHB vs O-(2-THF) O-(ethoxycarbonyl)-GHB (38) and bis(2-THF) maleate (39) after oral administration in rats (all doses were the molar equivalent of 100 mg/kg NaGHB).
Figure 8:
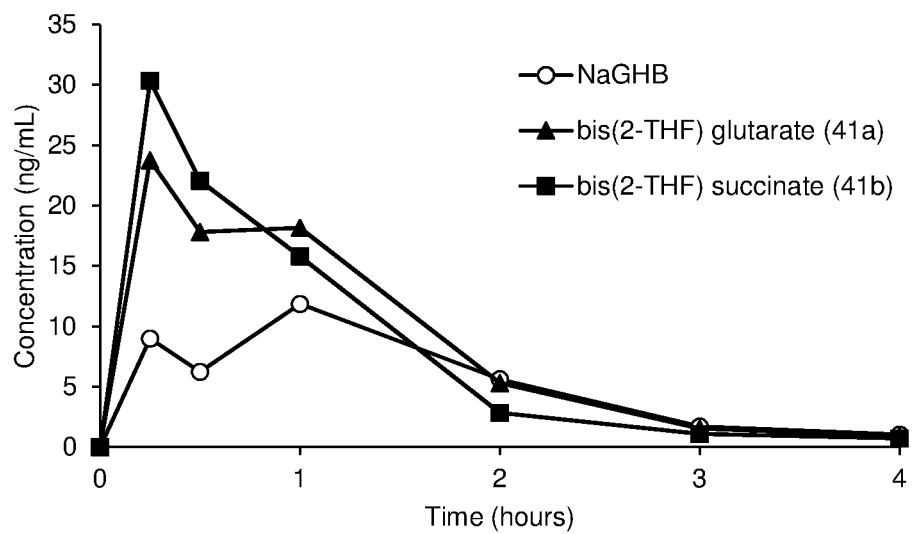
FIG. 8 shows the pharmacokinetic profile of NaGHB vs bis(2-THF) glutarate (41a) bis(2-THF) succinate (41b) after oral administration in rats (all doses were the molar equivalent of 100 mg/kg NaGHB).
Figure 9:
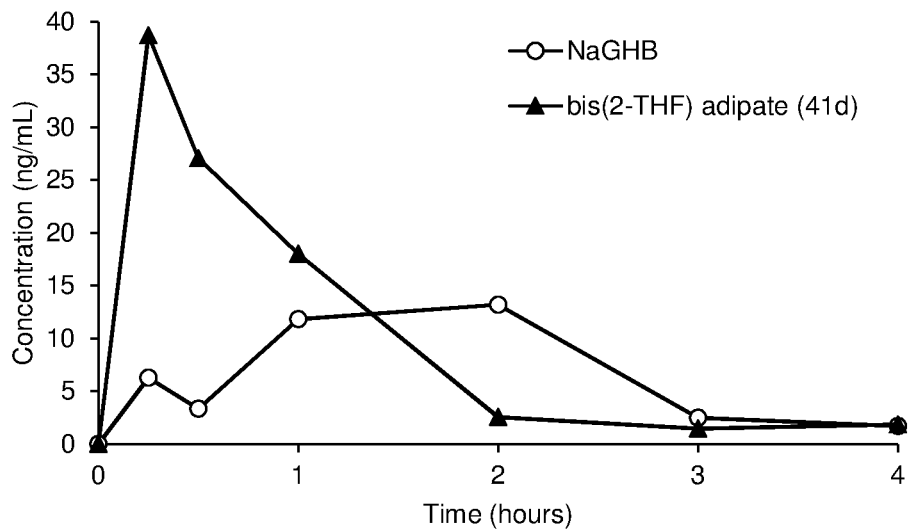
FIG. 9 shows the pharmacokinetic profile of NaGHB vs bis(2-THF) adipate (41d) after oral administration in rats (all doses were the molar equivalent of 100 mg/kg NaGHB).
Figure 10:
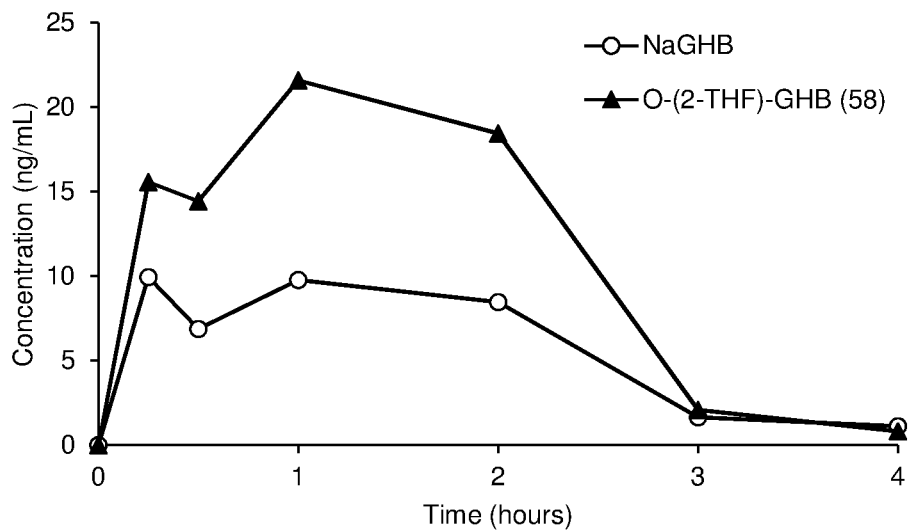
FIG. 10 shows the pharmacokinetic profile of NaGHB vs O-(2-THF)-GHB (58) after oral administration in rats (all doses were the molar equivalent of 100 mg/kg NaGHB).
Figure 11:
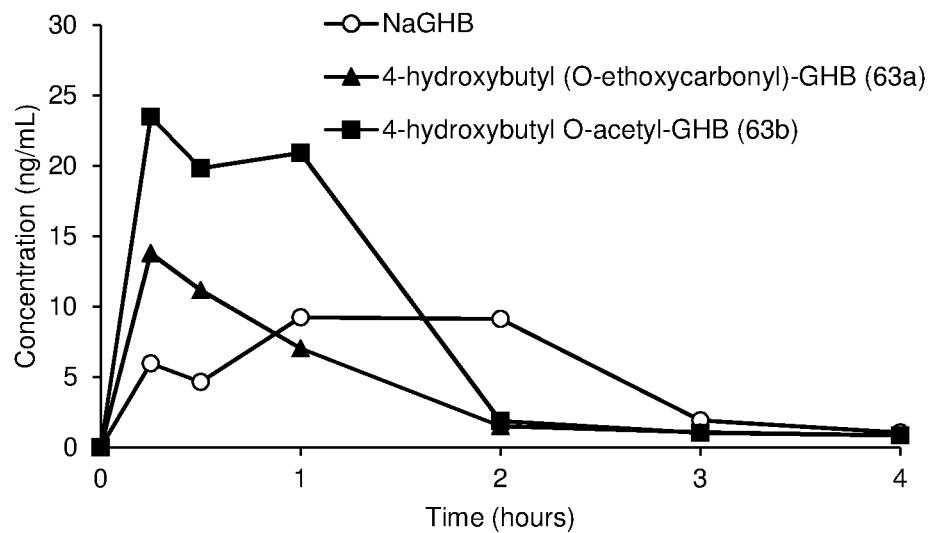
FIG. 11 shows the pharmacokinetic profile of NaGHB vs 4-hydroxybutyl (O-ethoxycarbonyl)-GHB (63a) and 4-hydroxybutyl O-acetyl-GHB (63b) after oral administration in rats (all doses were the molar equivalent of 100 mg/kg NaGHB).
Figure 12:
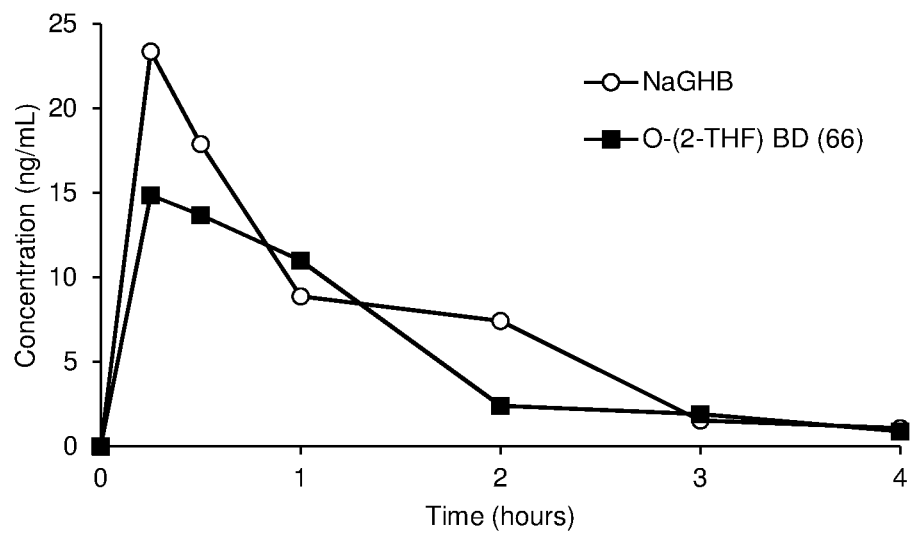
FIG. 12 shows the pharmacokinetic profile of NaGHB vs O-(2-THF) BD (66) after oral administration in rats (all doses were the molar equivalent of 80 mg/kg NaGHB).
Figure 13:
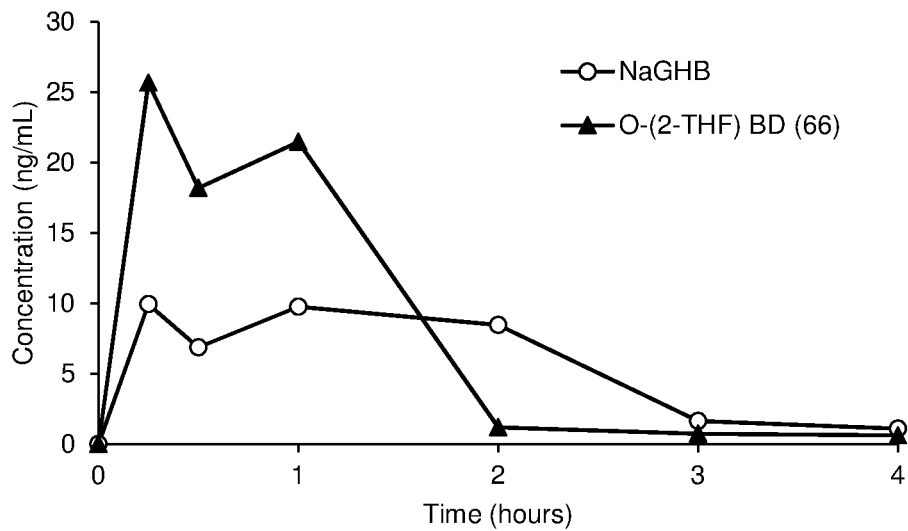
FIG. 13 shows the pharmacokinetic profile of NaGHB vs O-(2-THF) BD (66) after oral administration in rats (all doses were the molar equivalent of 100 mg/kg NaGHB).
Figure 14:
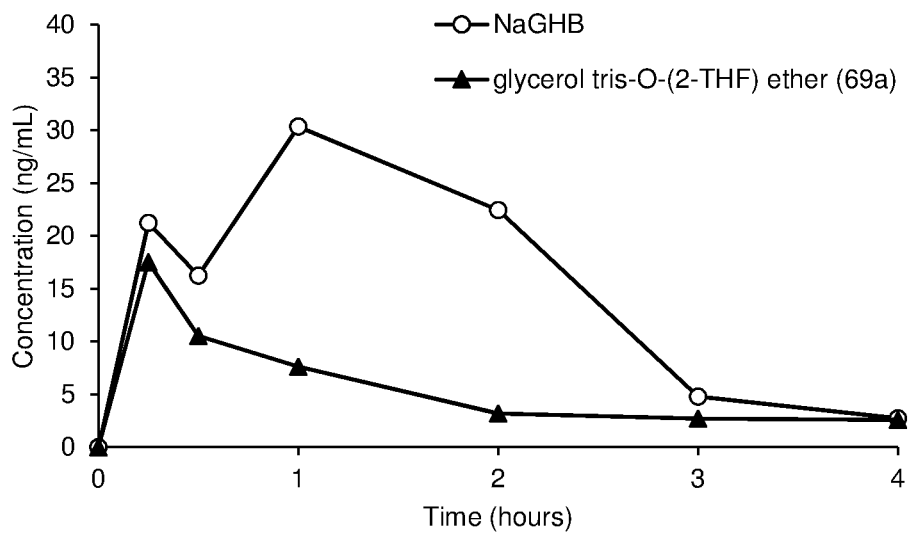
FIG. 14 shows the pharmacokinetic profile of NaGHB vs glycerol tris-O-(2-THF) ether (69a) after oral administration in rats (all doses were the molar equivalent of 100 mg/kg NaGHB).
Figure 15:
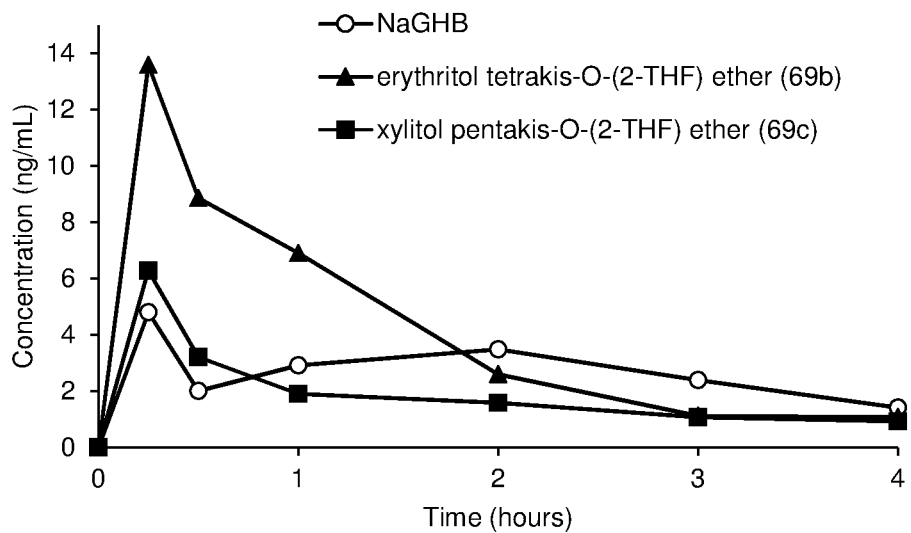
FIG. 15 shows the pharmacokinetic profile of NaGHB vs erythritol tetrakis-O-(2-THF) ether (69b) and xylitol pentakis-O-(2-THF) ether (69c) after oral administration in rats (all doses were the molar equivalent of 100 mg/kg NaGHB).
Figure 16:
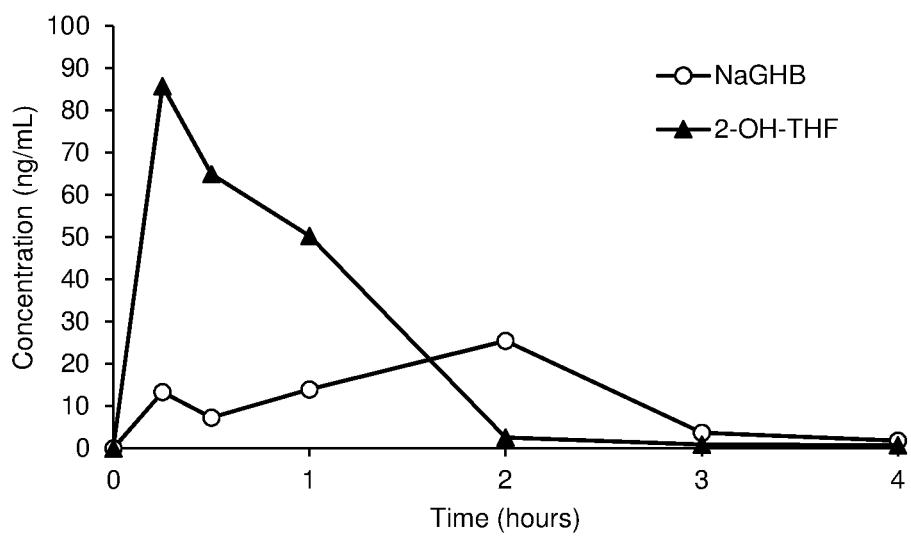
FIG. 16 shows the pharmacokinetic profile of NaGHB vs 2-OH-THF after oral administration in rats (all doses were the molar equivalent of 100 mg/kg NaGHB).
Figure 17:
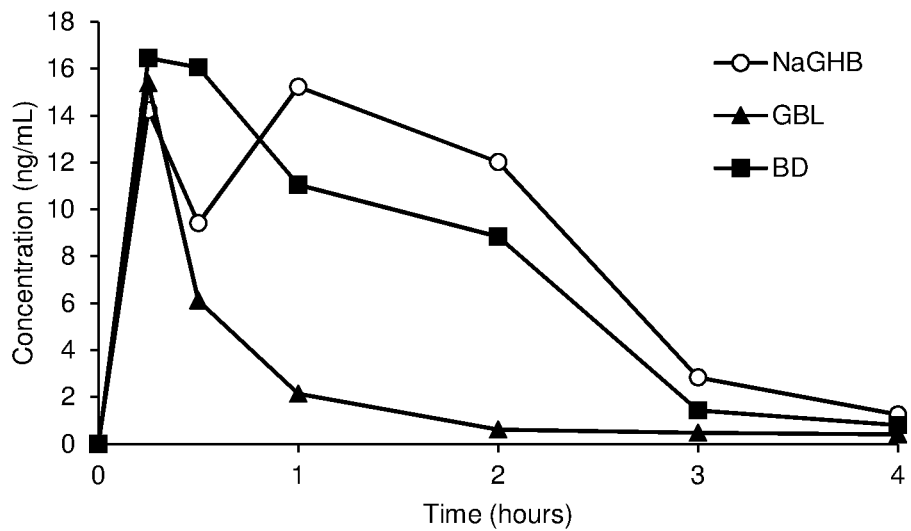
FIG. 17 shows the pharmacokinetic profile of NaGHB vs GBL and BD after oral administration in rats (all doses were the molar equivalent of 100 mg/kg NaGHB).
Figure 18:
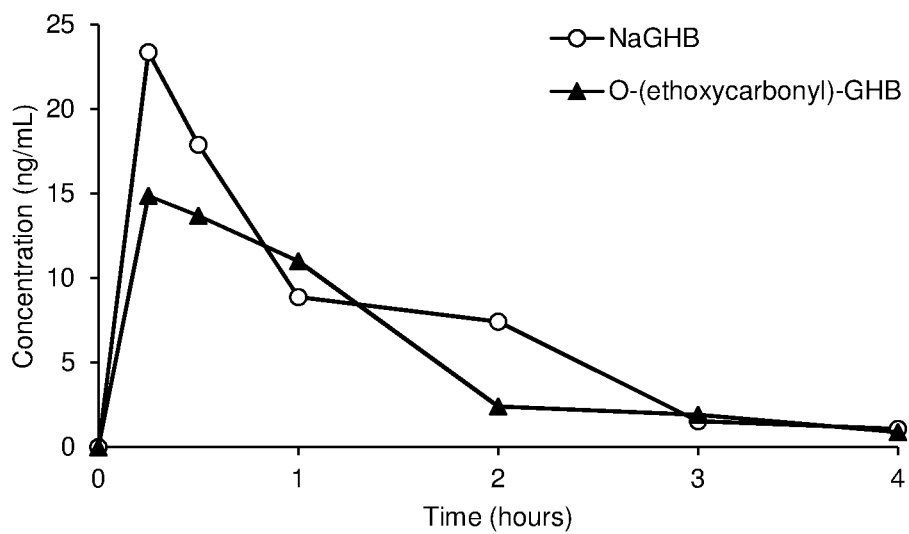
FIG. 18 shows the pharmacokinetic profile of NaGHB vs O-(ethoxycarbonyl)-GHB after oral administration in rats (all doses were the molar equivalent of 80 mg/kg NaGHB).

The present technology describes, in general, novel compounds and compositions that deliver gamma-hydroxybutyrate ("GHB") to a human or animal subject. In some aspects, these compounds have an increased bioavailabilty or a longer duration of action, or both, when compared to sodium gamma-hydroxybutyrate ("NaGHB"). In further aspects, due to their increased bioavailablity, the compounds of the present technology can be administered to a human or animal subject at a lower molar dose that is therapeutically equivalent when compared to NaGHB. These GHB delivering compounds are prodrugs or precursors of gamma-hydroxybutyrate, salts thereof, other derivatives thereof, and combinations thereof. The present technology also generally relates to methods of making these new compounds and compositions comprising the GHB delivering compounds, and kits thereof.

It is to be understood by those skilled in the relevant art that this disclosure is not limited to the particular methodology, protocols, and reagents described herein and as such may vary. It is also to be understood that the terminology used herein is for the purpose of describing particular embodiments only and is not intended to limit the scope of the present disclosure or the appended claims.

Unless otherwise defined, all technical and scientific terms used herein have the same meaning as commonly understood by one of ordinary skill in the art to which the methods described herein belong.

The singular form "a", "an" and "the" include plural referents unless the context clearly dictates otherwise. These articles refer to one or to more than one (i.e., to at least one). The term "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z".

The term "about" as used in connection with a numerical value throughout the specification and the claims denotes an interval of accuracy, familiar and acceptable to a person skilled in the art. In general, such interval of accuracy is +/−10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

The term "exemplary" means serving as a non-limiting example, instance, or illustration. As utilized herein, the terms "e.g.," and "for example" set off lists of one or more non-limiting aspects, examples, instances, or illustrations.

The use of the term "gamma-hydroxybutyrate", "7-hydroxybutyric acid" or "GHB" are synonymous and includes salt forms thereof.

The use of the term "GHB delivering compound" means a compound that is configured to deliver GHB to a human or animal subject. In some aspects, after administration, these compounds will be converted to GHB in the body.

In some aspects, the GHB delivering compounds comprise one or more chiral centers. In some embodiments, these chiral centers are part of the ligands and/or linkers attached to, for example, GHB, 2-OH-THF, or 1,4-butanediol resulting in chiral GHB delivering compounds. In further aspects, the compositions of these chiral GHB delivering compounds comprise a racemic mixture. In other aspects, the compositions comprising GHB delivering compounds are not in a racemic mixture. In still further aspects, the compositions comprising the one or more chiral GHB delivering compounds can be optically active mixtures, racemic mixtures, single stereoisomers, single enantiomers, mixtures of stereoisomers, mixtures of enantiomers, or combinations thereof.

The term "oxoacid" (i.e., oxyacids, oxo acids, oxy acids, oxiacids, oxacids) refers to a class of compounds that contain oxygen, at least one other element, and at least one hydrogen bound to oxygen, and which produce a conjugate base by loss of positive hydrogen ion(s) (protons).

"Amino acids" refers to organic compounds containing both a carboxyl (—COOH) and amino (—NH$_2$) group, and a variable side chain group. Amino acids that may be used in the present technology can be natural, standard, non-standard, unusual, synthetic, and/or essential amino acids, and can be an L-amino acid or a D-amino acid, or a combination thereof. Examples of amino acids for use in the practice of the present technology include, but are not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, homoarginine, citrulline, homocitrulline, homoserine, theanine, γ-aminobutyric acid, 6-aminohexanoic acid, sarcosine, carnitine, 2-aminoadipic acid, pantothenic acid, taurine, hypotaurine, lanthionine, thiocysteine, cystathionine, homocysteine, β-alanine, β-aminoisobutyric acid, β-leucine, β-lysine, β-arginine, β-tyrosine, β-phenylalanine, isoserine, β-glutamic acid, β-tyrosine, β-dopa (3,4-dihydroxy-L-phenylalanine), 2-aminoisobutyric acid, isovaline, di-N-ethylglycine, N-methyl-alanine, L-abrine, 4-hydroxyproline, 5-hydroxylysine, 3-hydroxyleucine, 4-hydroxyisoleucine, 5-hydroxy-L-tryptophan, 1-aminocyclopropyl-1-carboxylic acid, azetidine-2-carboxylic acid, pipecolic acid, allylglycine, cyclohexylglycine, N-(4-hydroxyphenyl)glycine, N-(chloroacetyl)glycline ester, 2-(trifluoromethyl)-phenylalanine, 4-(hydroxymethyl)-phenylalanine, 4-amino-phenylalanine, 2-chlorophenylglycine, 3-guanidino-propionic acid, 3,4-dehydro-proline, 2,3-diaminobenzoic acid, 2-amino-3-chlorobenzoic acid, 2-amino-5-fluorobenzoic acid, allo-isoleucine, tert-leucine, 3-phenylserine, isoserine, 3-aminopentanoic acid, 2-amino-octanedioic acid, 4-chloro-o-phenylalanine, β-homoproline, β-homoalanine, 3-amino-3-(3-methoxyphenyl)propionic acid, N-isobutyryl-cysteine, 3-amino-tyrosine, 5-methyl-tryptophan, 2,3-diaminopropionic acid, 5-aminovaleric acid, 4-(dimethylamino)cinnamic acid, 2-pyridylalanine (2-Pal), and 3-pyridylalanine (3-Pal).

As used herein, the term "prodrug" refers to a substance converted from an inactive form of a drug to an active drug in the body by a chemical or biological reaction. In an aspect of the present technology, the prodrug is a conjugate of at least one drug, GHB, and at least one ligand, for example. Thus, in an aspect of the present technology, the GHB delivering compounds are prodrugs.

As used herein, the term "ligand" refers to the part of the structure of the GHB delivering compound that is not the GHB or GHB precursor component.

As used herein, the term "precursor" refers to a substance that is converted into another substance by metabolic processes or biological reaction in the body. In an aspect of the present technology, the GHB delivering compound is a precursor, or a conjugate of a precursor and at least one ligand, for example. Thus, in an aspect of the present technology, the GHB delivering compound is a prodrug of a precursor. In an aspect of the present technology, the precursor is converted in the body to GHB ("GHB precursor"). In an aspect of the present technology, the precursor may be 2-hydroxytetrahydrofuran or 1,4-butanediol, for example.

As used herein "3CPr" means 3-carboxypropyl, "BD" means 1,4-butanediol or 1,4-dihydroxybutane, "2-THF" means tetrahydrofuran-2-yl or 2-tetrahydrofuranyl, "2-OH-THF" means 2-hydroxytetrahydrofuran, "Bn" means benzyl, "BOP" means benzotriazol-1-yloxytris(dimethylamino)phosphonium hexafluorophosphate, "DCC" means N,N'-dicyclohexylcarbodiimide, "DCM" means dichloromethane, "DIPEA" means N,N-diisopropylethylamine, "DMAP" means 4-dimethylaminopyridine, "DMF" means dimethylformamide, "HATU" means hexafluorophosphate azabenzotriazole tetramethyl uranium, "HOBt" means hydroxybenzotriazole, "HOSu" means N-hydroxysuccinimide, "HPLC" means high-performance liquid chromatography, "PPTS" means pyridinium p-toluene sulfonate, "TEA" means triethylamine, "TFA" means trifluoroacetic acid, "THF" means tetrahydrofuran, and "TLC" means thin-layer chromatography.

Prodrugs are often useful because, in some aspects, they may be easier to administer or process than the parent drug. For example, they may be more bioavailable by oral administration, whereas the parent drug is not. The prodrug may also have improved solubility and/or stability in pharmaceutical compositions over the parent drug. Although not wanting to be bound by any particular theory, it is envisaged that in at least one aspect, the GHB delivering compound is designed to be a prodrug of a precursor that upon release (or, when made available) is metabolized to GHB. In certain aspects, upon in vivo administration, a prodrug is chemically converted to the biologically, pharmaceutically, or therapeutically more active form of the compound. In certain aspects, a prodrug is enzymatically or chemically metabolized by one or more steps or processes to the biologically, pharmaceutically, or therapeutically more active form of the compound. Again, not wanting to be bound by any particular theory, to produce a prodrug, a pharmaceutically active compound is modified such that the active compound will be released/made available upon in vivo administration. The prodrug is designed to alter the metabolism, pharmacokinetics, or the transport characteristics of a drug in certain aspects, to reduce side-effects or toxicity, to increase tolerability, to improve tolerance, to improve bioavailability and/or water solubility, to improve the flavor of a drug, or to alter other characteristics or properties of a drug in other discrete aspects.

General Structures

In accordance with some aspects, the present technology provides GHB in a compound form. More specifically, the GHB delivering compound comprises at least one organic compound covalently bonded or attached to GHB, 2-OH-THF, and/or 1,4-butanediol. One general structure of the GHB delivering compound of the present technology can be represented by the following general Formula I:

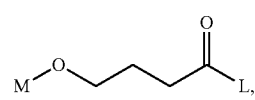

Formula I wherein L comprises at least one component selected from the group including hydroxyl, gamma-hydroxybutyrate, gamma-aminobutyric acid, 1,4-butanediol, 2-hydroxytetrahydrofuran, phosphate, sulfate, sulfamate, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amino acids, peptides, and/or salts thereof.

In some aspects, L comprises at least two of these components, alternatively at least three of these components, alternatively at least four of these components, or alternatively five or more of these components. The individual combinations of L are readily apparent to one of ordinary skill.

M comprises at least one component selected from the group including hydrogen, gamma-hydroxybutyrate, gamma-aminobutyric acid, 1,4-butanediol, 2-hydroxytetrahydrofuran, sugar alcohol, ethylene glycol, glycerol, erythritol, threitol, arabitol, xylitol, ribitol, mannitol, sorbitol, galactitol, fucitol, iditol, inositol, volemitol, isomalt, lactitol, maltotriitol, maltotetraitol, polyglycitol, phosphate, sulfate, sulfamate, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, nitro, polycycloalkenyl, polycycloalkenylalkyl, polycycloalkyl, polycycloalkylalkyl, polyethylene glycol, thiol, amino acids, peptides, salts thereof, and/or combinations thereof.

In some aspects, M comprises at least two of these components, alternatively at least three of these components, alternatively at least four of these components, or alternatively five or more of these components. The individual combinations of M are readily apparent to one of ordinary skill.

Specific compounds for Formula I include, but are not limited to

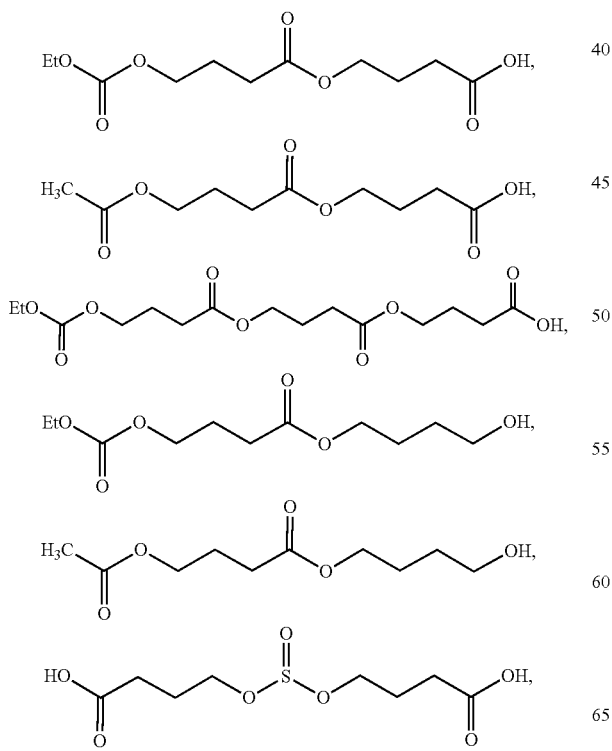

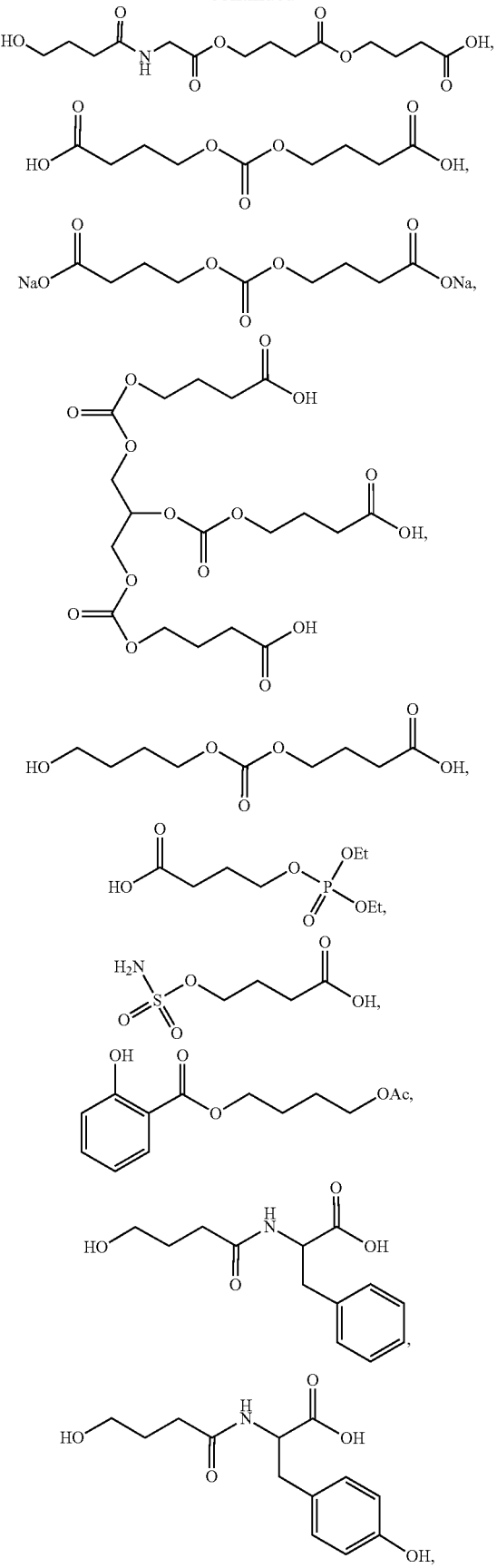

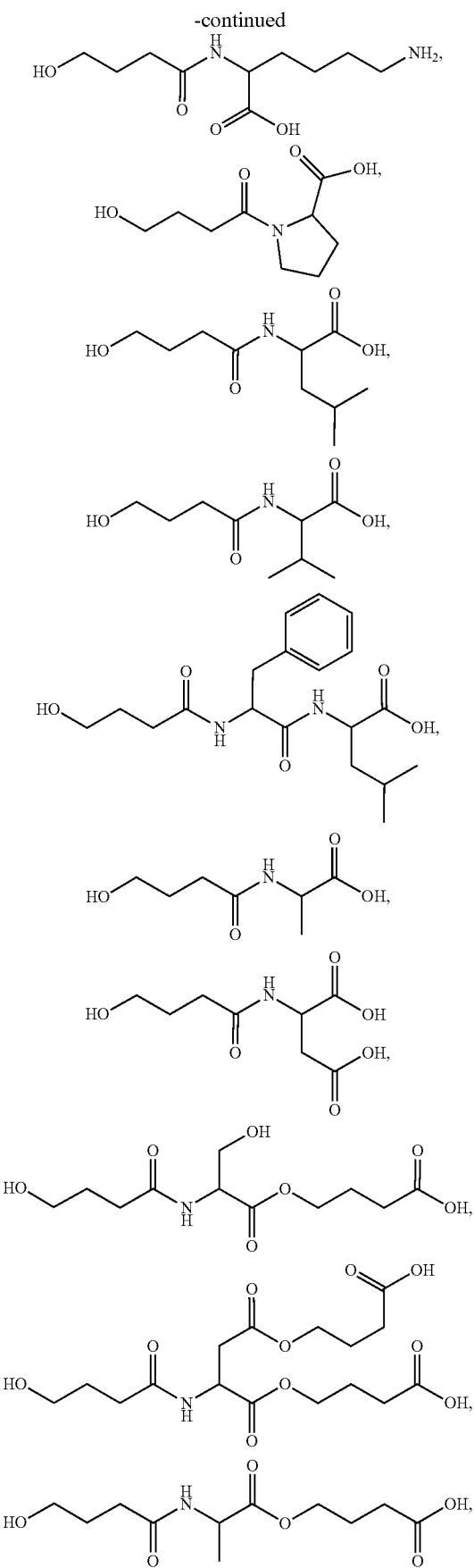

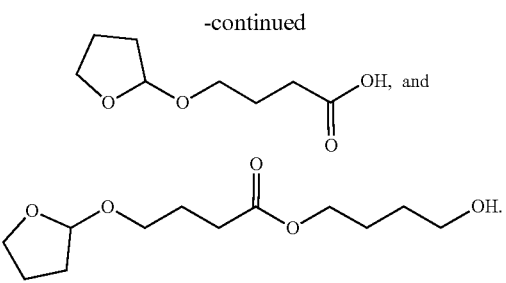

Another general structure of the GHB delivering compounds of the present technology can be represented by the following general structural Formula II:

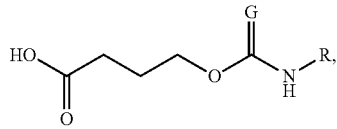

Formula II wherein G is S or O, and
R is selected from the group including

hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, polycycloalkenyl, polycycloalkenylalkyl, polycycloalkyl, polycycloalkylalkyl, polyethylene glycol, thiol, amino acids, peptides, salts thereof, and/or combinations thereof; and $R^1$ is an amino acid or a peptide.

Specific compounds for Formula II include, but are not limited to

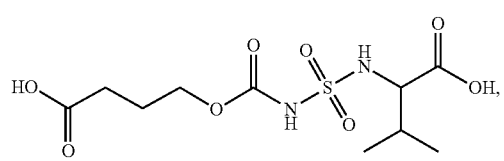

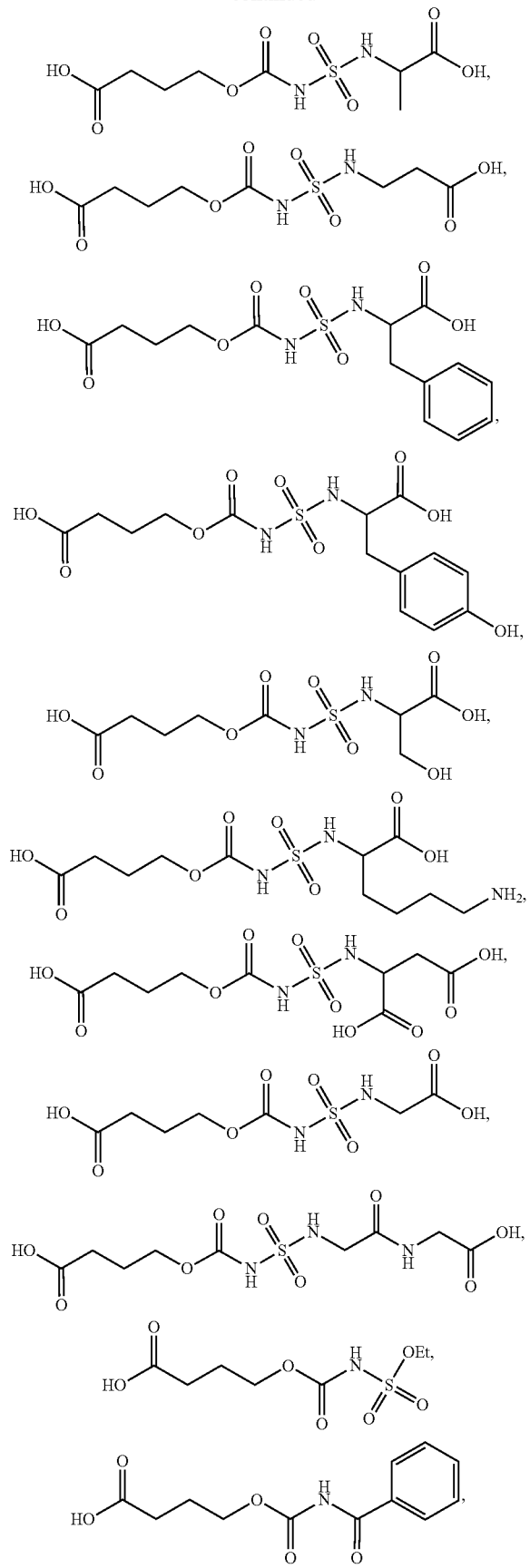

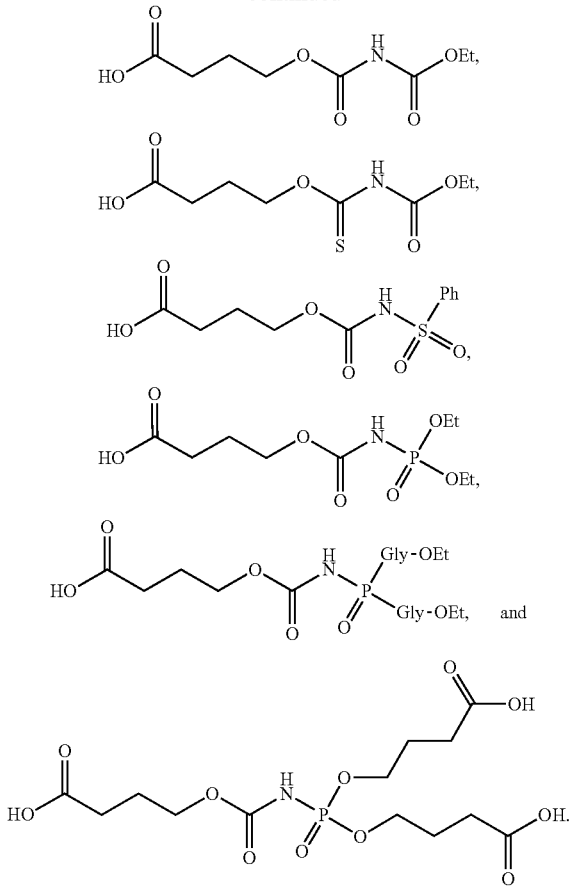

Another general structure of the GHB delivering compounds of the present technology can be represented by the following general structural Formula III:

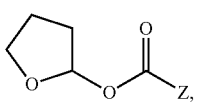

Formula III wherein Z comprises at least one component selected from the group including gamma-hydroxybutyrate, gamma-aminobutyric acid, 1,4-butanediol, 2-hydroxytetrahydrofuran, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, dicarboxylic acid, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, polycycloalkenyl, polycycloalkenylalkyl, polycycloalkyl, polycycloalkylalkyl, polyethylene glycol, thiol, amino acids, peptides, salts thereof, and/or combinations thereof.

In some aspects, Z comprises at least two of these components, alternatively at least three of these components, alternatively at least four of these components, or alternatively five or more of these components. The individual combinations of Z are readily apparent to one of ordinary skill.

Specific compounds for Formula III include, but are not limited to

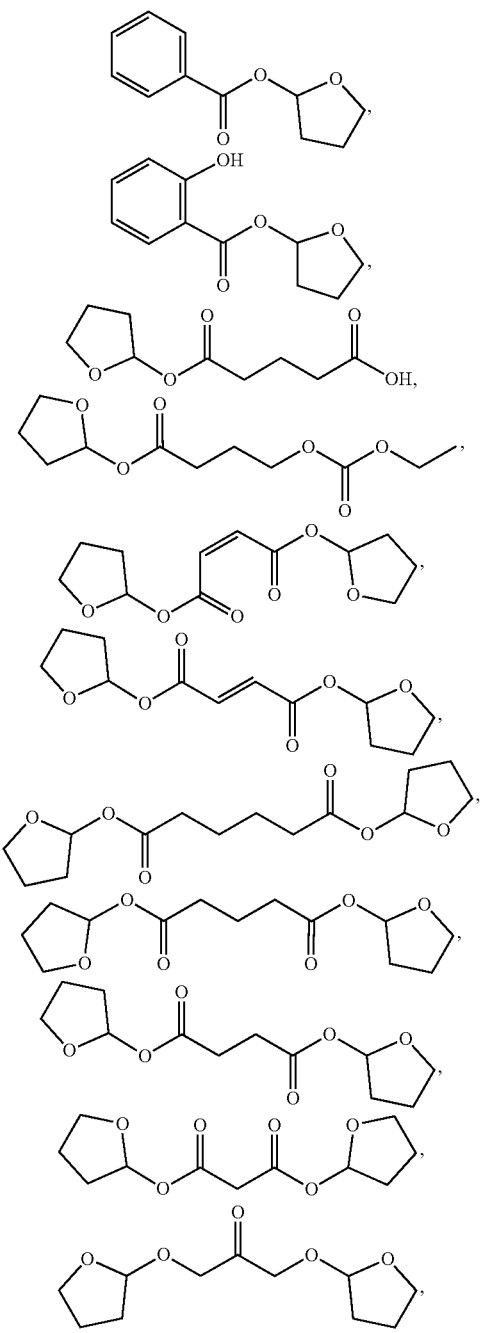

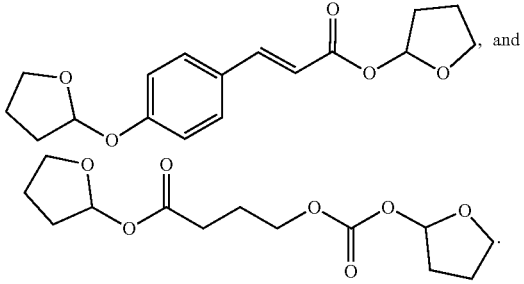

Another general structure of the GHB delivering compounds of the present technology can be represented by the following general structural Formula IV:

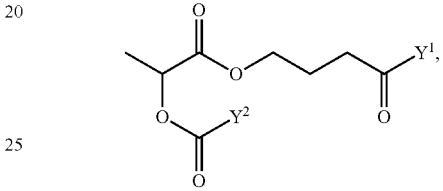

Formula IV wherein $Y^1$ and $Y^2$ are independently selected, for at least one (1) to five (5) times, from the group including hydroxyl, gamma-hydroxybutyrate, gamma-aminobutyric acid, 1,4-butanediol, 2-hydroxytetrahydrofuran, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, nitro, polycycloalkenyl, polycycloalkenylalkyl, polycycloalkyl, polycycloalkylalkyl, polyethylene glycol, thiol, amino acids, peptides, salts thereof, and/or combinations thereof.

In some aspects, each $Y^1$ and/or $Y^2$ is independently selected from the group/components listed in paragraph [0100] above at least two to at least five times. The independent selection applies within each $Y^1$ or $Y^2$ and also between $Y^1$ and $Y^2$. In some aspects, each $Y^1$ and/or $Y^2$ comprises at least two of these components, alternatively at least three of these components, alternatively at least four of these components, or alternatively five or more of these components, among others. The individual combinations of $Y^1$ and $Y^2$ are readily apparent to one of ordinary skill. For example, in one aspect, $Y^1$ comprises three components such as, for example, O-(2-THF)-GHB-GHB and $Y^2$ comprises two components such as, for example, BD-GHB.

Specific compounds for Formula IV include, but are not limited to

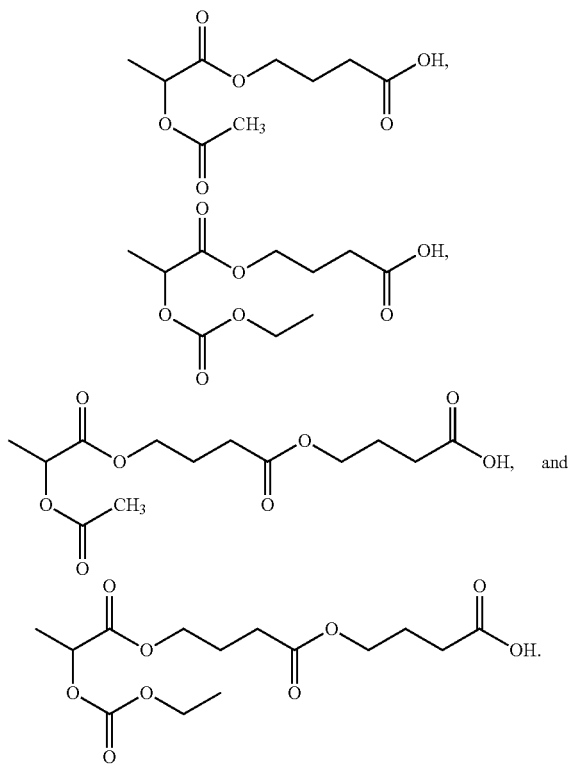

Another structure of the GHB delivering compounds of the present technology can be represented by the following general structural Formula V:

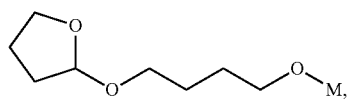

Formula V wherein M is selected from the group including hydrogen, 1,4-butanediol, 2-hydroxytetrahydrofuran, gamma-hydroxybutyrate, sugar alcohol, ethylene glycol, glycerol, erythritol, threitol, arabitol, xylitol, ribitol, mannitol, sorbitol, galactitol, fucitol, iditol, inositol, volemitol, isomalt, lactitol, maltotriitol, maltotetraitol, polyglycitol, gamma-aminobutyric acid, phosphate, sulfate, sulfamate, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, nitro, polycycloalkenyl, polycycloalkenylalkyl, polycycloalkyl, polycycloalkylalkyl, polyethylene glycol, thiol, amino acids, peptides, salts thereof, and/or combinations thereof.

In some aspects, M comprises at least two of these components, alternatively at least three of these components, alternatively at least four of these components, alternatively at least five of these components, alternatively at least six or more of these components, among others. The individual combinations of M are readily apparent to one of ordinary skill.

In further aspects, M comprises at least one sugar alcohol component and in addition, at least one hydroxytetrahydrofuran component, alternatively at least one sugar alcohol component and at least two hydroxytetrahydrofuran components, alternatively at least one sugar alcohol component and at least two hydroxytetrahydrofuran components, alternatively at least one sugar alcohol component and at least three hydroxytetrahydrofuran components, alternatively at least one sugar alcohol component and at least four hydroxytetrahydrofuran components, alternatively at least one sugar alcohol component and at least five hydroxytetrahydrofuran components, alternatively at least one sugar alcohol component and at least six or more hydroxytetrahydrofuran components, among others.

Specific compounds for Formula V include, but are not limited to

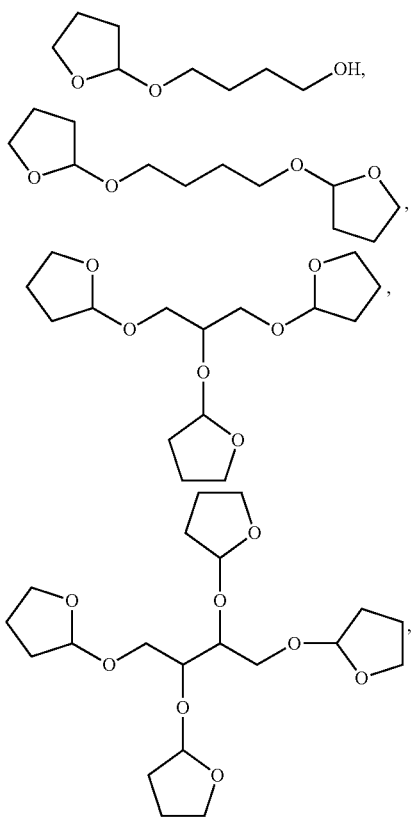

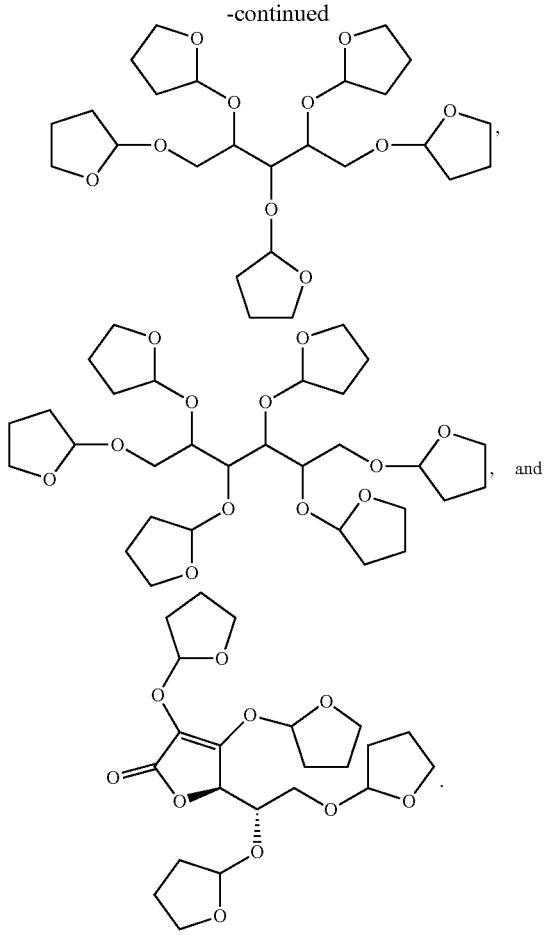

The GHB delivering compounds may also be present in salt forms. In some aspects, the pharmaceutically acceptable salt of the GHB delivering compound is a single salt or a mixed salt, where the one or more of the salts are selected from the group including an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and/or a mixture thereof.

In other embodiments, the pharmaceutically acceptable salt may be amphetaminium or serdexmethylphenidate.

The GHB delivering compounds of the present technology can be formulated into compositions for administration to a human or animal. The compositions may further comprise one or more excipients, wherein the excipients are selected from the group consisting of anti-adherents, binders, coatings, disintegrants, fillers, flavors, dyes, colors, glidants, lubricants, preservatives, sorbents, sweeteners, derivatives thereof, and/or combinations thereof.

Physiological Benefits

Although not wanting to be bound by any particular theory, it is believed that the above-defined GHB delivering compounds of the presently claimed and described technology can be given orally and, upon administration, release the active GHB or the GHB precursor after being hydrolyzed in the body. Since many of the phosphate, oxoacid, amino acid, and/or peptide components ("ligands") of this invention are naturally occurring metabolites or mimetics thereof, or pharmaceutically active compounds, these GHB delivering compounds can be easily recognized by physiological systems resulting in hydrolysis and release of GHB. The claimed compounds themselves have no or limited pharmacological activity and consequently may follow a metabolic pathway that differs from the pharmaceutically active GHB drug. By choosing suitable ligands, the release of GHB or GHB precursors into the systemic circulation can be controlled even when the GHB delivering compound is administered via routes other than oral.

In at least one embodiment, the GHB delivering compound(s) may release the GHB or GHB precursor similar to free or unmodified GHB/NaGHB or GHB precursor. In other embodiment(s), the GHB delivering compound(s) may release the GHB or GHB precursor(s) in a controlled or sustained manner, or extended manner. In yet another embodiment(s), some amount or portion of the dose of the GHB delivering compound administered to a human or animal subject provides a fast release of the GHB or GHB precursor(s), and some amount or portion of the same dose of the GHB delivering compound administered to a human or animal subject provides the GHB or GHB precursor(s) in a controlled or sustained manner, or extended manner. This can be achieved, for example, by designing a GHB delivering compound that is readily absorbed and has some, but not complete resistance to first-pass-metabolism. As a result, some amount or portion of the dose of the GHB delivering compound administered to a human or animal subject would release the GHB or GHB precursor(s) pre-systemically providing a fast rise in GHB or GHB precursor(s) blood concentrations, and some amount or portion of the same dose of the GHB delivering compound administered to a human or animal subject would be absorbed unchanged into the systemic circulation where it would slowly release the GHB or GHB precursor(s) in a controlled, sustained, or extended manner.

In a further embodiment(s), the composition comprising GHB delivering compounds of the present technology comprises at least two different GHB delivering compounds, wherein the at least one GHB delivering compound would release the GHB or GHB precursor(s) similar to free or unmodified GHB/NaGHB or GHB precursor(s) and the at least one other GHB delivering compound would release the GHB or GHB precursor(s) in a controlled or sustained manner, or extended manner.

In still another embodiment(s), the composition comprising the GHB delivering compound(s) of the present technology comprises unmodified GHB/NaGHB and at least one GHB delivering compound, wherein the unmodified GHB/NaGHB would provide fast onset of GHB blood concentrations and the at least one GHB delivering compound would release the GHB or GHB precursor(s) in a controlled or sustained manner, or extended manner.

Although not wanting to be bound by any particular theory, in at least one still further embodiment(s), it is believed that the controlled release of the GHB or GHB precursor(s) can potentially alleviate certain side-effects and improve upon the safety profile of the parent drug. These side-effects may include, for example, anxiety, balance disorder, bruxism, confusional state, decreased appetite, depressed mood, depression, diarrhea, dizziness, dry mouth, enuresis, fall, fatigue, feeling drunk, headache, hyperhidrosis, insomnia, irritability, muscle spasms, nausea, parasomnia, paresthesia, snoring, somnolence, tremor, vomiting, and decreased weight. In addition, GHB is also prone to substance abuse.

When the GHB or GHB precursor(s) is conjugated to certain ligands, the majority or at least some amount or portion of the resulting GHB delivering compound ("prodrug") is stable through the first-pass-metabolism process through the liver following oral administration. Again, not wanting to be bound by any particular theory, it is believed that in some aspects, the GHB delivering compound would subsequently release the GHB or GHB precursor(s) in a controlled, sustained, or extended manner in the systemic circulation. In other aspects, the GHB delivering compounds that can at least in part survive the first-pass-metabolism have improved bioavailability and/or are preferentially taken up in the brain when compared to unmodified GHB/NaGHB. As a result, these GHB delivering compounds of the presently described and claimed technology can be administered at lower molar doses with equivalent therapeutic effect when compared to unmodified GHB/NaGHB.

The disclosed GHB delivering compounds may be used to prevent or treat a sleep disorder, particularly sleep disorders that affect subjects with a degenerative neurological disease or disorder.

Additionally, other GHB related compounds may also be formulated into compositions and used to prevent or treat sleep disorders, such as sleep disorders that affect subjects with a degenerative neurological disease or disorder. These GHB related compounds may include, but are not limited to

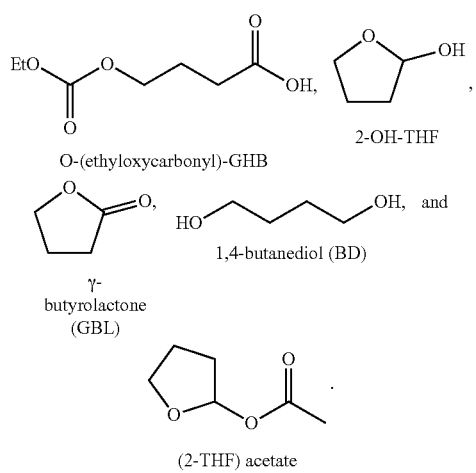

O-(ethyloxycarbonyl)-GHB

2-OH-THF

γ-butyrolactone (GBL)

1,4-butanediol (BD)

(2-THF) acetate

These sleep disorders include, but are not limited to, daytime sleepiness associated with central hypersomnolence disorders, obstructive sleep apnea, or shift work disorder. Non-limiting examples of central hypersomnolence disorders include narcolepsy type 1 (with cataplexy), narcolepsy type 2, idiopathic hypersomnia, Kleine-Levin syndrome, hypersomnia due to a medical condition, hypersomnia due to a medication or substance, hypersomnia associated with a psychiatric condition, and insufficient sleep syndrome.

Some sleep disorders including, for example, excessive daytime sleepiness, hypersomnolence, and hypersomnia may be caused by the primary symptoms of a degenerative neurological disease or disorder or may be a result of the treatment of the degenerative neurological disease or disorder. Non-limiting examples of degenerative neurological diseases or disorders include Parkinson's disease, primary parkinsonism, paralysis agitans, and idiopathic parkinsonism.

In some treatment regiments, the GHB delivering compounds or GHB related compounds prove particularly useful in providing improved sleep quality in a subject with sleep disorders during the night. Depending on the sleep disorder being prevented or treated, the GHB delivering compounds or GHB related compounds may be given in combination with one or more therapeutic compounds that improve wakefulness during the day. In a non-limiting example, these therapeutic compounds may be amphetamine, armodafinil, caffeine, mazindol, methylphenidate, modafinil, pitolisant, reboxetine, samelisant, serdexmethylphenidate, and solriamfetol, or combinations thereof.

In some treatment regiments, the GHB delivering compounds or GHB related compounds prove particularly useful in treating a sleep disorder in subjects suffering from Parkinson's disease, primary parkinsonism, paralysis agitans, and idiopathic parkinsonism. Depending on the sleep disorder being prevented or treated, the GHB delivering compounds or GHB related compounds may be given in combination with another therapeutic compound. In a non-limiting example, the therapeutic compound may be amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, and solriamfetol, or combinations thereof.

Additionally, depending on the treatment method, the composition can be dosed about two times a day, alternatively, at least about once a day. While the composition may be formulated to be administered orally, for example, as an oral formulation, it should be appreciated by one of ordinary skill in the relevant art that the composition can be formulated for any method of administration, including, but not limited to intravenous or intranasal administration.

The GHB delivering compounds, GHB related compounds, or compositions can also be provided as a kit, for example, a kit comprising a therapeutically effective amount of any one of the disclosed GHB delivering compounds or GHB related compounds. The kit may also include instructions for use and administration. The GHB delivering compounds or compositions may also be formulated into a unit dosage form. This allows for ease of administration as a kit may include one unit dosage form or multiple unit dosage forms. For example, if the GHB delivering compound in the kit is intended to be administered once per day for 30 days, the kit may include 30 individual unit dosage forms. The unit dosage forms may be, for example, a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a sachet, a slurry, a buccal tablet, and/or a suppository. In one aspect, the unit dosage forms can be packaged as a blisterpack or simular unit dosage delivery packaging or system.

In some aspects, the kit may include an additional therapeutic compound. For example, if the kit is intended to be used to treat sleep disorders that affect subjects with a degenerative neurological disease or disorder, the kit may further contain amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, solriamfetol, or combinations thereof.

In one aspect, the GHB delivering compound or GHB related compound is in a liquid dosage form and the additional therapeutic compound is in an oral powder form or sachet form.

In some aspects, the additional therapeutic compound is added to the liquid dosage form of the GHB delivering compound prior to administration. In some aspects, the unit dose of the GHB delivering compound may be a maximum tolerated dose. A maximum tolerated dose is the highest dose of a GHB delivering compound that does not cause unacceptable side effects. In these aspects, the GHB delivering compound may be provided in a liquid dosage form of at least about 5 mL, alternatively at least about 10 mL, alternatively at least about 25 mL, alternatively at least about 50 mL, alternatively at least about 75 mL, or alternatively at least about 100 mL. The additional therapeutic compound may then be added to the liquid dosage form, for example a bottle, and shaken to mix with the GHB delivering compound. A subject may then drink the combined dose from the liquid dosage form or pour into a glass, cup, or other delivery vessel.

In some aspects, the GHB delivering compound of the present technology is present in the composition in an amount that is the molar equivalent to a dose of NaGHB in the range of about 0.1 g to about 18 g per day, alternatively in the range of about 1 g to about 14 g per day, alternatively in the range of about 2 g to about 10 g per day, or alternatively in the range of about 4.5 g to about 9 g per day. It should be appreciated by one of skill in the art that the presently described technology and ranges herein include all sub-ranges (and sub-ranges within those sub-ranges) within the described ranges on a per day (i.e., 24 hours) basis and divided doses within that daily (24 hour) period of time. For example, 0.1 g to 0.2 g, to 0.3 g, to 0.4 g, to 0.5 g, to 0.6 g, to 0.7 g, to 0.8 g to 0.9 g, to 1.0 g, to 1.1 g, to 1.2 g, to 1.3 g, to 1.4 g, to 1.5 g, to 1.6 g, to 1.7 g, to 1.8 g, to 1.9 g, to 2.0 g, to 2.1 g, to 2.2 g, to 2.3 g, to 2.4 g, to 2.5 g, to 2.6 g, to 2.7 g, to 2.8 g, to 2.9 g, to 3.0 g, to 3.1 g, to 3.2 g, to 3.3 g, to 3.4 g, to 3.5 g, to 3.6 g, to 3.7 g, to 3.8 g, to 3.9 g, 4.0 g, to 4.1 g, to 4.2 g, to 4.3 g, to 4.4 g, to 4.5 g, to 4.6 g, 4.7 g, to 4.8 g, to 4.9 g, to 5.0 g, to 5.1 g, to 5.2 g, to 5.3 g, to 5.4 g, to 5.5 g, to 5.6 g, to 5.7 g, to 5.8 g, to 5.9 g, to 6.0 g, to 6.1 g, to 6.2 g, to 6.3 g, to 6.4 g, to 6.5 g, to 6.6 g, to 6.7 g, to 6.8 g, to 6.9 g, to 7.0 g to 7.1 g, to 7.2 g, to 7.3 g, to 7.4 g, to 7.5 g, to 7.6 g, to 7.7 g, to 7.8 g, to 7.9 g, to 8.0 g, to 8.1 g, to 8.2 g, to 8.3 g, to 8.4 g, to 8.5 g, to 8.6 g, to 8.7 g, to 8.8 g, to 8.9 g, 9.0 g, to 9.1 g, to 9.2 g, to 9.3 g, to 9.4 g, to 9.5 g, to 9.6 g, to 9.7 g, to 9.8 g, to 9.9 g, to 10.0 g, to 10.1 g, to 10.2 g, to 10.3 g, to 10.4 g, to 10.5 g, to 10.6 g, to 10.7 g, to 10.8 g, to 10.9 g, to 11.0 g, to 11.1 g, to 11.2 g, to 11.3 g, to 11.4 g, to 11.5 g, to 11.6 g, to 11.7 g, to 11.8 g, to 11.9 g, to 12.0 g, to 12.1 g, to 12.2 g, to 12.3 g, to 12.4 g, to 12.5 g, to 12.6 g, to 12.7 g, to 12.8 g, to 12.9 g, to 13.0 g, to 13.1 g, to 13.2 g, to 13.3 g, to 13.4 g, to 13.5 g, to 13.6 g, to 13.7 g, to 13.8 g, to 13.9 g, to 14.0 g, to 14.1 g, to 14.2 g, to 14.3 g, to 14.4 g, to 14.5 g, to 14.6 g, to 14.7 g, to 14.8 g, to 15.0 g, to 15.1 g, to 15.2 g, to 15.3 g, to 15.4 g, to 15.5 g, to 15.6 g, to 15.7 g, to 15.8 g, to 15.9 g, to 16.0 g, to 16.1 g, to 16.2 g, to 16.3 g, to 16.4 g, to 16.5 g, 16.6 g, to 16.7 g, to 16.8 g, to 16.9 g, to 17.0 g, 17.1 g, to 17.2 g, to 17.3 g, to 17.4 g, to 17.5 g, to 17.6 g, to 17.7 g, to 17.8 g, to 17.9 g, to 18.0 g, among others. It should also be appreciated that the present technology can be dosed as needed therapeutically in dosages ranging in measurements suitable thereof, for example, milligrams, grams, et cetera.

SYNTHETIC SCHEMES

The presently described technology and its advantages will be better understood by reference to the following synthetic schemes. These schemes are provided to describe specific aspects of the present technology. By providing these specific schemes, the applicants do not limit the scope and spirit of the present technology.

Synthesis of Benzyl O-Benzyl GHB (2)

Scheme 1. (a) TEA, DMAP, DCM; (b) BH$_3$•Me$_2$S, THF

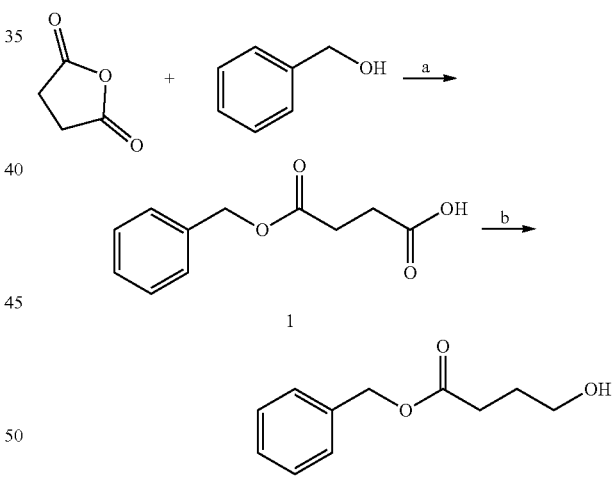

O-Benzyl-Succinic Acid (1)

To a stirred mixture of succinic anhydride (1 g, 10 mmol) in anhydrous DCM (10 mL) were added benzyl alcohol (1.2 g, 11 mmol), Et$_3$N (1.1 g, 11 mmol), and a catalytic amount of DMAP at room temperature. After stirring overnight, the reaction was diluted with 100 mL of DCM and further extracted with 5% aqueous NaHCO$_3$ solution (3×50 mL). The aqueous layer was acidified with 0.5 M HCl to pH 3 and extracted with EtOAc. The organic layer was dried over anhydrous Na$_2$SO$_4$, filtered, and then evaporated under vacuum to obtain compound 1 as white solid (1.58 g, 76%).

O-Benzyl GHB (2)

To a stirred solution of mono-benzyl succinate 1 (1 g, 4.8 mmol) in anhydrous THF (10 mL) was dropwise added borane dimethylsulfide (0.471 g, 6.24 mmol) at −20° C. The reaction was stirred at −20° C. for 1 h, followed by an additional 5 h at room temperature. The reaction was cooled down by placing it over an ice-bath and diluted with 150 mL of Et$_2$O. The ether layer was washed with K$_2$CO$_3$ solution, water, and brine. The organic layer was dried over anhydrous Na$_2$SO$_4$ and then evaporated under vacuum to obtain compound 2 as colorless viscous liquid (0.484 g, 52%).

Synthesis of 3CPr GHB Conjugates (4a-b)

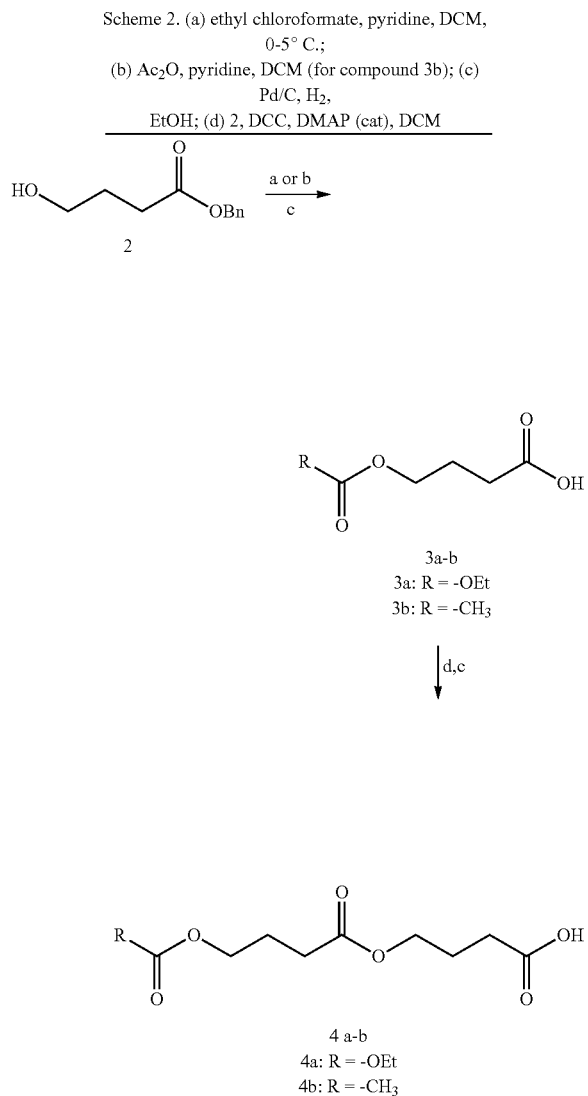

Scheme 2. (a) ethyl chloroformate, pyridine, DCM, 0-5° C.;
(b) Ac$_2$O, pyridine, DCM (for compound 3b); (c) Pd/C, H$_2$, EtOH; (d) 2, DCC, DMAP (cat), DCM

O-(Ethyloxycarbonyl)-GHB (3a)

A solution of ethyl chloroformate (0.615 mL, 6.42 mmol) in DCM (2 mL) was added to a solution of benzyl-4-hydroxy-butyrate 2 (1.00 g, 5.14 mmol) and pyridine (0.62 mL, 7.7 mmol) in DCM (10 mL) at 0-5° C. The reaction mixture was stirred for 2 hours at 0-5° C. Solvent was evaporated under reduced pressure. The residue was dissolved in EtOAc (100 mL), washed with 5% NH$_4$Cl and brine, dried over anhydrous Na$_2$SO$_4$, and evaporated to dryness to give benzyl O-(ethoxycarbonyl)-GHB as an oil (1.35 g, 99%).

A suspension of benzyl O-(ethoxycarbonyl)-GHB (1.3 g, 4.85 mmol), Pd/C (10% Pd, 0.75 g) in EtOH (25 mL) was stirred at room temperature under H$_2$ (balloon) for 1.5 hours. The reaction mixture was filtered through Celite®. The filtercake was washed with EtOH (2×10 mL). The combined filtrates were evaporated to dryness to give 3a as an oil in quantitative yield.

3CPR O-(Ethoxycarbonyl)-GHB (4a)

A solution of DCC (0.54 g, 2.62 mmol) in DCM (4 mL) was added dropwise to a solution of 3a (0.44 g, 2.5 mmol), 2 (0.49 g, 2.5 mmol) and DMAP (0.05 g) in DCM (10 mL) at 0-5° C. The reaction mixture was brought to room temperature and stirred for 3 hours. The precipitate was filtered and washed with DCM, and the combined filtrates were evaporated to dryness. The crude product was purified by preparative HPLC to give O-benzyl-3CPr O-(ethoxycarbonyl)-GHB as an oil (0.75 g, 85%).

A suspension of O-benzyl-3CPr O-(ethoxycarbonyl)-GHB (0.74 g, 2.1 mmol) and Pd/C (10% Pd, 0.4 g) in EtOH (15 mL) was stirred under H$_2$ (balloon) at room temperature for 1 hour. Reaction mixture was filtered through Celite®. The filtercake was washed with EtOH (2×5 mL). The combined filtrates were evaporated under reduced pressure and dried to give 4a as an oil (0.51 g, 92%)

O-Acetyl-GHB (3b)

To a solution of compound 2 (0.6 g, 3.09 mmol), pyridine (0.38 mL, 4.6 mmol) and DMAP (0.05 g) in DCM (10 mL) was added a solution of Ac$_2$O (0.36 mL, 3.86 mmol) in DCM (2 mL) dropwise at 0-5° C. After the addition, the reaction mixture was stirred at room temperature for 3 hours. The reaction was quenched with water and DCM was removed under reduced pressure. The residue was dissolved in EtOAc (100 mL), washed with 10% aqueous NH$_4$Cl, brine, dried over anhydrous Na$_2$SO$_4$ and evaporated to dryness to give benzyl O-acetyl-GHB (0.72 g, 98%) as an oil.

Compound 3b was synthesized in quantitative yield following the same procedure as described above for 3a.

3CPr O-Acetyl-GHB (4b)

3CPr O-acetyl-GHB 4b was synthesized following the same synthetic procedure as 4a, in 75% overall yield.

Synthesis of GHB-Gly-GHB-GHB (10)

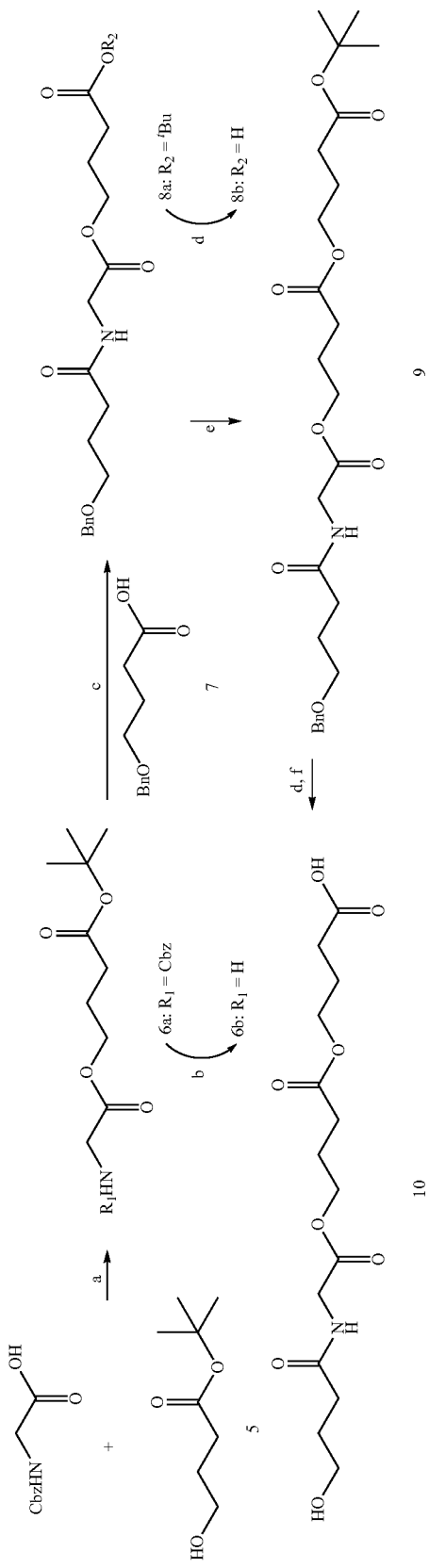

Cbz-Gly-GHB-$^t$Bu (6a)

To a stirred solution of benzyloxy(carbonyl)glycine (2 g, 9.56 mmol), HATU (4 g, 10.51 mmol) and DIPEA (6.2 g, 47.8 mmol) in 20 mL of anhydrous DMF was dropwise added tert-butyl 4-hydroxybutanoate 5 (1.53 g, 9.56 mmol) at room temperature under argon atmosphere. After stirring for 12 hours, the reaction was quenched by pouring over 5% aqueous bicarbonate solution. The aqueous layer was extracted with 3×50 mL of EtOAc. The organic layer was sequentially washed with water and brine, and dried over anhydrous $Na_2SO_4$. The organic layer was filtered and evaporated under vacuum and the residue was purified over silica gel (EtOAc:hexane, 1:4) to give compound 6a (2.64 g, 78%).

Gly-GHB-$^t$Bu (6b)

A solution of 6a (2.64 g, 7.5 mmol) in anhydrous EtOH (30 mL) was stirred under $H_2$ in the presence of Pd/C (1 g) at room temperature. After 2 h of stirring, the reaction was filtered through a pad of Celite®, and the filtrate was evaporated under vacuum to obtain compound 6b as a colorless viscous liquid in quantitative yield.

O-Benzyl-GHB-Gly-GHB-$^t$Bu (8a)

Compound 8a was obtained by adopting the procedure as described for 6a. Yield: 38%.

O-Benzyl-GHB-Gly-GHB (8b)

Compound 8a was treated with 30% TFA in DCM for 30 mins at room temperature. After completion of the reaction, the solvent was removed under vacuum to yield the desired product 8b as sticky solid which was used in the next step without further purification.

O-benzyl-GHB-Gly-GHB-GHB-$^t$Bu (9)

Compound 9 was synthesized by adopting the procedure as described above (for 6a).

GHB-Gly-GHB-GHB (10)

Deprotection of compound 9 first with 30% TFA in DCM, then catalytic hydrogenation afforded compound 10.

Synthesis of Bis(3CPr) Carbonate (13a-b)

Benzyl O4-Chlorocarbonyl-GHB (11)

A solution of triphosgene (3 g, 10.1 mmol) in toluene (10 mL) was cooled over an ice-water bath (0-5° C.). To this was dropwise added anhydrous pyridine (0.913 g, 11.6 mmol) under inert atmosphere. After 30 min. of stirring, benzyl 4-hydroxybutanoate (1.5 g, 7.7 mmol) was dropwise added to the reaction mixture. The ice-water bath was removed, and the reaction was stirred for an additional 1.5 hours. The reaction mixture was filtered and diluted with EtOAc. The organic layer was washed with water and dried over anhydrous $Na_2SO_4$. The EtOAc layer was filtered, and the filtrate was evaporated under vacuum to obtain chloroformate derivative 11 as a colorless oil, which was used in the next step without further purification.

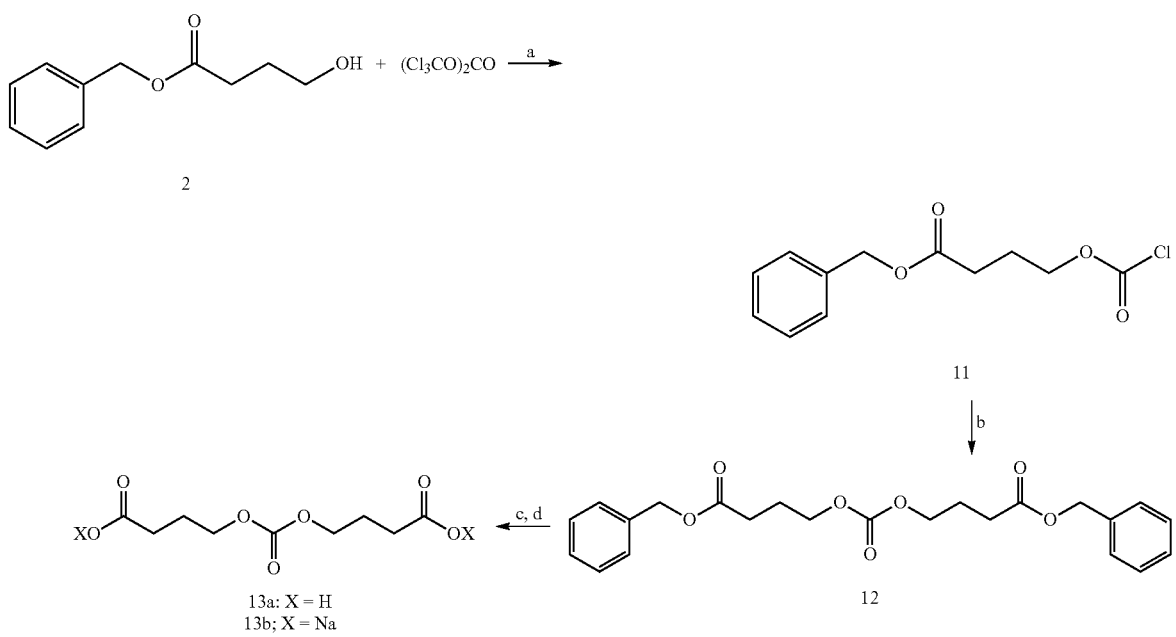

Scheme 4. (a) Triphosgene, pyridine, toluene; (b) 2, N-methyl imidazole; (c) 1,4-cyclohexadiene, Pd/C, MeOH; (d) $NaHCO_3$, water/$CH_3CN$ 13a: X = H
13b: X = Na

Bis(O-Benzyl-3CPr) Carbonate (12)

A solution of benzyl 4-hydroxybutanoate 2 (0.755 g, 3.89 mmol) in 3 mL of N-methyl imidazole was cooled over an ice-water bath (0-5° C.) under inert atmosphere. To this was dropwise added a solution of chloroformate 11 (1 g, 3.89 mmol) in DCM (2 mL). The ice-water bath was removed, and the reaction was run for an additional 2 hours. The reaction was quenched by diluting with EtOAc. The EtOAc layer was washed with water and dried over anhydrous $Na_2SO_4$. The organic layer was evaporated under vacuum, and the residue was purified over silica gel (hexane:EtOAc, 9:1) to obtain the desired product 12 as viscous liquid (1.2 g, 74%).

Bis(3CPr) Carbonate (13a)

To a stirred solution of dibenzyl 4,4'-(carbonylbis(oxy)) dibutyrate 12 (1.03 g, 2.49 mmol) in 20 mL of anhydrous methanol under inert atmosphere was added 1,4-cyclohexadiene (2 g, 24.9 mmol, 10 eq.), and 10% Pd/C (2 g). The precursor was found to be completely consumed by 90 min. as detected by TLC analysis. The suspension was filtered through a pad of Celite® and the filtrate was evaporated under vacuum to obtain desired compound 13a as waxy solid (0.54 g, 92%).

Bis(3CPr) Carbonate, Disodium (13b)

The acid 13a was converted to its sodium salt by treating with 2 eq. of $NaHCO_3$ solution. Lyophilization of the solution yielded the disodium salt 13b as white solid. Yield: quantitative.

Synthesis of 3CPr Carbonates

Scheme 5. (a) glycerol, pyridine, $CHCl_3$; (b) Pd/C, $H_2$, EtOH; (c) 4-benzyloxy butanol, pyridine, DCM

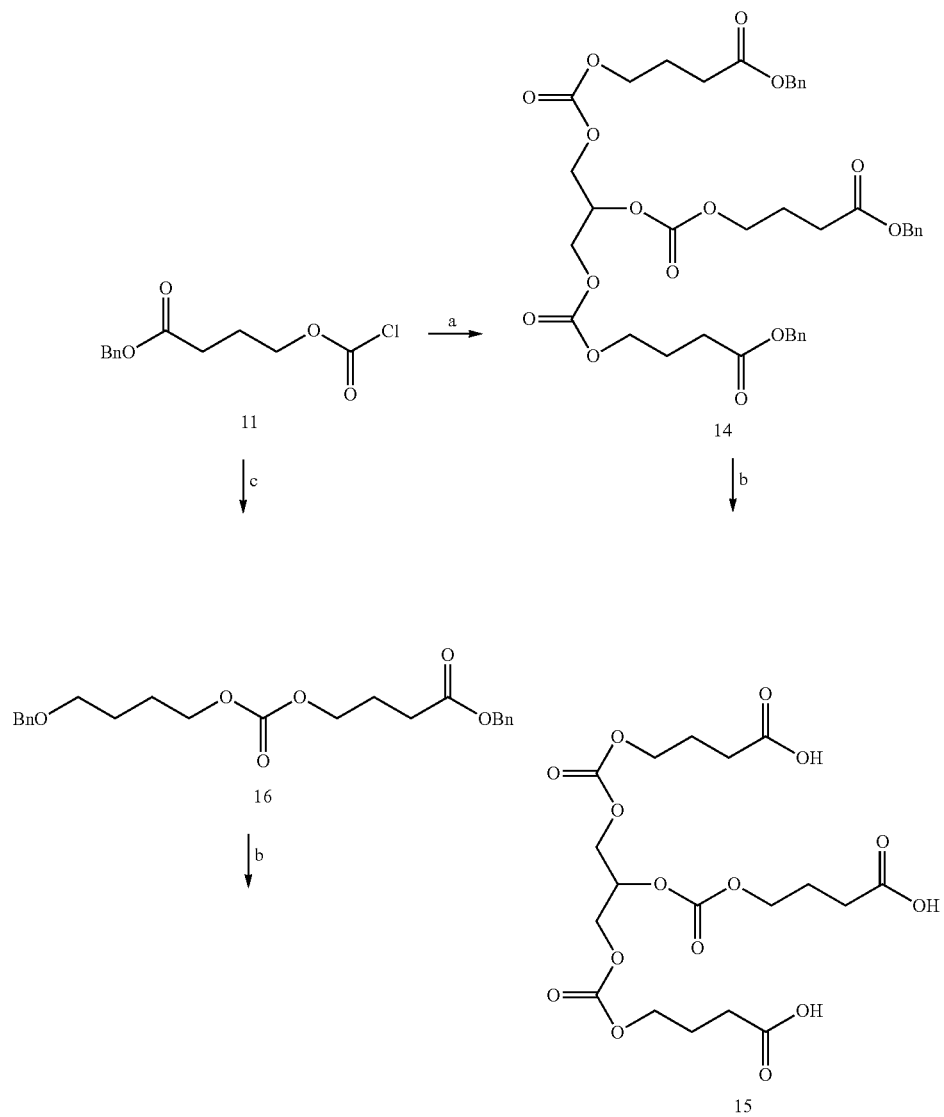

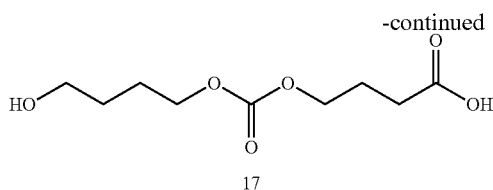

Glycerol Tris(O-Benzyl-3CPr Carbonate) (14)

To a solution of glycerol (0.103 g, 1.12 mmol) and pyridine (1 mL) in chloroform (9 mL) was added dropwise a solution of chloroformate 11 (1.024 g, 4 mmol) in CHCl$_3$ (2 mL) at 0-5° C. The reaction mixture was stirred for 5 hours at 0-5° C., quenched with water (a few drops) and evaporated under reduced pressure. The residue was dissolved in EtOAc (100 mL), washed with water, brine, dried over anhydrous Na$_2$SO$_4$ and concentrated. The crude product was purified by preparative HPLC to give the carbonate derivative 14 (0.42 g, 56%) as an oil.

Glycerol Tris(3CPr Carbonate) (15)

A suspension of compound 14 (0.4 g, 0.53 mmol), Pd/C (0.6 g) in MeOH/EtOH (1:1, 15 mL) was stirred at room temperature under H$_2$ (balloon) for 5 hours. The reaction mixture was filtered, washed with MeOH (3×5 mL) and the combined filtrates were evaporated under reduced pressure to give carbonate derivative 15 (0.22 g, 86%) as viscous oil.

O-Benzyl-4-Hydroxybutyl O-Benzyl-3CPr Carbonate (16)

To a solution of 4-benzyloxybutanol (0.27, 1.5 mmol) and pyridine (0.25 mL, 3 mmol) in DCM (8 mL) was added a solution of chloroformate 11 (0.385 g, 1.5 mmol) in DCM (2 mL) at 0° C. The reaction mixture was stirred for 3 hours at 0° C. Solvents were evaporated under reduced pressure. The residue was dissolved in EtOAc (80 mL), washed with water, brine, dried over Na$_2$SO$_4$ and evaporated to dryness. The crude product was purified by preparative HPLC to give the carbonate derivative 16 (0.41 g, 68%) as an oil.

4-Hydroxybutyl 3CPr Carbonate (17)

A suspension of 16 (0.41 g, 1.02 mmol), Pd/C (0.4 g) in EtOH (15 mL) was stirred at room temperature under H$_2$ (balloon) for 4 hours. The reaction mixture was filtered, washed with EtOH (2×5 mL) and the combined filtrates were evaporated under reduced pressure to give 4-hydroxybutyl 3CPr carbonate 17 (0.21 g, 93%) as oil.

Synthesis of Sulfonyl 3CPr Carbamates (19a-j and 21)

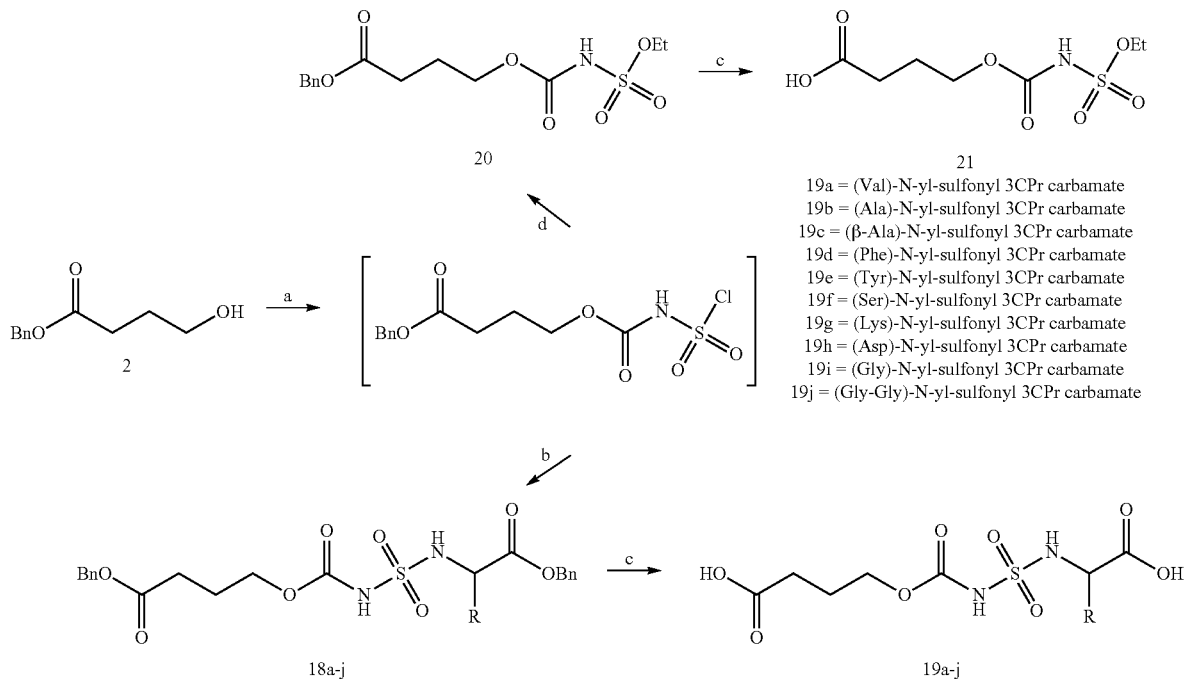

Scheme 6. DCM, 0-5° C.; (b) TEA, benzyl protected amino acids, DCM, 0-5° C.; (c) Pd/C, H$_2$, EtOH; (d) NH$_3$/EtOH 19a = (Val)-N-yl-sulfonyl 3CPr carbamate
19b = (Ala)-N-yl-sulfonyl 3CPr carbamate
19c = (β-Ala)-N-yl-sulfonyl 3CPr carbamate
19d = (Phe)-N-yl-sulfonyl 3CPr carbamate
19e = (Tyr)-N-yl-sulfonyl 3CPr carbamate
19f = (Ser)-N-yl-sulfonyl 3CPr carbamate
19g = (Lys)-N-yl-sulfonyl 3CPr carbamate
19h = (Asp)-N-yl-sulfonyl 3CPr carbamate
19i = (Gly)-N-yl-sulfonyl 3CPr carbamate
19j = (Gly-Gly)-N-yl-sulfonyl 3CPr carbamate

O-Benzyl-(Val)-N-yl-Sulfonyl O-Benzyl-3CPr Carbamate (18a)

To a solution of benzyl-4-hydroxy butyrate 2 (0.3 g, 1.55 mmol) in DCM (10 mL) was added chlorosulfonyl isocyanate (0.135 mL, 1.55 mmol) in DCM (1 mL) at 0° C. After stirring for 1 hour at 0° C., Val-OBn-HCl (0.38 g, 1.55 mmol) and TEA (0.54 mL, 3.9 mmol) were added, and the reaction mixture was stirred for 1.5 h at 0° C. The reaction was quenched with water (a few drops) and solvent was evaporated under reduced pressure. The residue was dissolved in EtOAc (120 mL), washed with 2% NaHSO₄ (70 mL), brine, dried over anhydrous Na₂SO₄ and evaporated to dryness to give 18a (0.71, 90%) as an oil.

(Val)-N-yl-Sulfonyl 3CPr Carbamate (19a)

A suspension of 18a (0.7 g, 1.38 mmol), Pd/C (0.65 g) in EtOH (25 mL) was stirred at room temperature under H₂ (balloon) for 3 hours. The reaction mixture was filtered through Celite®, washed with EtOH (2×10 mL), the combined filtrates were evaporated under reduced pressure and dried to give 19a as white solid (0.43 g, 95%).

(Amino acid)-N-yl-Sulfonyl 3CPr Carbamates (19b-j)

(Ala)-N-yl-sulfonyl 3CPr carbamate (19b), (β-Ala)-N-yl-sulfonyl 3CPr carbamate (19c), (Phe)-N-yl-sulfonyl 3CPr carbamate (19d), (Tyr)-N-yl-sulfonyl 3CPr carbamate (19e), (Ser)-N-yl-sulfonyl 3CPr carbamate (19f), (Lys)-N-yl-sulfonyl 3CPr carbamate (19g), (Asp)-N-yl-sulfonyl 3CPr carbamate (19h), (Gly)-N-yl-sulfonyl 3CPr carbamate (19i), and (Gly-Gly)-N-yl-sulfonyl 3CPr carbamate (19j) were synthesized following the same synthetic procedure as described for 19a.

Ethoxysulfonyl O-Benzyl-3CPr Carbamate (20)

To a solution of benzyl-4-hydroxy butyrate 2 (0.29 g, 1.49 mmol) in DCM (10 mL) was added chlorosulfonyl isocyanate (0.135 mL, 1.49 mmol) at 0-5° C. After stirring for 1.5 h at 0-5° C., ethanolic ammonia (2M, 1.5 mL) was added and the reaction mixture was stirred for 2 h at 0-5° C. Solvents were evaporated under reduced pressure. The residue was dissolved in EtOAc (100 mL), washed with brine, dried over anhydrous Na₂SO₄ and evaporated to dryness. The crude product was purified by preparative HPLC to give 20 (0.24 g, 47%) as an oil.

Ethoxysulfonyl 3CPr Carbamate (21)

Compound 20 was deprotected following the same procedure as described for 18a to give the title compound 21 as an oil.

Synthesis of Acyl 3CPr Carbamates (23a-b)

Scheme 7. (a) Benzoyl isocyanate, DCM; (b) Ethoxycarbonyl isocyanate, DCM; (c) Pd/C, H₂, EtOH

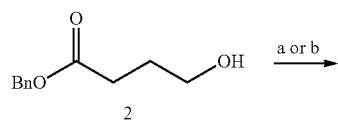

2

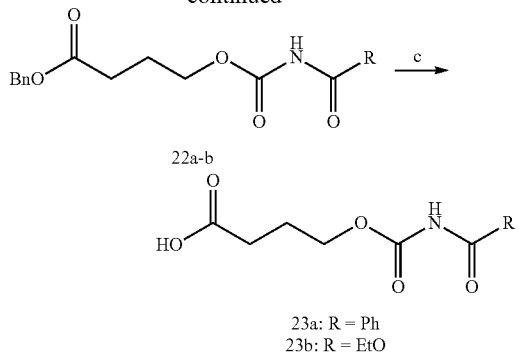

22a-b

23a: R = Ph
23b: R = EtO

Benzoyl O-Benzyl-3CPr Carbamate (22a)

To a solution of benzyl-4-hydroxy butanoate 2 (0.29 g, 1.5 mmol) in DCM (8 mL) was added a solution of benzoyl isocyanate (0.25 g, 1.7 mmol) in DCM at 0-5° C. The reaction mixture was stirred for an additional 1 h at 0-5° C. and then quenched with water (few drops). Solvent was evaporated under reduced pressure. The residue was dissolved in EtOAc (75 mL), washed with water, brine, dried over Na₂SO₄ and evaporated to dryness. The crude product was purified by preparative HPLC to give 22a as an oil (0.45 g, 88%).

Benzoyl 3CPr Carbamate (23a)

A suspension of compound 22a (0.45 g, 1.31 mmol), Pd/C (0.25 g, 10% Pd) in EtOH (15 mL) was stirred under H₂ (balloon) at room temperature for 2.5 hours. The reaction mixture was filtered through Celite®. The filtercake was washed with EtOH (2×8 mL) and the combined filtrates were evaporated under reduced pressure to give 23a (0.32 g, 97%) as white solid.

N-(Ethoxycarbonyl) 3CPr Carbamate (23b)

Compound 23b was synthesized following the same procedure as described for 23a, as a white solid in 71% overall yield.

Synthesis of N-(Ethoxycarbonyl) 3CPr Thiocarbamate (25)

Scheme 8. (a) EtOC(O)NCS, TEA, DCM; (b) Pd/C, H₂, EtOH

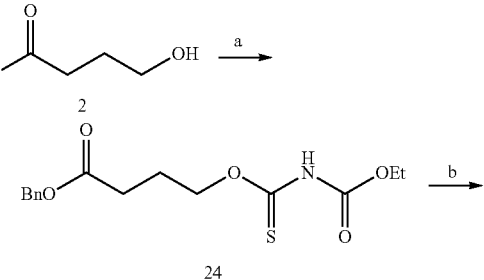

24

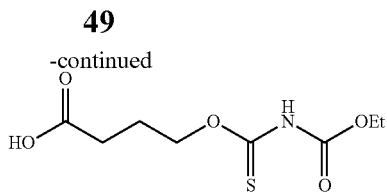

25

N-(Ethoxycarbonyl)O-Benzyl-3CPr Thiocarbamate (24)

To a solution of benzyl-4-hydroxybutanoate 2 (0.72 g, 3.7 mmol) and TEA (0.82 mL, 5.9 mmol) in DCM (10 mL) was added ethoxycarbonyl isothiocyanate (0.56 mL, 4.8 mmol) at 0-5° C. The mixture was stirred for 3 h 0-5° C. the reaction was quenched with water (few drops) and solvent was evaporated to dryness. The residue was dissolved in EtOAc (100 mL), washed 10% aq. $NH_4Cl$ (50 mL), brine, dried over $Na_2SO_4$ and evaporated to dryness. The crude product was purified by preparative HPLC to give compound 24 as an oil (0.35 g, 29%).

N-(Ethoxycarbonyl) 3CPr Thiocarbamate (25)

Deprotection of 24 under catalytic hydrogenation as described before afforded compound 25 in 98% yield.

Synthesis of Phenylsulfonyl 3CPr Carbamate (27)

Scheme 9. (a) PhC(O)NCO, DCM; (b) Pd/C, H₂, EtOH

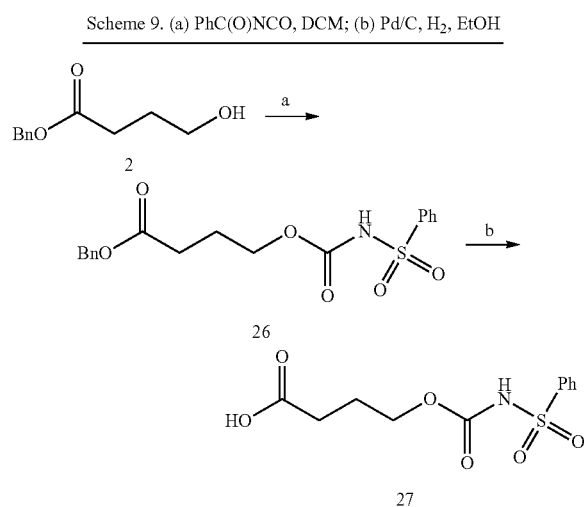

Phenylsulfonyl O-Benzyl-3CPr Carbamate (26)

To a solution of benzyl-4-hydroxy butanoate 2 (0.41 g, 2.1 mmol) in DCM (10 mL) was added a solution of benzenesulfonyl isocyanate (0.35 mL, 2.6 mmol) in DCM (2 mL) at 0-5° C. The reaction mixture was stirred at 0-5° C. for an additional 2 h, quenched with water (few drops) and solvent was evaporated under reduced pressure. The crude product was purified by preparative HPLC to give 26 as an oil (0.62 g, 78%).

Phenylsulfonyl 3CPr Carbamate (27)

A suspension of compound 26 (0.61 g, 1.61 mmol), Pd/C (0.31 g, 10% Pd) in EtOH (15 mL) was stirred under H₂ (balloon) at room temperature for 1.5 hours. The reaction mixture was filtered through Celite®. The filtercake was washed with EtOH (2×8 mL) and the combined filtrates were evaporated under reduced pressure to give 27 (0.41 g, 89%) as solid.

Synthesis of Phosphoryl 3CPr Carbamates (29a-c)

Scheme 10. (a) Dichlorophosphoryl isocyanate, DCM; (b) NaOEt, EtOH; (c) Gly-OEt•HCl, TEA, DCM; (d) 2, pyridine, DCM; (e) Pd/C, H₂, EtOH

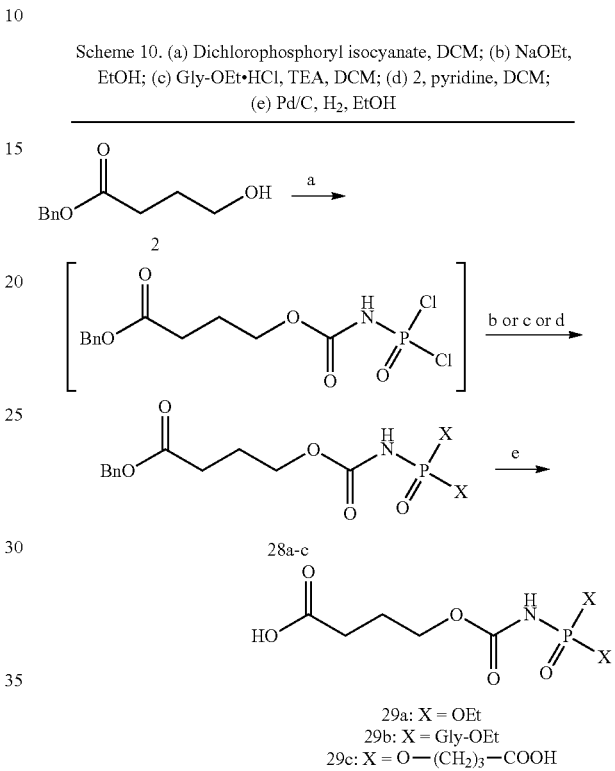

29a: X = OEt
29b: X = Gly-OEt
29c: X = O—(CH₂)₃—COOH

Diethoxyphosphoryl O-benzyl-3CPr carbamate (28a)

Dichlorophosphoryl isocyanate (0.142 mL, 1.44 mmol) was added to a solution of benzyl-4-hydroxy butanoate (0.28 g, 1.44 mmol) in DCM (10 mL) at 0-5° C. The reaction mixture was stirred at 0-5° C. for 1 hour. A solution of NaOEt in EtOH (1.5 mL, 21 wt %) was added dropwise at 0-5° C. The mixture was stirred at 0-5° C. for 3 h and then quenched with 10% aqueous $NH_4Cl$ (10 mL). DCM was removed under reduced pressure. The residue was partitioned between EtOAc (80 mL) and 10% aq. $NH_4Cl$ (50 mL). The EtOAc part was washed with brine, dried over anhydrous $Na_2SO_4$ and evaporated to dryness. The crude product was purified by preparative HPLC to give 28a (0.36 g, 67%) as an oil.

Diethoxyphosphoryl 3CPr Carbamate (29a)

A suspension of 28a (0.36 g, 0.96 mmol), Pd/C (10% Pd, 0.16 g) in EtOH (12 mL) was stirred under H₂ (balloon) for 1.5 hours. The reaction mixture was filtered through Celite®, washed with EtOH (2×4 mL) and the combined filtrates were evaporated under reduced pressure to give compound 29a as oil in quantitative yield.

Bis(O-Ethylglycine)-Phosphoryl O-Benzyl-3CPr Carbamate (28b)

To a solution of benzyl-4-hydroxy butanoate 2 (0.27 g, 1.39 mmol) in DCM (10 mL) was added dichlorophosphoryl isocyanate (0.137 mL, 1.39 mmol) at 0-5° C. The mixture was at 0-5° C. for 1.5 hours. Gly-OEt-HCl (0.43 g, 3.05 mmol) and TEA (0.55 mL, 4 mmol) were added, and the reaction mixture was stirred for 2 hours at 0-5° C. and then at room temperature for 1 hour. The reaction was quenched with water and solvents were evaporated under reduced pressure. The residue was taken in EtOAc (100 mL), washed with 10% aq NH$_4$Cl and brine, dried over anhydrous Na$_2$SO$_4$ and evaporated to dryness. The product was purified by preparative HPLC to give 28b as oil (0.44 g, 65%).

Bis(O-Ethylglycine)-Phosphoryl 3CPr Carbamate (29b)

Compound 28b was deprotected following the same procedure as described for 27a to give compound 29b in 81% yield.

Bis(3CPr)-Phosphoryl O-Benzyl-3CPr Carbamate (28c)

To a solution of benzyl-4-hydroxy butanoate 2 (0.74 g, 3.78 mmol) in DCM (12 mL) were added dichlorophosphoryl isocyanate (0.125 mL, 1.26 mmol) and pyridine (0.32 mL, 4 mmol) at 0-5° C. The reaction mixture was stirred for 5 hours at 0-5° C. and then at room temperature for 2 hours. The reaction was quenched with water and solvents were evaporated under reduced pressure. The residue was taken in EtOAc (100 mL), washed with 10% aq NH$_4$Cl (40 mL) and brine (40 mL), dried over anhydrous Na$_2$SO$_4$, and evaporated to dryness. The product was purified by preparative HPLC to give 28c as oil (0.43 g, 51%).

Bis(3CPr)-Phosphoryl 3CPr Carbamate (29c)

Compound 28c was deprotected following the same procedure as described for 27a, to give compound 29c in quantitative yield.

Synthesis of Diethyl 3CPr Phosphate (31)

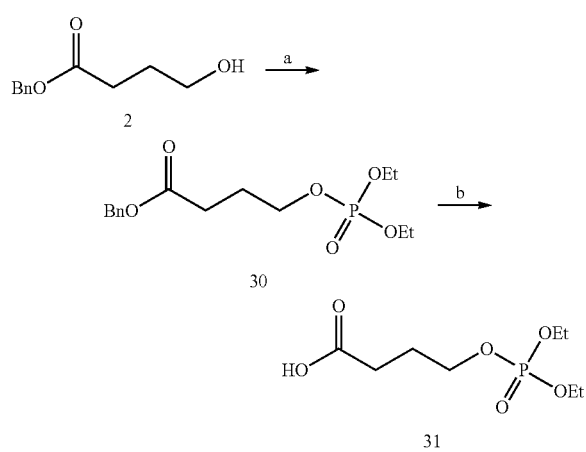

Scheme 11. (a) Diethyl chlorophosphate, pyridine, DCM; (b) Pd/C, H$_2$, EtOH

Diethyl O-Benzyl-3CPr Phosphate (30)

A solution of diethyl chlorophosphate (0.58 mL, 4 mmol) in DCM (3 mL) was added to a solution of benzyl-4-hydroxy butanoate 2 (0.625 g, 3.2 mmol) and pyridine (0.77 mL, 9.5 mmol) in DCM (10 mL) at 0-5° C. The reaction mixture was stirred at 0-5° C. for 3 h, quenched with water and solvent was evaporated under reduced pressure. The residue was taken in EtOAc (100 mL), washed with 10% aqueous NH$_4$Cl (50 mL), 5% aqueous NaHCO$_3$ (50 mL) and brine, dried over anhydrous Na$_2$SO$_4$ and evaporated to dryness. The phosphate derivative was purified by preparative HPLC to give diethyl O-benzyl-3CPr phosphate 30 as an oil (0.9 g, 85%).

Diethyl 3CPr Phosphate (31)

Deprotection of 30 under catalytic hydrogenation as described before afforded compound 31 as an oil in 96% yield.

Synthesis of 3CPr Sulfamate

Scheme 12. (a) sulfamoyl chloride, dimethyl acetamide, 0-5° C.; (b) Pd/C, H$_2$, EtOH

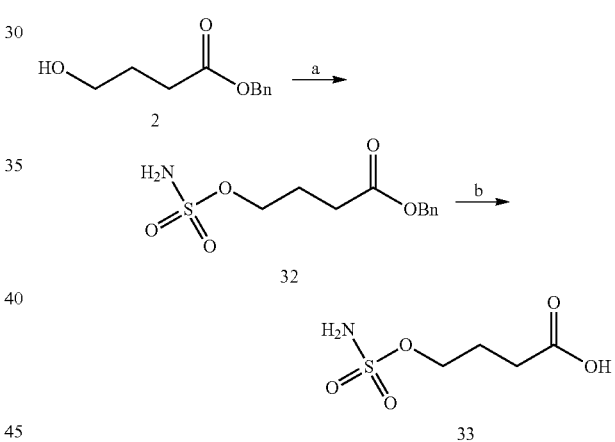

O-Benzyl-3CPr Sulfamate (32)

To a solution benzyl-4-hydroxybutanoate 2 (1.1 g, 5.66 mmol) in dimethylacetamide (5 mL) was added sulfamoyl chloride (1.31 g, 11.34 mmol) at 0-5° C. The reaction mixture was stirred for 1 hour at 0-5° C. and then poured into 10% aqueous NaCl solution (975 mL). The aqueous solution was extracted with EtOAc (100 mL), and the extract was washed with 10% aqueous NaCl solution, dried over anhydrous Na$_2$SO$_4$ and evaporated to dryness. The crude product was purified over silica gel (EtOAc:hexane, 1:1) to give 32 as an oil (1.41 g, 91%).

3CPr Sulfamate (33)

A suspension of 32 (0.93 g) and Pd/C (0.4 g) in EtOH (25 mL) was stirred for 1 h at room temperature. The reaction mixture was filtered through Celite® and the filtercake was washed with EtOH (2×10 mL). The combined filtrates were evaporated under reduced pressure to give 33 as white solid in quantitative yield.

Synthesis of (2-THF) Esters (34a-b and 35)

Scheme 13. (a) PPTS, DCM; (b) Pd/C, H₂, EtOH

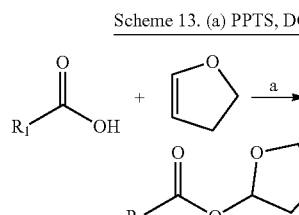

34a: R₁ = phenyl
34b: R₁ = 2-hydroxyphenyl
34c: R₁ = —(CH₂)₃—CO₂Bn

35
R₁ = —(CH₂)₃—CO₂H (2-THF) Benzoate (34a)

A solution of benzoic acid (1 g, 8.2 mmol) and pyridinium p-toluene sulfonate (PPTS) (0.021 g, 0.08 mmol) in anhydrous DCM was cooled while stirring over an ice-water bath (0-5° C.). To this mixture was dropwise added 2,3-dihydrofuran (0.743 g, 10.6 mmol) under inert atmosphere. Once the addition was complete, the ice-water bath was removed. The reaction was monitored by TLC and stopped upon completion. The reaction mixture was transferred into a separatory funnel, diluted with DCM, and the organic layer was washed with 5% aqueous NaHCO₃ and brine solution. The organic layer was dried over anhydrous Na₂SO₄ and filtered. The filtrate was evaporated under vacuum and the residue was purified over silica gel (hexane:EtOAc, 9:1) to give 34a (1.1 g, 72%) as colorless liquid.

(2-THF) Salicylate (34b)

(2-THF) salicylate (34b) was synthesized following the procedure described above in 67% yield as colorless liquid.

Benzyl (2-THF) Glutarate (34c)

To a stirred solution of mono-benzyl glutarate (0.5 g, 2.25 mmol) and 5 mg of pyridinium p-toluene sulfonate (PPTS) (0.02 mmol) in anhydrous dichloromethane was dropwise added 2,3-dihydrofuran (0.205 g, 2.93 mmol) under inert atmosphere at 0° C. The reaction mixture was slowly warmed up to room temperature. The reaction was monitored by TLC and stopped upon completion. The reaction mixture was transferred into a separatory funnel, diluted with DCM, and the organic layer was washed with 5% aqueous NaHCO₃ and brine solution. The organic layer was dried over anhydrous Na₂SO₄ and filtered. The filtrate was evaporated under vacuum. The residue was passed through a short silica gel column (hexane:EtOAc, 9:1) to obtain desired product 34c as colorless liquid (0.570 g, 87%).

O-(2-THF)-Glutaric Acid (35)

Benzyl (2-THF) glutarate 34c (0.57 g, 1.95 mmol) was dissolved in anhydrous tetrahydrofuran and stirred under H₂ in presence of 10% Pd/C (0.6 g) at room temperature. After 3 h, the suspension was passed through a pad of Celite®. The filtrate was removed under vacuum to obtain the desired product 35 (0.337 g, 86%) as viscous liquid.

Synthesis of O-(2-THF) O-(Ethoxycarbonyl)-GHB (38)

Scheme 14. (a) Ethyl chloroformate, pyridine; (b) Pd/C, H₂, THF; (c) PPTS, DCM

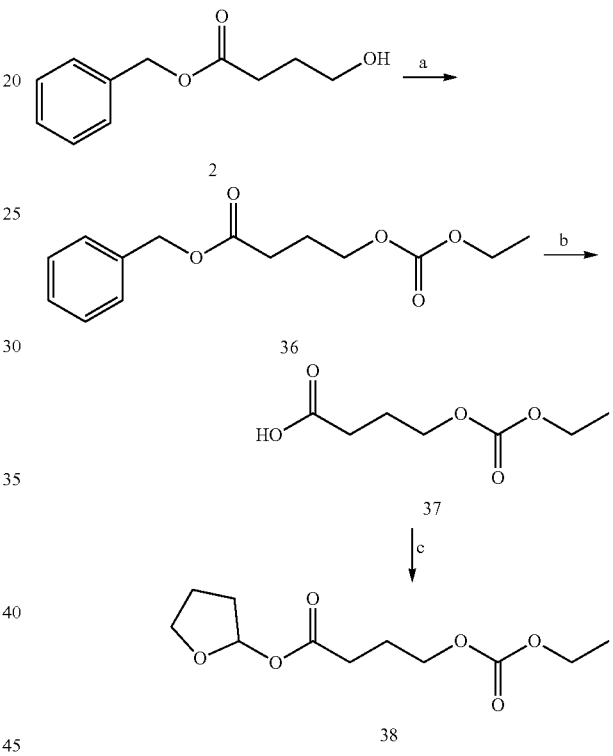

Benzyl O-(Ethoxycarbonyl)-4-Hydroxybutyrate (36)

While stirring, ethyl chloroformate (0.805 g, 7.42 mmol) was added dropwise to a solution benzyl 4-hydroxybutanoate 2 (1.2 g, 6.18 mmol) in anhydrous pyridine (15 mL) under inert atmosphere at 0-5° C. The reaction was slowly warmed up to room temperature and stirred. After 2 h, the reaction was stopped, and the volume was reduced under vacuum. The residue was taken up in EtOAc and the organic layer was washed with saturated aqueous NH₄Cl, water, and brine solution. The organic layer was dried over anhydrous Na₂SO₄, filtered, and the filtrate was evaporated under vacuum. The residue was purified over silica gel (hexane: EtOAc, 9:1) to obtain the carbonate derivative 36 as viscous liquid.

O-(Ethoxycarbonyl)-GHB (37)

A solution of compound 36 (0.68 g, 3.9 mmol) in anhydrous THF (25 mL) was stirred under H₂ atmosphere in presence of 10% Pd/C (0.2 g) at room temperature. After 3 h, the reaction was stopped and passed through a pad of Celite®. The filtrate was evaporated under vacuum to obtain O-(ethoxycarbonyl)-GHB 37 as viscous liquid. Yield: 0.45 g (65%).

O-(2-THF) O-(Ethoxycarbonyl)-GHB (38)

To a stirred solution of compound 37 (0.45 g, 2.55 mmol) and 8 mg of p-toluene pyridinium sulfonate (0.03 mmol) in anhydrous dichloromethane was dropwise added 2,3-dihydrofuran (0.233 g, 3.32 mmol) under inert atmosphere at 0° C. The reaction mixture was slowly warmed up to room temperature. The reaction was monitored by TLC and stopped upon completion. The reaction mixture was transferred into a separatory funnel, diluted with DCM, and the organic layer was washed with 5% aqueous NaHCO$_3$ and brine solution. The organic layer was dried over anhydrous Na$_2$SO$_4$ and filtered. The filtrate was evaporated under vacuum. The residue was passed through a short silica gel column (hexane:EtOAc, 9:1) to obtain the desired product 38 as viscous liquid (0.385 g, 61%).

Synthesis of Bis(2-THF) Carboxylates (39, 40, 41a-d)

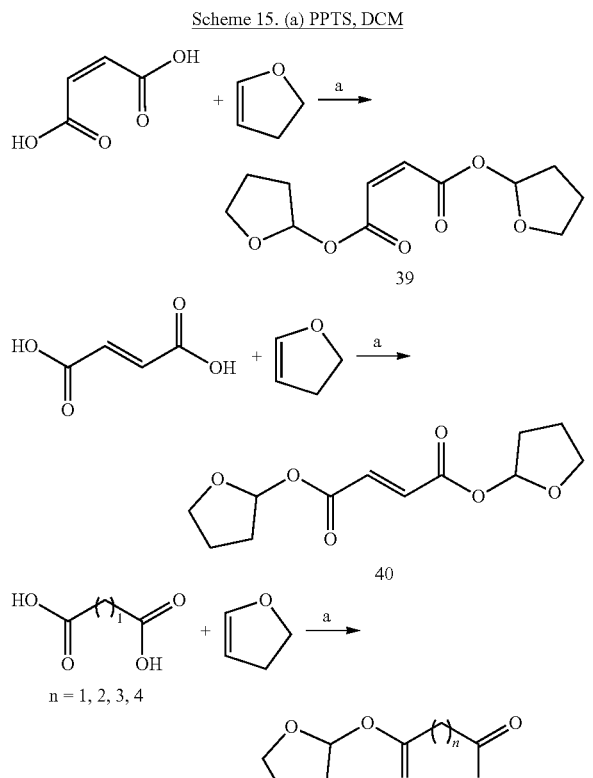

Bis(2-THF) Maleate (39)

While stirring, 2,3-dihydrofuran (1.2 g, 16.8 mmol) was added dropwise to a solution of maleic acid (0.75 g, 6.5 mmol) and pyridinium p-toluene sulfonate (PPTS) (0.033 g, 0.13 mmol) in anhydrous DCM under inert atmosphere over an ice-water bath (0-5° C.). Once the addition was complete, the ice-water bath was removed. The reaction was monitored by TLC and stopped upon completion. The reaction mixture was transferred into a separatory funnel, diluted with DCM, and the organic layer was washed with 5% aqueous NaHCO$_3$ and brine solution. The organic layer was dried over anhydrous Na$_2$SO$_4$ and filtered. The filtrate was evaporated under vacuum. The residue was passed through a short silica gel column (hexane:EtOAc, 9:1) to give 39 (1.39 g, 85%) as waxy solid.

Bis(2-THF) Fumarate (40)

Bis(2-THF) fumarate (40) was synthesized following the procedure described above (for 39) in 75% yield as viscous liquid.

Bis(2-THF) Dicarboxylates (41a-d)

Similarly, compounds bis(2-THF) glutarate (41a), bis(2-THF) succinate (41b), bis(2-THF) malonate (41c), and bis (2-THF) adipate (41d) were obtained as colorless viscous liquid with a yield of 61%, 67%, 53%, and 73%, respectively.

Synthesis of Bis-O-(2-THF) Ethers (42 and 43)

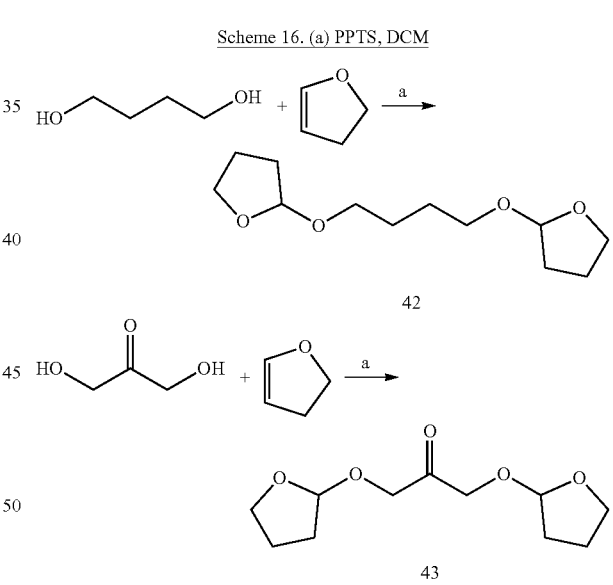

Bis-O-(2-THF) BD (42)

While stirring, 2,3-dihydrofuran (0.778 g, 11.1 mmol) was added dropwise to a solution of 1,4-butanediol (0.5 g, 5.5 mmol) and pyridinium p-toluene sulfonate (PPTS) (0.028 g, 0.11 mmol) in anhydrous DCM under inert atmosphere over an ice-water bath (0-5° C.). Once the addition was complete, the ice-water bath was removed. The reaction was monitored by TLC and stopped upon completion. The reaction mixture was transferred into a separatory funnel, diluted with DCM, and the organic layer was washed with 5% aqueous NaHCO$_3$ and brine solution. The organic layer was dried over anhydrous Na$_2$SO$_4$ and filtered. The filtrate was evaporated under vacuum. The residue was passed through a short silica gel column (hexane:EtOAc, 9:1) to afford compound 42 (1.06 g, 84%) as colorless oil.

Bis-O-(2-THF) 1,3-Dihydroxypropanone (43)

Bis-O-(2-THF) 1,3-dihydroxypropanone (43) was synthesized following the same procedure as described above in 66% yield as a colorless oil.

Synthesis of Coumaric Acid Conjugates of (2-THF) (44)

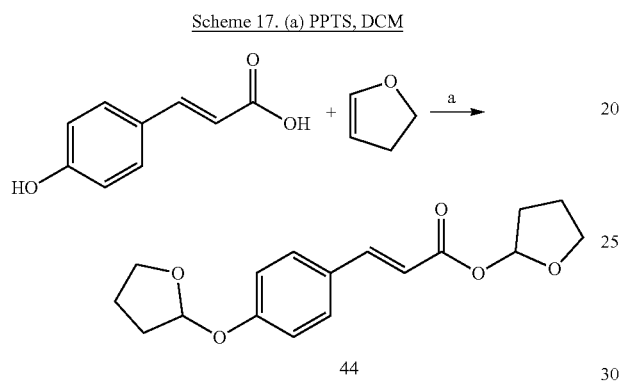

Scheme 17. (a) PPTS, DCM (2-THF) O-(2-THF) p-Coumarate (44)

While stirring, 2,3-dihydrofuran (0.194 g, 2.77 mmol) was added dropwise to a mixture of p-coumaric acid (0.35 g, 2.13 mmol) and p-toluene pyridinium sulfonate (0.005 g, 0.02 mmol) in anhydrous dichloromethane under inert atmosphere at 0° C. The mixture was slowly warmed up to room temperature. The reaction was monitored by TLC and stopped upon completion. The reaction mixture was transferred into a separatory funnel, diluted with DCM, and the organic layer was washed with 5% aqueous NaHCO$_3$ and brine solution. The organic layer was dried over anhydrous Na$_2$SO$_4$ and filtered. The filtrate was evaporated under vacuum. The residue was passed through a short silica gel column (hexane:EtOAc, 9:1) to obtain desired product 44 (0.222 g, 34%) as viscous liquid.

Synthesis of O-Acetyl-4-Hydroxybutyl Salicylate (45)

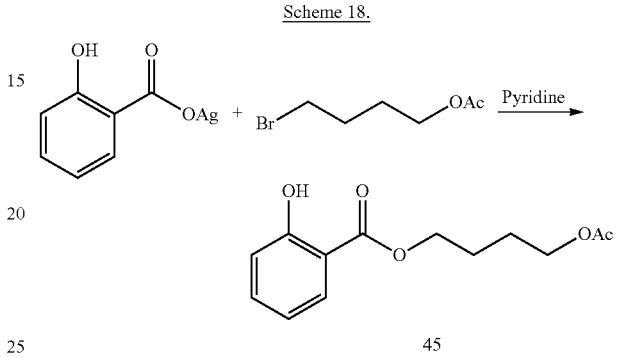

Scheme 18.

O-Acetyl-4-Hydroxybutyl Salicylate (45)

While stirring, 4-bromobutyl acetate (0.8 g, 4.1 mmol) was added dropwise to a solution of silver salicylate (1 g, 4.1 mmol) in anhydrous pyridine (10 mL) at room temperature. After overnight stirring, solvents were reduced under vacuum and the residue was taken up in EtOAc. The organic layer was washed with saturated NH$_4$Cl solution, water, and brine. The EtOAc layer was collected over anhydrous Na$_2$SO$_4$ and filtered. The filtrate was evaporated under vacuum, and the residue was purified over silica gel (hexane: EtOAc, 9:1) to obtain the desired product 45 (0.297 g, 37%) as viscous liquid.

Synthesis of GHB Amides (47a-i)

Scheme 19.
(a) HOBt, DCC, THF;
(b) HATU, DIPEA, DMF;
(c) HOSu, DCC, THF;
(d) amino acid/peptide benzyl ester, THF;
(e) Pd/C, H$_2$, EtOH or MeOH (for 47c)

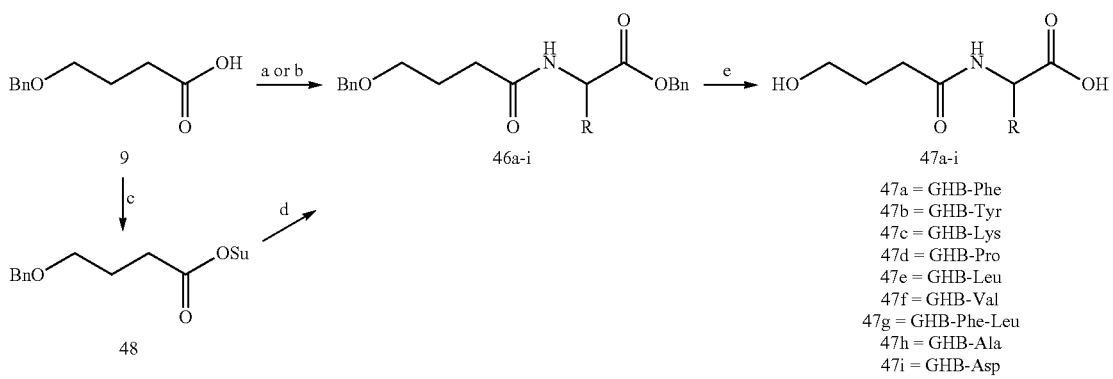

47a = GHB-Phe
47b = GHB-Tyr
47c = GHB-Lys
47d = GHB-Pro
47e = GHB-Leu
47f = GHB-Val
47g = GHB-Phe-Leu
47h = GHB-Ala
47i = GHB-Asp

O-Benzyl-GHB-Phe-O-Benzyl (46a)

To a solution of 4-benzyloxy butanoic acid (0.3 g, 1.5 mmol), HOBt (0.23 g, 1.6 mmol) in THF (10 mL) was added DCC (0.33 g, 1.6 mmol) in THF (3 mL) dropwise at room temperature. After stirring for 1 h, TEA (0.42 mL, 3 mmol) and Phe-OBn-HCl (0.46 g, 1.57 mmol) were added. The reaction mixture was stirred at room temperature for 4 h and then filtered. The filtrate was evaporated to dryness. The residue was dissolved in EtOAc (100 mL), and the resulting solution was washed with 10% aqueous $NH_4Cl$ (50 mL), 5% aqueous $NaHCO_3$ (50 mL) and brine (25 mL), dried over $Na_2SO_4$ and evaporated to dryness. The crude product was purified over silica gel to give O-benzyl-GHB-Phe 46a (0.61 g, 93%).

GHB-Phe (47a)

A suspension of 46a (0.61 g, 1.4 mmol), Pd/C (0.5 g, 10% Pd) in EtOH (15 mL) was stirred under $H_2$ (balloon) at room temperature for 5 hours the reaction mixture was filtered through Celite® and the filtercake washed with EtOH (2×8 mL). The combined filtrates were evaporated under reduced pressure to give 47a (0.33 g, 94%) as solid.

GHB-Tyr (47b), GHB-Lys (47c), and GHB-Pro (47d) were synthesized following the same procedure as described for 47a.

O-Benzyl-GHB-Leu-O-Benzyl (46e)

To a solution of 4-benzyloxy butanoic acid (0.305 g, 1.5 mmol), NHS (0.182 g, 1.57 mmol) in THF (9 mL) was added a solution of DCC (0.325 g, 1.57 mmol) in (3 mL) at 0-5° C. After stirring at room temperature for 6 h, the suspension was filtered and the filtrate was evaporated to dryness to afford hydroxysuccinimide ester 48. To a stirred solution of Leu-OBn-TsOH (0.61, 1.5 mmol) and TEA (0.55 mL, 4 mmol) in THF (6 mL) was added a solution of 48 in THF (4 mL). The reaction mixture was stirred overnight at room temperature. Solvents were evaporated under reduced pressure. The residue was dissolved in EtOAc (100 mL), and washed with 5% aqueous $NaHCO_3$ (50 mL) and brine (40 mL), dried over anhydrous $Na_2SO_4$ and evaporated to dryness. The crude product was purified over silica gel to give amide 46e as an oil (0.54 g, 90%).

GHB-Leu (47e)

A suspension of benzyl (4-(benzyloxybutanoyl))leucinate (0.54 g, 1.4 mmol), Pd/C (0.3 g, 10% Pd) in EtOH (12 mL) was stirred under $H_2$ (balloon) at room temperature for 5 hours the reaction mixture was filtered through Celite® and the filtercake was washed with EtOH (2×8 mL). The combined filtrates were evaporated under reduced pressure and dried to give 47e (0.29 g, 99%) as white solid.

GHB-Val (47f) and GHB-Phe-Leu (47g)

GHB-Val (47f) and GHB-Phe-Leu (47g) were synthesized following the procedure described above.

O-Benzyl-GHB-Ala-O-Benzyl (46h)

While stirring, DIPEA (2 g, 15.3 mmol) and Ala-OBn-TsOH (1.8 g, 5.1 mmol) were added to a mixture of 4-(benzyloxy)butanoic acid (1 g, 5.1 mmol) and HATU (1.9 g, 5.1 mmol) in anhydrous DMF (8 mL) at room temperature. After stirring for 12 h, the reaction was quenched by pouring over 5% aqueous bicarbonate solution. The aqueous layer was extracted with 3×50 mL of EtOAc. The organic layer was washed with water and brine, and dried over anhydrous $Na_2SO_4$. The organic layer was filtered and evaporated under vacuum. The residual amount was purified using silica gel (EtOAc:hexane, 1:4) to afford 46h (1.3 g, 72%)

GHB-Ala (47h)

Benzyl (4-(benzyloxy)butanoyl)alaninate 46h (1.3 g, 3.7 mmol) was dissolved in anhydrous EtOH (20 mL) and subjected to hydrogenation in the presence of Pd/C (0.5 g, 10% Pd). The reaction was stopped after 3 h of stirring, filtered through a pad of Celite®, and the filtrate was evaporated under vacuum to obtain the desired amide 47h (0.61 g, 95%). as waxy solid.

GHB-Asp (47i)

GHB-Asp (47i) was synthesized following the procedure described above.

Synthesis of GHB Amide Esters (52a-c)

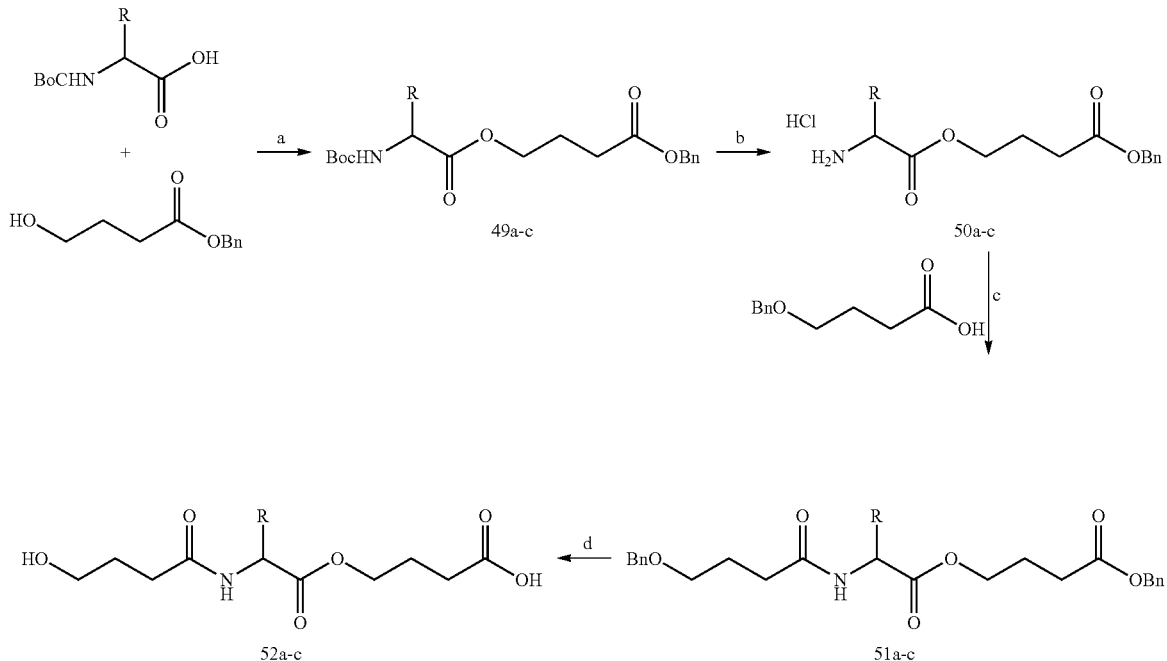

Scheme 20.
(a) BOP, HOBt, DIPEA, DMF;
(b) 4N HCl/dioxane;
(c) HATU, DIPEA, DMF;
(d) Pd/C, H$_2$, EtOH

Boc-Ser-GHB-O-Benzyl (49a)

While stirring, benzyl 4-hydroxybutanoate (0.35 g, 1.8 mmol) and DIPEA (0.650 g, 4.8 mmol) were added to a solution of Boc-Ser($^t$Bu)-OH (0.428 g, 1.6 mmol), BOP (0.796 g, 1.8 mmol), and HOBt (0.243 g, 1.8 mmol) in anhydrous DMF at room temperature under inert atmosphere. After stirring for 12 h, the reaction was quenched by pouring over 5% aqueous bicarbonate solution. The aqueous layer was extracted with 3×50 mL of EtOAc. The organic layer was washed with water and brine, and dried over anhydrous Na$_2$SO$_4$. The organic layer was filtered and evaporated under vacuum. The residue was purified over silica gel (EtOAc:hexane, 1:4) to give serine ester 49a (0.45 g, 64%).

Ser-GHB-O-Benzyl (50a)

Compound 49a (0.9 g, 2 mmol) was dissolved in 4(N) HCl/dioxane (12 mL) and stirred at room temperature for 30 mins. Solvents were evaporated under reduced pressure. The residue was co-evaporated with isopropyl acetate to obtain the deprotected compound 50a in quantitative yield.

O-Benzyl-GHB-Ser-GHB-O-Benzyl (51a)

While stirring, DIPEA was added dropwise to a mixture of compound 50a (0.653 g, 2.1 mmol), 4-(benzyloxy)butanoic acid (0.42 g, 2.2 mmol), and HATU (0.82 g, 2.2 mmol) in anhydrous DMF at room temperature. After stirring for 12 h, the reaction was quenched by pouring over 5% aqueous bicarbonate solution. The aqueous layer was extracted with 3×50 mL of EtOAc. The organic layer was washed with water and brine, and dried over anhydrous Na$_2$SO$_4$. The organic layer was filtered and evaporated under vacuum. The residue was purified using silica gel (EtOAc:hexane, 1:4) to give 51a (0.61 g, 63%).

GHB-Ser-GHB (52a)

Compound 51a (0.55 g, 1.2 mmol) was dissolved in anhydrous EtOH and stirred under H$_2$-atmosphere in the presence of 10% Pd/C (0.5 g). After overnight stirring, the reaction mixture was filtered through a pad of Celite® and the filtrate was removed under vacuum to obtain the desired product 52a (0.324 g, 97%) as gooey solid.

GHB-Asp(GHB)-GHB (52b)

GHB-Asp(GHB)-GHB (52b) was synthesized using a similar procedure.

GHB-Ala-GHB (52c)

GHB-Ala-GHB (52c) was synthesized using a similar procedure.

Synthesis of Di-O-(3CPr) Lactates

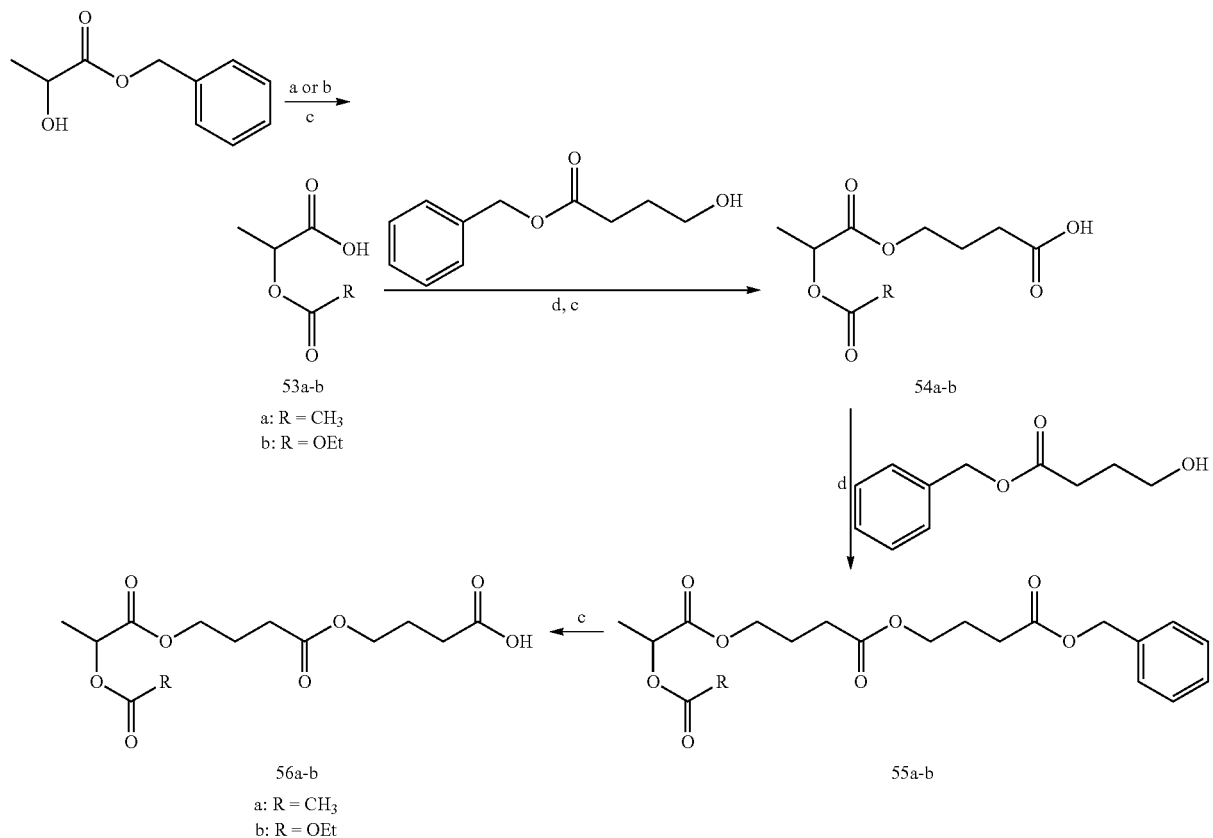

Scheme 21.
(a) Ac$_2$O, DMAP, DCM;
(b) Ethyl chloroformate, DMAP, DIPEA, DCM;
(c) Pd/C, H$_2$, EtOH,
(d) 2, DCC, DMAP, DCM

O-Acetolactic Acid (53a)

While stirring, acetic anhydride (0.85 g, 8.3 mmol) was added to a solution of benzyl lactate (1 g, 5.5 mmol) and DMAP (0.067 g, 0.55 mmol) in anhydrous DCM over an ice-bath (0-5° C.). The ice-bath was removed once the addition was completed, and the reaction was stirred for an additional 1.5 h at room temperature. The reaction was quenched by pouring over water and the mixture was extracted with 3×50 mL of DCM. The organic layer was dried over anhydrous Na$_2$SO$_4$ and filtered. The filtrate was evaporated under vacuum to obtain the acetate ester which was used without further purification in the next step.

The acetate ester was subjected to hydrogenation in presence of 10% Pd/C (0.2 g) in ethanol (25 mL) at room temperature. After 1 h of stirring, the reaction was filtered through a pad of Celite®. The filtrate was evaporated under vacuum to obtain compound 53a as pale-yellow viscous oil (0.38 g, 55%, in 2 steps).

3CPr O-Acetolactate (54a)

While stirring, benzyl 4-hydroxybutanoate 2 (0.56 g, 2.9 mmol) was added to a solution of O-acetolactic acid 53a (0.38 g, 2.09 mmol), DCC (0.595 g, 2.88 mmol), and DMAP (0.037 g, 0.3 mmol) in anhydrous DCM at 0-5° C. The reaction mixture was slowly warmed up to room temperature. After overnight stirring, the reaction mixture was filtered, and the filtrate was washed with water and brine. The organic layer was dried over anhydrous Na$_2$SO$_4$, filtered, and the filtrate was evaporated under vacuum to obtain a viscous oil. The crude product was purified using silica gel (hexane:EtOAc, 9:1) to obtain the intermediate benzyl ester as colorless oil which was subjected to hydrogenation as described above to obtain GHB O-acetolactate 54a as pale yellow oil (0.25 g, 40% in 2 steps).

Di-O-(3CPr) O-Acetolactate (56a)

Di-O-(3CPr) O-acetolactate (56a) was synthesized following the same synthetic procedure as described for 54a, in 48% yield (from 54a).

O-(Ethoxycarbonyl)Lactic Acid (53b)

While stirring, DIPEA (1.78 g, 13.7 mmol), ethyl chloroformate (0.746 g, 6.9 mmol), and a catalytic amount of DMAP were added to a solution of benzyl lactate (1 g, 5.5 mmol) in anhydrous DCM at 0-5° C. The reaction mixture was slowly warmed up to room temperature and stirred overnight. The reaction was quenched by pouring over water and extracted with 3×50 mL of DCM. The DCM layer was washed with water and brine. The solution was dried over anhydrous $Na_2SO_4$, filtered, and the filtrate was evaporated under vacuum to obtain an oily residue. The residue was purified over silica gel (hexane:EtOAc, 95:5) to obtain the ethyl carbonate intermediate as colorless oil.

The ethyl carbonate intermediate was subjected to hydrogenation in the presence of 10% Pd/C (0.25 g) in ethanol at room temperature. After 1 h of stirring, the reaction was filtered through a pad of Celite®. The filtrate was evaporated under vacuum to obtain 53b as pale-yellow oil (0.52 g, 62%, in 2 steps).

3CPr O-(Ethoxycarbonyl)Lactate (54b)

3CPr O-(ethoxycarbonyl)lactate (54b) was synthesized by adopting the procedure described above.

Di-O-(3CPr) O-(Ethoxycarbonyl)Lactate (56b)

Di-O-(3CPr) O-(ethoxycarbonyl)lactate (56b) was synthesized by adopting the same procedure as described for 54a.

Synthesis of O-(2-THF)-GHB (58)

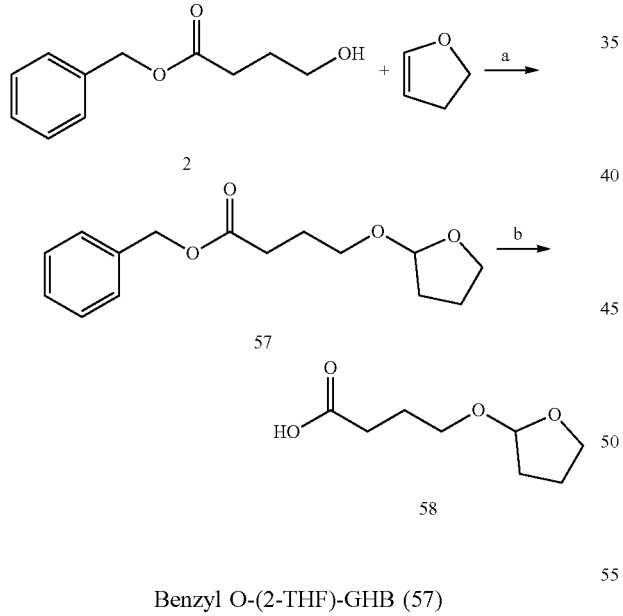

Benzyl O-(2-THF)-GHB (57)

A solution of 4-hydroxybutanoate 2 (1 g, 5.1 mmol) and pyridinium p-toluene sulfonate (0.026 g, 0.1 mmol) in anhydrous dichloromethane (15 mL) was stirred over an ice-bath. To this mixture was added dropwise 2,3-dihydrofuran (0.43 g, 6.2 mmol). The reaction mixture was slowly warmed up to room temperature. After 3 h of stirring, the reaction mixture was diluted by the addition of 50 mL of DCM. The organic layer was transferred into a separatory funnel and washed with 5% $NaHCO_3$ solution, water, and brine. The organic layer was dried over anhydrous $Na_2SO_4$, filtered, and solvents were evaporated under vacuum to obtain a pale-yellow color liquid. The crude product was purified over silica gel (hexane:EtOAc, 9:1) to obtain 57 as colorless oil (1.18 g, 86%).

O-(2-THF)-GHB (58)

A suspension of benzyl O-(2-THF)-GHB 57 (1.1 g, 4.2 mmol) and 10% Pd/C (0.44 g) in anhydrous methanol (30 mL) was stirred under $H_2$ at room temperature. The reaction was stopped after 1 h and the mixture was passed through Celite®. The filtrate was evaporated under vacuum to obtain the desired compound 58 as a colorless oil (0.69 g, 95%).

Synthesis of 4-Hydroxybutyl O-(2-THF)-GHB (62)

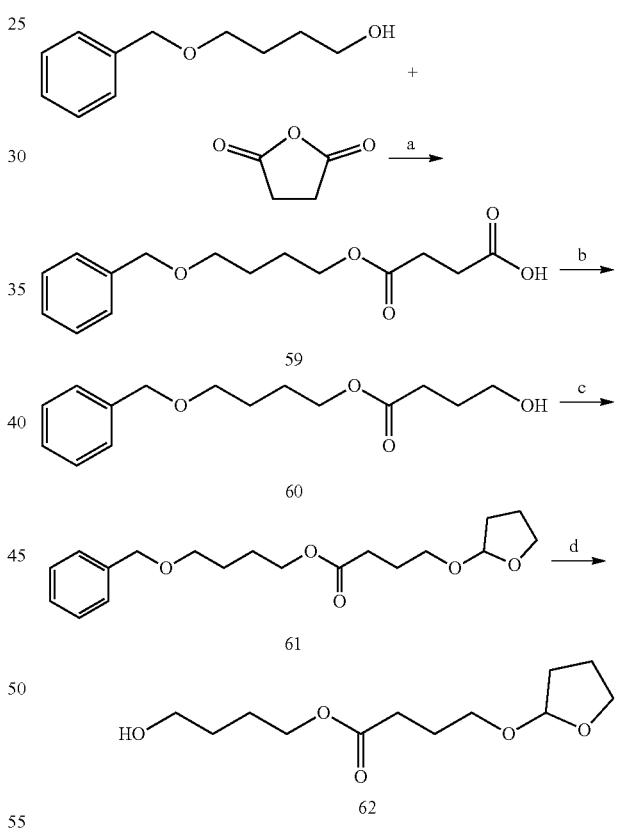

O-Benzyl-4-Hydroxybutyl Succinate (59)

To a solution of 4-(benzyloxy)butan-1-ol (2 g, 11.1 mmol) in anhydrous DCM (15 mL) was added triethylamine (1.23 g, 12.2 mmol), dimethyaminopyridine (0.014 g, 0.1 mmol), and succinic anhydride (1.2 g, 12.2 mmol). After stirring at room temperature overnight, the reaction was transferred into a separatory funnel, diluted with DCM (70 mL), and extracted with 5% sodium bicarbonate solution. The bicarbonate layer was adjusted to pH 2 by the addition of 0.5M HCl and extracted with EtOAc. The organic layer was dried over anhydrous Na$_2$SO$_4$, filtered, and solvents were evaporated under vacuum to obtain O-benzyl-4-hydroxybutyl succinate 59 as waxy solid (2.41 g, 77%).

O-Benzyl-4-Hydroxybutyl GHB (60)

A solution of compound 59 (1.58 g, 5.6 mmol) in anhydrous THF was cooled to −20° C. To this was dropwise added a solution of BH$_3$·Me$_2$S (3.7 mL, 7.3 mmol) in THF. The reaction mixture was slowly warmed up to room temperature and stirred for 4 hours. The reaction was quenched by the addition of 100 mL of diethyl ether and washed with 2% aqueous potassium carbonate solution. The organic layer was dried over anhydrous Na$_2$SO$_4$, filtered, and solvents were evaporated under vacuum to obtain a pale-yellow viscous liquid. The crude product was purified over silica gel to obtain compound O-benzyl-4-hydroxybutyl GHB 60 as a colorless oil (1.2 g, 80%).

O-Benzyl-4-Hydroxybutyl O-(2-THF)-GHB (61)

A solution of compound 60 (1.7 g, 6.4 mmol) and pyridinium p-toluene sulfonate (0.032 g, 0.13 mmol) in anhydrous dichloromethane (15 mL) was stirred over an ice bath. To this mixture was added dropwise 2,3-dihydrofuran (0.58 g, 8.3 mmol). The reaction mixture was slowly warmed up to room temperature. After stirring for 3 h, the reaction mixture was diluted by the addition of 50 mL of DCM. The organic layer was transferred to a separatory funnel and washed with 5% NaHCO$_3$ solution, water, and brine. The organic layer was dried over anhydrous Na$_2$SO$_4$, filtered, and solvents were evaporated under vacuum. The crude product was purified over silica gel (hexane:EtOAc, 9:1) to obtain compound 61 as colorless oil (1.03 g, 48%).

4-Hydroxybutyl O-(2-THF)-GHB (62)

A suspension of compound 61 (1.03 g, 3.0 mmol), 10% Pd/C (0.5 g) in anhydrous methanol (30 mL) was stirred under H$_2$ (balloon) at room temperature. After 1 h of stirring, the suspension was filtered through Celite®. The filtrate was evaporated under vacuum to obtain the compound 62 as a colorless oil (0.624 g, 84%).

Synthesis of 4-Hydroxybutyl GHB Esters (63a-b)

Scheme 24
(a) 4-Benzyloxy butanol, DCC, DMAP, DCM;
(b) Pd/C, H$_2$, EtOH

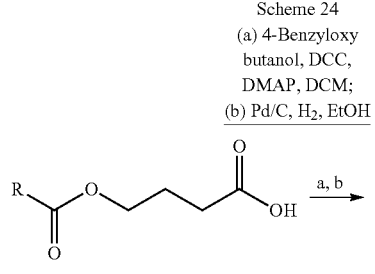

3a-b
3a: R = —OEt
3b: R = —CH$_3$

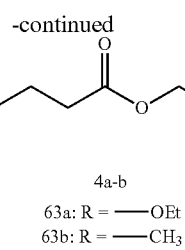

4a-b
63a: R = —OEt
63b: R = —CH$_3$

O-Benzyl-4-Hydroxybutyl O-(Ethoxycarbonyl)-GHB

A solution of DCC (0.43 g, 2.1 mmol) in CH$_2$Cl$_2$ (4 mL) was added dropwise to a solution of 3a (0.35 g, 2.0 mmol), 4-benzyloxybutanol (0.36 g, 2.0 mmol) and DMAP (0.03 g) in CH$_2$Cl$_2$ (8 mL) at 0-5° C. The reaction mixture was brought to room temperature and stirred for 4 h. The precipitate was filtered, washed with DCM and the combined filtrates were evaporated to dryness. The crude product was purified by preparative HPLC to give O-benzyl-4-hydroxybutyl O-(ethoxycarbonyl)-GHB as an oil (0.455 g, 67%).

4-Hydroxybutyl (O-Ethoxycarbonyl)-GHB (63a)

A suspension of O-benzyl-4-hydroxybutyl O-(ethoxycarbonyl)-GHB (0.45 g, 1.33 mmol) and Pd/C (10% Pd, 0.3 g) in EtOH (15 mL) was stirred under H$_2$ (balloon) at room temperature for 5 h. The reaction mixture was filtered through Celite® and washed with EtOH (2×5 mL). The combined filtrates were evaporated under reduced pressure and dried to give 63a as an oil (0.3 g, 91%).

4-Hydroxybutyl O-Acetyl-GHB (63b)

4-Hydroxybutyl O-acetyl-GHB 63b was synthesized following the same synthetic procedure as 63a.

Synthesis of Di-O-(3CPr) O-(Ethoxycarbonyl)-GHB (64)

Scheme 25
(a) 2, DCC, DMAP, DCM;
(b) Pd/C, H$_2$, EtOH

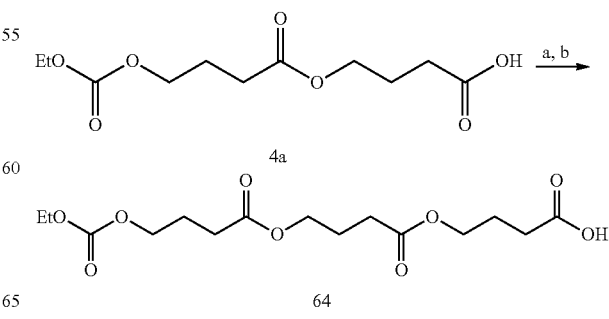

4a

64

Di-O-(3CPR) O-(Ethoxycarbonyl)-GHB (64)

Di-O-(3CPr) O-(ethoxycarbonyl)-GHB 64 was synthesized following the same synthetic procedure as described for 4a.

Synthesis of O-(2-THF) BD (66)

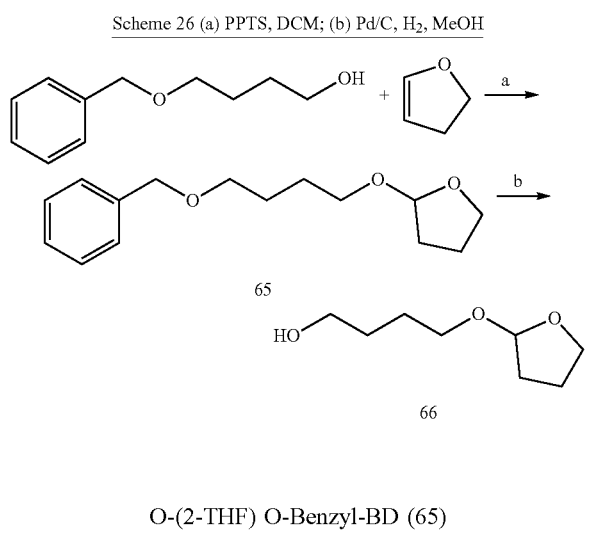

O-(2-THF) O-Benzyl-BD (65)

While stirring, 2,3-dihydrofuran (0.34 g, 4.8 mmol) was added dropwise to a solution of 4-benzyloxybutanol (0.72 g, 4 mmol) and pyridinium p-toluenesulfonate (0.01 g, 0.04 mmol) in anhydrous DCM (8 mL) at 0-5° C. After the addition, the reaction mixture was slowly warmed up to room temperature. After 2 h of stirring, the mixture was diluted by the addition of 50 mL DCM. The organic layer was washed with 5% NaHCO$_3$ solution, water, and brine. The organic layer was dried over anhydrous Na$_2$SO$_4$ and evaporated under vacuum to obtain a pale-yellow color liquid. The crude product was purified over silica gel (hexane:EtOAc, 9:1) to obtain O-(2-THF) O-benzyl-BD 65 as colorless oil (0.82 g, 83%).

O-(2-THF) BD (66)

A suspension of O-(2-THF) O-benzyl-BD 65 (0.82 g, 3.3 mmol), Pd/C (10% Pd, 0.25 g) in anhydrous EtOH (30 mL) was stirred under H$_2$ for 2 h. The reaction mixture was filtered through Celite®, and the filtrate was removed under vacuum and dried to give 66 as pale-yellow oil (0.31 g, 58%).

Synthesis of Bis(3CPr) Sulfite 68

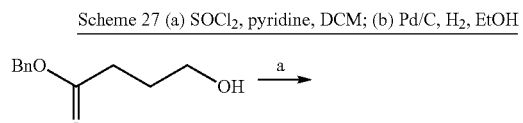

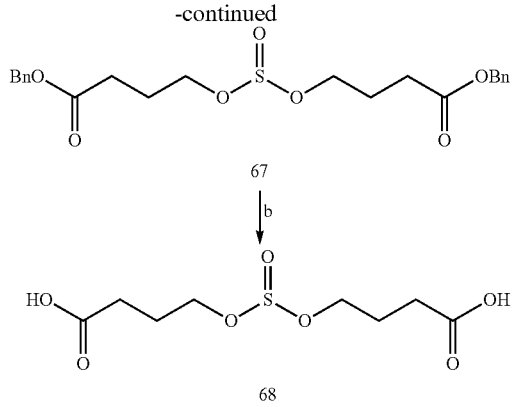

Bis(O-Benzyl-3CPr) Sulfite (67)

To a solution of 2 (0.52 g, 2.68 mmol) and pyridine (0.22 mL, 2.75 mmol) in DCM (10 mL) was added dropwise a solution of SOCl$_2$ in DCM at 0-5° C. The reaction mixture was stirred at 0-5° C. for 1 h, then at room temperature for 2 h. The reaction was quenched with water (a few drops) and the solvent was evaporated under reduced pressure. The residue was taken in EtOAc (80 mL), washed with 10% aqueous NH$_4$Cl (60 mL) and brine (50 mL). The organic phase was dried over anhydrous Na$_2$SO$_4$ and evaporated to dryness. The crude product was purified by preparative HPLC to give bis(O-benzyl-3CPr) sulfite 67 as colorless oil (0.43 g, 37%).

Bis(3CPr) Sulfite (68)

A suspension of 67 (0.43 g, 1 mmol) and Pd/C (10% Pd, 0.3 g) in anhydrous ethanol (20 mL) was stirred under H$_2$ for 2 h. The reaction mixture was filtered through Celite® and the filtrate evaporated to dryness. The residue was redissolved in EtOH and a second hydrogenation was performed under the same conditions for 1 h to give 68 as viscous oil (0.21 g, 82%).

Synthesis of Sugar Alcohol O-(2-THF) Ethers 69a-d

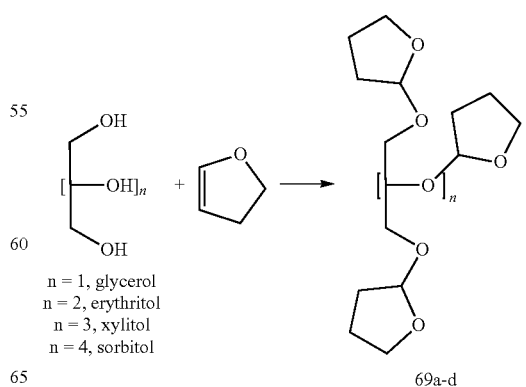

General Synthetic Procedure

To a solution of sugar alcohol (1 eq.) and 2,3-dihydrofuran (1.5 eq. per sugar alcohol hydroxy group) was added PPTS (0.01 eq. per hydroxy group). The reaction mixture was stirred at room temperature for 2-4 days. The reaction was quenched with 5% aqueous NaHCO$_3$ (1-2 mL) and most of the dioxane was evaporated under reduced pressure. The residue was taken in EtOAc and washed with 5% aqueous NaHCO$_3$ and brine. The organic layer was dried over anhydrous Na$_2$SO$_4$ and evaporated to dryness to give 69a-d as a viscous oil. The crude product was purified over silica gel (EtOAc/Hexane) to produce 69a-d in 85-90% yield.

Synthesis of Ascorbate Tetrakis-O-(Tetrahydrofuran-2-yl) Ether (70)

Ascorbate tetrakis-O-(tetrahydrofuran-2-yl) ether 70 was synthesized following the same general procedure described above for sugar alcohol O-(2-THF) ethers and was obtained in 33% yield as pale yellow, viscous oil.

TABLE 1

| Compound | Structure |
|---|---|
| 4a | 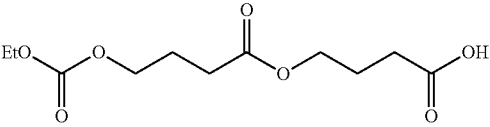 3CPr O-(ethoxycarbonyl)-GHB |
| 4b | 3CPr O-acetyl-GHB |
| 10 | GHB-Gly-GHB-GHB |
| 13a | bis(3CPr) carbonate |
| 13b | 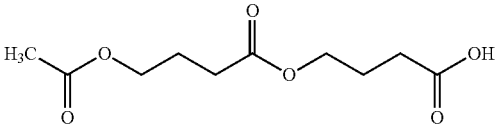 bis(3CPr) carbonate, disodium |

TABLE 1-continued

| Compound List | |
|---|---|
| Compound | Structure |
| 15 | glycerol tris(3CPr carbonate) |
| 17 | 4-hydroxybutyl 3CPr carbonate |
| 19a | (Val)-N-yl-sulfonyl 3CPr carbamate |
| 19b | (Ala)-N-yl-sulfonyl 3CPr carbamate |
| 19c | (β-Ala)-N-yl-sulfonyl 3CPr carbamate |
| 19d | (Phe)-N-yl-sulfonyl 3CPr carbamate |

TABLE 1-continued
Compound List
| Compound | Structure |
|---|---|
| 19e | 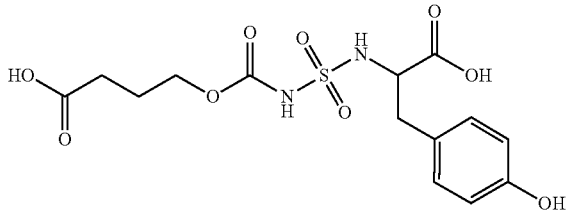<br>(Tyr)-N-yl-sulfonyl 3CPr carbamate |
| 19f | 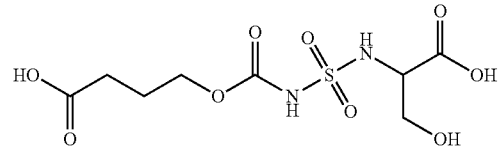<br>(Ser)-N-yl-sulfonyl 3CPr carbamate |
| 19g | 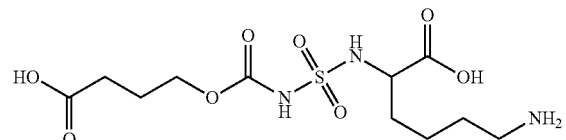<br>(Lys)-N-yl-sulfonyl 3CPr carbamate |
| 19h | 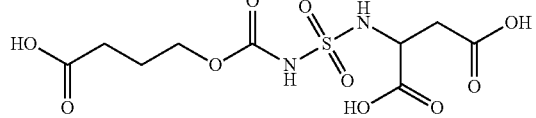<br>(Asp)-N-yl-sulfonyl 3CPr carbamate |
| 19i | 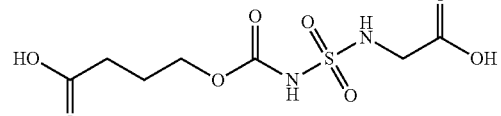<br>(Gly)-N-yl-sulfonyl 3CPr carbamate |
| 19j | 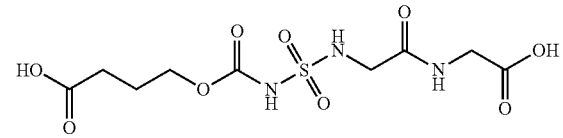<br>(Gly-Gly)-N-yl-sulfonyl 3CPr carbamate |
| 21 | 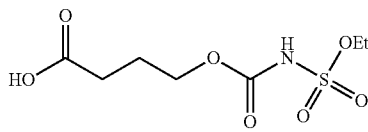<br>ethoxysulfonyl 3CPr carbamate |

TABLE 1-continued

Compound List

| Compound | Structure |
|---|---|
| 23a | benzoyl 3CPr carbamate |
| 23b | N-(ethoxycarbonyl) 3CPr carbamate |
| 25 | N-(ethoxycarbonyl) 3CPr thiocarbamate |
| 27 | phenylsulfonyl 3CPr carbamate |
| 29a | diethoxyphosphoryl 3CPr carbamate |
| 29b | bis(O-ethylglycine)-phosphoryl 3CPr carbamate |
| 29c | bis(3CPr)-phosphoryl 3CPr carbamate |
| 31 | diethyl 3CPr phosphate |

TABLE 1-continued

Compound List

| Compound | Structure |
|---|---|
| 33 | 3CPr sulfamate |
| 34a | (2-THF) benzoate |
| 34b | (2-THF) salicylate |
| 35 | O-(2-THF) glutaric acid |
| 38 | O-(2-THF) O-(ethoxycarbonyl)-GHB |
| 39 | bis(2-THF) maleate |
| 40 | bis(2-THF) fumarate |
| 41a | bis(2-THF) glutarate |

TABLE 1-continued
Compound List
| Compound | Structure |
|---|---|
| 41b | 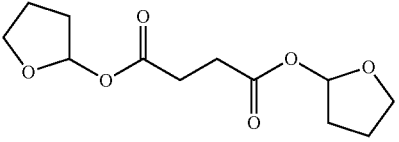 bis(2-THF) succinate |
| 41c | 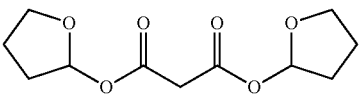 bis(2-THF) malonate |
| 41d | 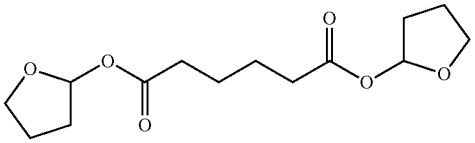 bis(2-THF) adipate |
| 42 | 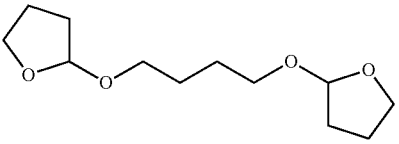 bis-O-(2-THF) BD |
| 43 | 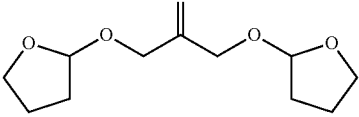 bis-O-(2-THF) 1,3-dihydroxypropanone |
| 44 | 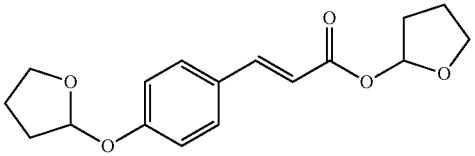 (2-THF) O-(2-THF) p-coumarate |
| 45 | 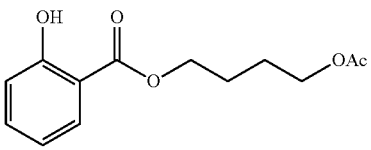 O-acetyl-4-hydroxybutyl salicylate |

TABLE 1-continued
| Compound | Structure |
|---|---|
| 47a | 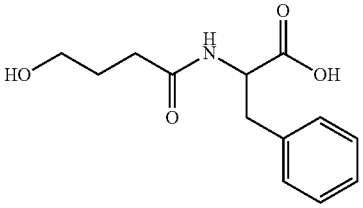<br>GHB-Phe |
| 47b | 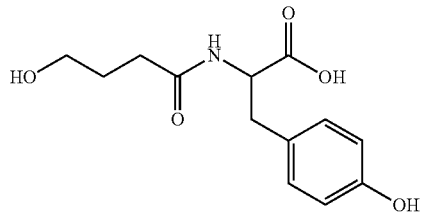<br>GHB-Tyr |
| 47c | 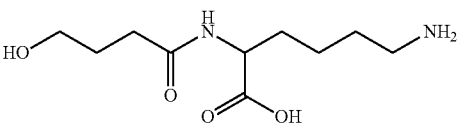<br>GHB-Lys |
| 47d | 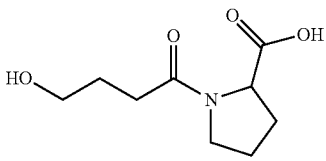<br>GHB-Pro |
| 47e | 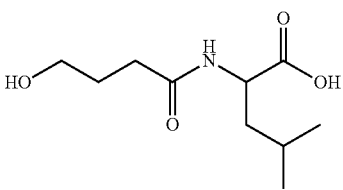<br>GHB-Leu |
| 47f | 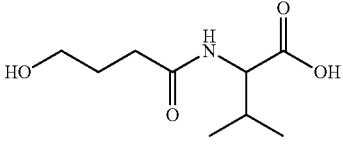<br>GHB-Val |

TABLE 1-continued

| Compound List | |
|---|---|
| Compound | Structure |
| 47g | GHB-Phe-Leu |
| 47h | GHB-Ala |
| 47i | GHB-Asp |
| 52a | GHB-Ser-GHB |
| 52b | GHB-Asp(GHB)-GHB |
| 52c | GHB-Ala-GHB |

TABLE 1-continued

Compound List

| Compound | Structure |
|---|---|
| 54a | 3CPr O-acetolactate |
| 54b | 3CPr O-(ethoxycarbonyl)lactate |
| 56a | di-O-(3CPr) O-acetolactate |
| 56b | di-O-(3CPr) O-(ethoxycarbonyl)lactate |
| 58 | O-(2-THF)-GHB |
| 62 | 4-hydroxybutyl O-(2-THF)-GHB |
| 63a | 4-hydroxybutyl (O-ethoxycarbonyl)-GHB |

TABLE 1-continued

Compound List

| Compound | Structure |
|---|---|
| 63b | 4-hydroxybutyl O-acetyl-GHB |
| 64 | di-O-(3CPr) O-(ethoxycarbonyl)-GHB |
| 66 | O-(2-THF) BD |
| 68 | bis(3CPr) sulfite |
| 69a | glycerol tris-O-(2-THF) ether |
| 69b | erythritol tetrakis-O-(2-THF) ether |

TABLE 1-continued
Compound List
| Compound | Structure |
|---|---|
| 69c | 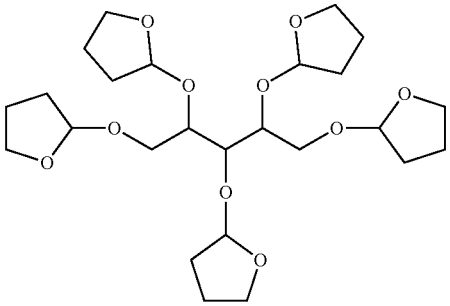<br>xylitol pentakis-O-(2-THF) ether |
| 69d | 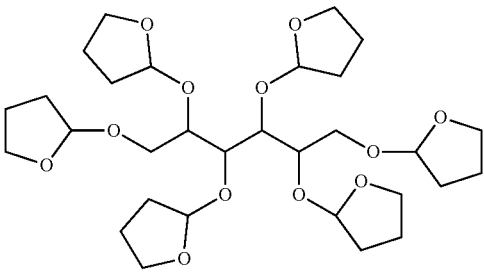<br>sorbitol hexakis-O-(2-THF) ether |
| 70 | 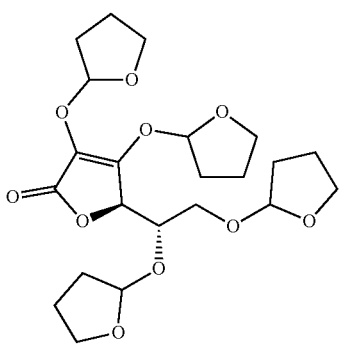<br>ascorbate tetrakis-O-(2-THF) ether<br><br>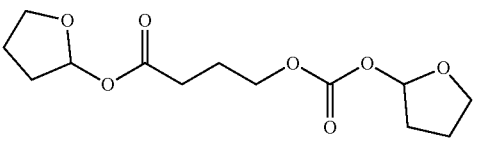<br>O-(2-THF)-3CPr O-(2-THF) carbonate |

EXAMPLES

Pharmacokinetic Profiles of GHB Delivering Compounds

Studies were conducted in rats to assess the pharmacokinetics of various conjugated GHB delivering compounds. Table 2 shows the mean pharmacokinetic parameters of GHB in plasma after administration in Sprague-Dawley rats via oral gavage. The blood was sampled at 0.25 hours, 0.5 hours, 1 hours, 2 hours, 3 hours, and 4 hours post-dose of the GHB delivering compounds. The GHB delivering compounds were formulated into a composition containing water, PEG-400/water (1:1), or PEG-400/water (1:3). Each administered dose was the molar equivalent of 100 mg/kg sodium oxybate (NaGHB) unless stated otherwise.

TABLE 2

Mean Pharmacokinetic Parameters of GHB in Plasma after Administration in Sprague-Dawley Rats via Oral Gavage.

| Conjugate | $C_{max}$ (ng/mL) | $AUC_{0-4\ hr}$ (h*ng/ml) | $T_{max}$ (hours) |
|---|---|---|---|
| 3CPr O-(ethoxycarbonyl)-GHB (4a) [a, b] | 4.6 | 7.5 | 0.55 |
| 3CPr O-(ethoxycarbonyl)-GHB (4a) [b] | 12.4 | 12.2 | 0.25 |
| 3CPr sulfamate (33) [c] | 41.6 | 51.6 | 0.85 |
| (2-THF) salicylate (34b) [b] | 30.8 | 20.3 | 0.25 |
| O-(2-THF)-glutaric acid (35) [b] | 35.1 | 37.8 | 0.25 |
| O-(2-THF) O-(ethoxycarbonyl)-GHB (38) [b] | 27.3 | 36.4 | 0.25 |
| bis(2-THF) maleate (39) [b] | 43.1 | 50.6 | 0.45 |
| bis(2-THF) glutarate (41a) [b] | 24.6 | 33.5 | 0.40 |
| bis(2-THF) succinate (41b) [b] | 30.3 | 32.0 | 0.25 |
| bis(2-THF) malonate (41c) [b] | 26.3 | 21.9 | 0.25 |
| bis(2-THF) adipate (41d) [d] | 39.0 | 38.3 | 0.50 |
| O-(2-THF)-GHB (58) [b] | 27.8 | 46.4 | 0.69 |
| 4-hydroxybutyl (O-ethoxycarbonyl)-GHB (63a) [b] | 13.8 | 15.9 | 0.25 |
| 4-hydroxybutyl O-acetyl-GHB (63b) [b] | 24.6 | 32.3 | 0.50 |
| O-(2-THF) BD (66) [c, e] | 21.0 | 27.3 | 0.60 |
| O-(2-THF) BD (66) [b] | 27.8 | 31.5 | 0.55 |
| glycerol tris-O-(2-THF) ether (69a) [d] | 17.5 | 21.2 | 0.25 |
| erythritol tetrakis-O-(2-THF) ether (69b) [d] | 13.6 | 16.1 | 0.25 |
| xylitol pentakis-O-(2-THF) ether (69c) [d] | 6.27 | 7.30 | 0.25 |
| 2-OH-THE [c] | 86.9 | 87.3 | 0.40 |
| GBL [c] | 15.4 | 9.04 | 0.25 |
| BD [c] | 17.8 | 29.1 | 0.70 |
| O-(ethoxycarbonyl)-GHB [c, e] | 15.0 | 19.4 | 0.35 |

[a] Dose in this study was equivalent to 70 mg/kg NaGHB. Data shown extrapolated to 100 mg/kg (assuming dose proportionality) for easier comparison with other studies.
[b] Vehicle = PEG-400/water (1:1)
[c] Vehicle = water
[d] Vehicle = PEG-400/water (1:3)
[e] Dose in this study was equivalent to 80 mg/kg NaGHB. Data shown extrapolated to 100 mg/kg (based on dose proportionality) for easier comparison with other studies.

The pharmacokinetic data from these studies were used to also assess the relative oral bioavailability of GHB (Table 3) after administration of the GHB delivering compounds as compared to sodium oxybate in Sprague-Dawley rats. The calculated % parameter (i.e., % $C_{max}$ or % AUC) is equal to the mean conjugate PK parameter/mean comparator PK parameter.

TABLE 3

Relative Oral Bioavailability vs Study Comparator (Sodium Oxybate) in Sprague-Dawley Rat.

| Conjugate | % $C_{max}$ | % $AUC_{0-4\ hr}$ |
|---|---|---|
| 3CPr O-(ethoxycarbonyl)-GHB (4a) [a, b] | 112% | 91% |
| 3CPr O-(ethoxycarbonyl)-GHB (4a) [b] | 145% | 75% |
| 3CPr sulfamate (33) [c] | 102% | 109% |
| (2-THF) salicylate (34b) [b] | 339% | 116% |
| O-(2-THF)-glutaric acid (35) [b] | 261% | 174% |
| O-(2-THF) O-(ethoxycarbonyl)-GHB (38) [b] | 250% | 170% |
| bis(2-THF) maleate (39) [b] | 395% | 237% |
| bis(2-THF) glutarate (41a) [b] | 181% | 157% |
| bis(2-THF) succinate (41b) [b] | 223% | 150% |
| bis(2-THF) malonate (41c) [b] | 195% | 101% |
| bis(2-THF) adipate (41d) [d] | 248% | 135% |
| O-(2-THF)-GHB (58) [b] | 199% | 201% |
| 4-hydroxybutyl (O-ethoxycarbonyl)-GHB (63a) [b] | 120% | 73% |
| 4-hydroxybutyl O-acetyl-GHB (63b) [b] | 215% | 149% |
| O-(2-THF) BD (66) [c, e] | 72% | 76% |
| O-(2-THF) BD (66) [b] | 200% | 137% |
| glycerol tris-O-(2-THF) ether (69a) [d] | 46% | 34% |
| erythritol tetrakis-O-(2-THF) ether (69b) [d] | 279% | 151% |
| xylitol pentakis-O-(2-THF) ether (69c) [d] | 129% | 68% |
| 2-OH-THF [c] | 297% | 188% |
| GBL [c] | 70% | 27% |
| BD [c] | 82% | 86% |
| O-(ethoxycarbonyl)-GHB [c, e] | 51% | 54% |

[a] Dose in this study was equivalent to 70 mg/kg NaGHB. Data shown extrapolated to 100 mg/kg (assuming dose proportionality) for easier comparison with other studies.
[b] Vehicle = PEG-400/water (1:1)
[c] Vehicle = water
[d] Vehicle = PEG-400/water (1:3)
[e] Dose in this study was equivalent to 80 mg/kg NaGHB. Data shown extrapolated to 100 mg/kg (based on dose proportionality) for easier comparison with other studies.

All features disclosed in the specification, including the claims, abstracts, and drawings, and all the steps in any method or process disclosed, may be combined in any combination, except combinations where at least some of such features and/or steps are mutually exclusive.

Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Paragraph Claim Set: Paragraphs [0387-0408]

Claim 1. In one embodiment of the present invention is described a compound having a structure of Formula V:

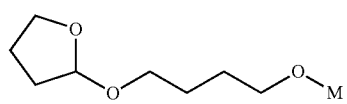

Formula V or a pharmaceutically acceptable salt thereof;
where M is selected from the group consisting of hydrogen, 1,4-butanediol, 2-hydroxytetrahydrofuran, gamma-hydroxybutyrate, sugar alcohol, ethylene glycol, glycerol, erythritol, threitol, arabitol, xylitol, ribitol, mannitol, sorbitol, galactitol, fucitol, iditol, inositol, volemitol, isomalt, lactitol, maltotriitol, maltotetraitol, polyglycitol, gamma-aminobutyric acid, phosphate, sulfate, sulfamate, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, nitro, polycycloalkenyl, polycycloalkenylalkyl, polycycloalkyl, polycycloalkylalkyl, polyethylene glycol, thiol, amino acids, peptides, salts thereof, and combinations thereof.

Claim 2. The compound of Claim 1, wherein the amino acids are selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and salts thereof.

Claim 3. The compound of Claim 1 or 2, wherein the peptide is a dipeptide or a tripeptide.

Claim 4. The compound of claim 1, wherein the compound is selected from the group consisting of

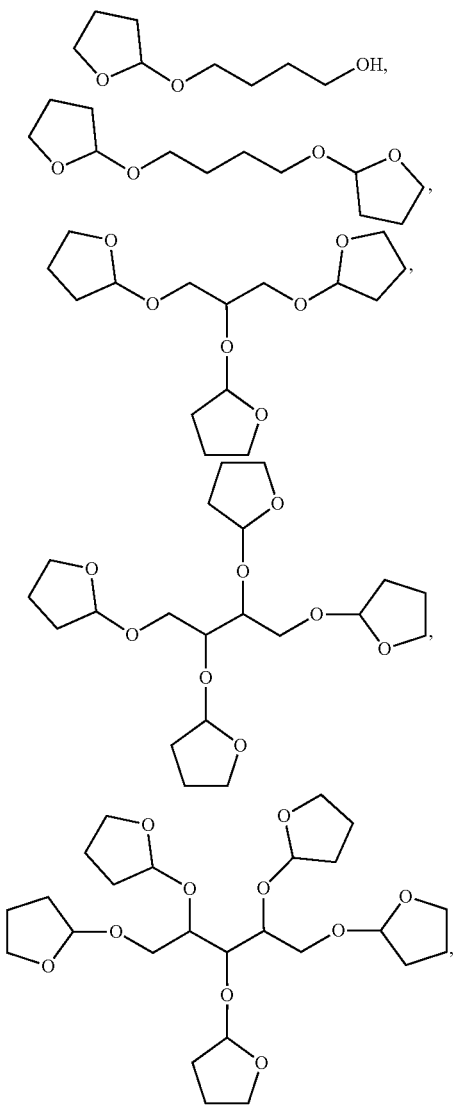

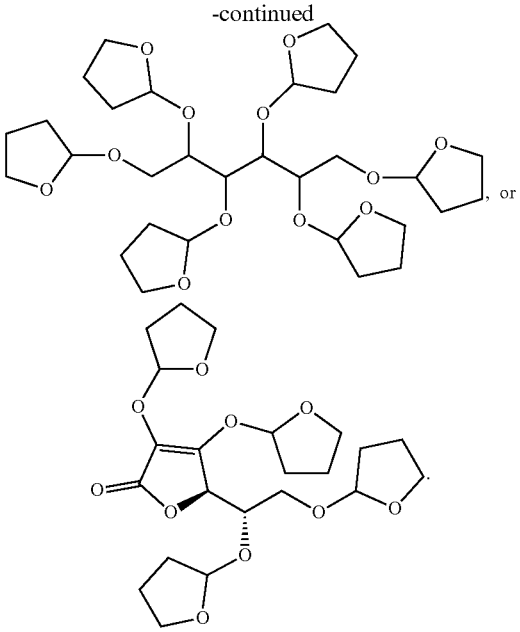

Claim 5. A composition comprising the compound of Claims 1-4, or a pharmaceutically acceptable salt of the compound, wherein the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

Claim 6. A method of preventing or treating a sleep disorder or sleep syndrome in a subject in need thereof, comprising administering to the subject a composition comprising the composition of claim 5.

Claim 7. The method of claim 6, wherein the sleep disorder is a symptom of a degenerative neurological disease or disorder and/or is a side effect of treating a degenerative neurological disease or disorder with medication or a therapeutic compound, wherein the degenerative neurological disease or disorder is selected from the group consisting of Parkinson's disease, primary parkinsonism, paralysis agitans, and idiopathic parkinsonism.

Claim 8. The method of any one of claims 6 to 7, wherein the composition further comprises amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, solriamfetol, or combinations thereof.

Claim 9. The method of any one of claims 6 to 8, wherein the sleep disorder is excessive daytime sleepiness associated with central hypersomnolence disorders, obstructive sleep apnea, or shift work disorder, wherein the central hypersomnolence disorder is selected from the group consisting of narcolepsy type-1 (with cataplexy), narcolepsy type 2, idiopathic hypersomnia, Kleine-Levin syndrome, hypersomnia due to a medical condition, hypersomnia due to a medication or substance, hypersomnia associated with a psychiatric condition, and insufficient sleep syndrome.

Claim 10. The composition of claim 5 or the method of any one of claims 6-9, wherein the composition further comprises one or more excipients, wherein the excipients are selected from the group consisting of anti-adherents, binders, coatings, disintegrants, fillers, flavors, dyes, colors, glidants, lubricants, preservatives, sorbents, sweeteners, derivatives thereof, and combinations thereof.

Claim 11. The composition of claim 5 or the method of any one of claims 6 to 10, composition has a dosing regimen that is about one to two times a day.

Claim 12. The composition of claim 5 or the method of any one of claims 6 to 11, wherein the composition has a dosing regimen that is about one time a day, wherein the composition is orally administered to a human or an animal subject.

Claim 13. A kit comprising a therapeutically effective amount of a compound of any one of claims 1 to 4 or pharmaceutically acceptable salt thereof, wherein the compound is in a unit dosage form, and wherein further the unit dosage form is selected from the group consisting of a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a slurry, a sachet, a buccal tablet, and a suppository, and instructions for use thereof.

Claim 14. The kit of claim 13, wherein the kit further comprises an additional therapeutic compound, wherein the additional therapeutic compound is selected from the group consisting of amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, solriamfetol, and combinations thereof.

Claim 15. The kit of claim 14, wherein the additional therapeutic compound is in a unit dosage form, wherein the unit dosage form is selected from the group consisting of a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a slurry, a sachet, a buccal tablet, and a suppository.

Claim 16. The kit of claim 15, wherein the compound of any one of claims 1 to 4 is in a liquid dosage form and the additional therapeutic compound is in an oral powder form or sachet form.

Claim 17. The kit of claim 16, wherein the additional therapeutic compound is added to the liquid dosage form of the compound prior to administration. In another aspect of the invention, the instructions of use for the kit of claims 13-17 includes instructions for administration of at least one of the compounds of claims 1 to 4, administration of at least one of the additional therapeutic compounds, and/or salt thereof or combinations thereof.

Claim 18. An oral formulation comprising a therapeutically effective dose of compound of any one of claims 1 to 4 or a pharmaceutically acceptable salt thereof.

Claim 19. The oral formulation of claim 18, wherein the oral formulation further comprises one or more excipients, wherein the excipients are selected from the group consisting of anti-adherents, binders, coatings, disintegrants, fillers, flavors, dyes, colors, glidants, lubricants, preservatives, sorbents, sweeteners, derivatives thereof, and combinations thereof.

Claim 20. The oral formulation of claim 18 or claim 19, wherein the therapeutically effective dose is in a unit dosage form, wherein the unit dosage form is selected from the group consisting of a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a slurry, a sachet, and a buccal tablet.

Claim 21. The oral formulation of any one of claims 18-20, wherein the oral formulation has a dosing regimen that is about one to two times a day.

Claim 22. The oral formulation of any one of claims 18 to 21, wherein the oral formulation has a dosing regimen that is about one time a day, wherein the oral formulation is orally administered to a human or an animal subject.

In another embodiment of the present invention is provided a method of preventing or treating a sleep disorder or a sleep syndrome in a subject in need thereof, comprising administering to the subject a composition comprising a compound or a pharmaceutically acceptable salt of the compound selected from the group consisting of

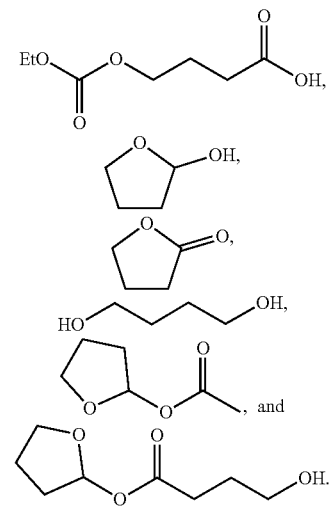

In one alternative of this method, the sleep disorder is a symptom of a degenerative neurological disease or disorder and/or is a side effect of treating a degenerative neurological disease or disorder with medication or a therapeutic compound. The degenerative neurological disease or disorder may, in one alternative of this method be selected from the group consisting of Parkinson's disease, primary parkinsonism, paralysis agitans, and idiopathic parkinsonism. The sleep disorder may be selected, in one alternative of this method, from the group consisting of excessive daytime sleepiness associated with central hypersomnolence disorders, obstructive sleep apnea, or shift work disorder. The central hypersomnolence disorder disorder may, in one alternative of this method, be selected from the group consisting of narcolepsy type 1 (with cataplexy), narcolepsy type 2, idiopathic hypersomnia, Kleine-Levin syndrome, hypersomnia due to a medical condition, hypersomnia due to a medication or substance, hypersomnia associated with a psychiatric condition, and insufficient sleep syndrome. The composition of this method may further comprise one or more of the following (active ingredients or compounds), such as for example amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, and solriamfetol, or combinations thereof. In some alternatives of this method, the composition of this method may also further comprise one or more excipients, wherein the excipients are selected from the group consisting of anti-adherents, binders, coatings, disintegrants, fillers, flavors, dyes, colors, glidants, lubricants, preservatives, sorbents, sweeteners, derivatives thereof, and combinations thereof. In some alternatives of this method, the composition of this method may also further comprise the one or more additional active ingredients/compounds mentioned above along with the one or more excipients mentioned above.

In one embodiment of the above method of preventing or treating a sleep disorder or a sleep syndrome in a subject in need thereof, the composition has a dosing regimen that is about two times a day or less, and more preferably one to two times a day. In another embodiment, the composition has a dosing regimen that is about one time a day. The composition may be administered to the subject, wherein the subject is an animal or human, via oral, intranasal, intradermal, intramascular, depot injection, subcutaneous, or intravenous means. In one alternative method, the composition is orally administered to a human or an animal subject.

In another embodiment of the above technology is provided a kit comprising a therapeutically effective amount of a composition of the present invention (or alternatively a kit for the method of preventing or treating a sleep disorder or a sleep syndrome in a subject in need thereof, comprising a therapeutically effective amount of a composition of the present invention), or a pharmaceutically acceptable salt or salts thereof, wherein the composition is in a unit dosage form. The unit dosage form may be selected from the group consisting of a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a slurry, a sachet, a buccal tablet, and a suppository. Such a kit may further additionally comprise one or more additional therapeutic compounds. The one or more additional therapeutic compound(s) may be selected from the group consisting of amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, solriamfetol, and combinations thereof. The one or more additional therapeutic compound(s) may be provided in an unit dosage form, wherein the unit dosage form is selected from the group consisting of a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a slurry, a sachet, a buccal tablet, and a suppository. In another aspect of the invention, such a kit further comprises instructions for use, wherein the instruction for use includes instructions for administration of at least one composition, administration of at least one of the additional therapeutic compounds, and/or (pharmaceutically acceptable) salt(s) thereof or combinations thereof.

In the method or kit of any one or more of paragraphs 243-246 above, the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof. In another aspect of the present invention, the pharmaceutically acceptable salt may also be selected from the group additionally comprising salts of an amphetamine (such as for example amphetaminium), methylphenidate and serdexmethylphenidate.

It will be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A compound is selected from the group consisting of

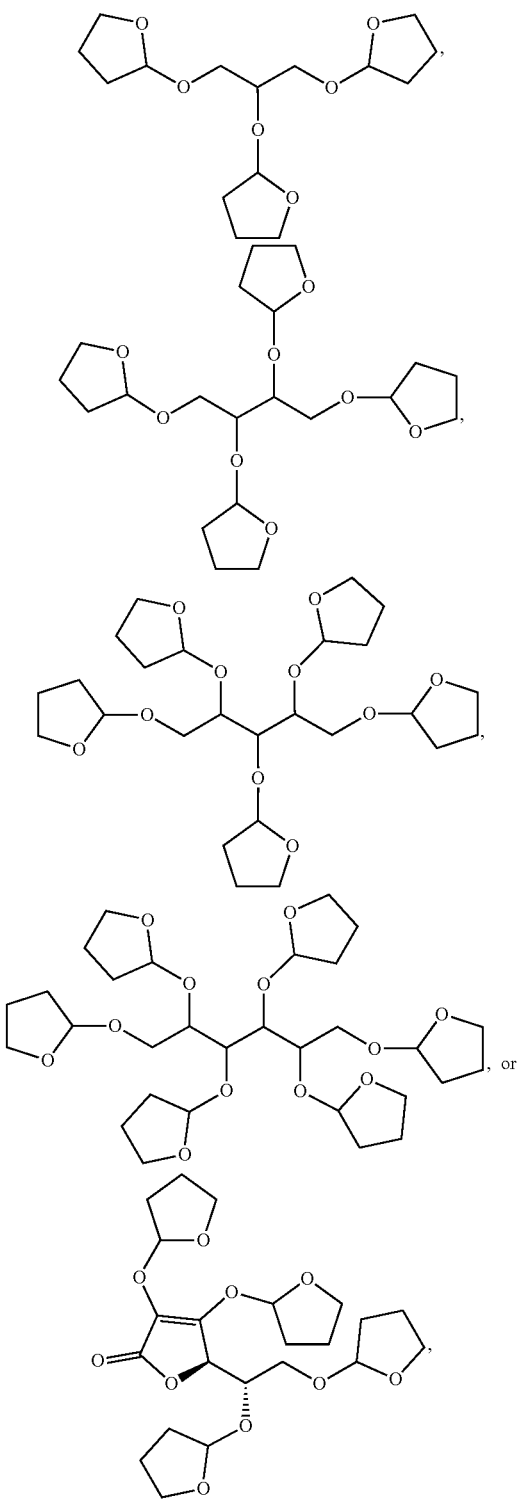

or a pharmaceutically acceptable salt thereof.

2. A composition comprising the compound claim 1, or a pharmaceutically acceptable salt of the compound, wherein the pharmaceutically acceptable salt is selected from the group consisting of an acetate, L-aspartate, besylate, bicarbonate, carbonate, D-camsylate, L-camsylate, citrate, edisylate, formate, fumarate, gluconate, hydrobromide/bromide, hydrochloride/chloride, D-lactate, L-lactate, D,L-lactate, D,L-malate, L-malate, mesylate, pamoate, phosphate, succinate, sulfate, bisulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate, galacturonate, gallate, gentisate, glutamate, glutarate, glycerophosphate, heptanoate, hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate, sodium, potassium, calcium, magnesium, zinc, aluminum, lithium, cholinate, lysinium, ammonium, troethamine, and a mixture thereof.

3. A method of preventing or treating a sleep disorder or sleep syndrome in a subject in need thereof, comprising administering to the subject a composition comprising the composition of claim 2.

4. The method of claim 3, wherein the sleep disorder is a symptom of a degenerative neurological disease or disorder and/or is a side effect of treating a degenerative neurological disease or disorder with medication or a therapeutic compound, wherein the degenerative neurological disease or disorder is selected from the group consisting of Parkinson's disease, primary parkinsonism, paralysis agitans, and idiopathic parkinsonism.

5. The method of any one of claims 3 to 4, wherein the composition further comprises amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, solriamfetol, or combinations thereof.

6. The method of claim 3, wherein the sleep disorder is excessive daytime sleepiness associated with central hypersomnolence disorders, obstructive sleep apnea, or shift work disorder, wherein the central hypersomnolence disorder is selected from the group consisting of narcolepsy type-1 (with cataplexy), narcolepsy type 2, idiopathic hypersomnia, Kleine-Levin syndrome, hypersomnia due to a medical condition, hypersomnia due to a medication or substance, hypersomnia associated with a psychiatric condition, and insufficient sleep syndrome.

7. The composition of claim 2, wherein the composition further comprises one or more excipients, wherein the excipients are selected from the group consisting of antiadherents, binders, coatings, disintegrants, fillers, flavors, dyes, colors, glidants, lubricants, preservatives, sorbents, sweeteners, derivatives thereof, and combinations thereof.

8. The composition of claim 2, composition has a dosing regimen that is about one to two times a day.

9. The composition of claim 8, wherein the composition has a dosing regimen that is about one time a day, wherein the composition is orally administered to a human or an animal subject.

10. A kit comprising a therapeutically effective amount of a compound of claim 1 or pharmaceutically acceptable salt thereof, wherein the compound is in a unit dosage form, and wherein further the unit dosage form is selected from the group consisting of a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a slurry, a sachet, a buccal tablet, and a suppository, and instructions for use thereof.

11. The kit of claim 10, wherein the kit further comprises an additional therapeutic compound, wherein the additional therapeutic compound is selected from the group consisting of amantadine, aplindore, apomorphine, benztropine, bromocriptine, carbidopa, entacapone, fenoldopam, istradefylline, levodopa (L-dopa), opicapone, pramipexole, rasagiline, ropinirole, rotigotine, safinamide, tolcapone, trihexyphenidyl, amphetamine, armodafinil, caffeine, mazindol, methylphenidate, modafinil, pitolisant, reboxetine, samelisant, serdexmethylphenidate, solriamfetol, and combinations thereof.

12. The kit of claim 11, wherein the additional therapeutic compound is in a unit dosage form, wherein the unit dosage form is selected from the group consisting of a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a slurry, a sachet, a buccal tablet, and a suppository.

13. The kit of claim 12, wherein the compound claim 4 is in a liquid dosage form and the additional therapeutic compound is in an oral powder form or sachet form.

14. The kit of claim 13, wherein the additional therapeutic compound is added to the liquid dosage form of the compound prior to administration.

15. An oral formulation comprising a therapeutically effective dose of compound of claim 1 or a pharmaceutically acceptable salt thereof.

16. The oral formulation of claim 15, wherein the oral formulation further comprises one or more excipients, wherein the excipients are selected from the group consisting of anti-adherents, binders, coatings, disintegrants, fillers, flavors, dyes, colors, glidants, lubricants, preservatives, sorbents, sweeteners, derivatives thereof, and combinations thereof.

17. The oral formulation of claim 15 or claim 16, wherein the therapeutically effective dose is in a unit dosage form, wherein the unit dosage form is selected from the group consisting of a sublingual, a gummy, a chewable tablet, a rapidly dissolving tablet, a tablet, a capsule, a caplet, a troche, a lozenge, an oral powder, a solution, a liquid, a thin strip, an oral thin film (OTF), an oral strip, a syrup, a suspension, a slurry, a sachet, and a buccal tablet.

18. The oral formulation of claim 17, wherein the oral formulation has a dosing regimen that is about one to two times a day.

19. The oral formulation of claim 18, wherein the oral formulation has a dosing regimen that is about one time a day, wherein the oral formulation is orally administered to a human or an animal subject.

* * * * *